(12) United States Patent
Lee et al.

(10) Patent No.: US 10,801,054 B2
(45) Date of Patent: Oct. 13, 2020

(54) BIOMIMETIC VIRUS-BASED COLORIMETRIC SENSORS

(71) Applicant: THE REGENTS OF THE UNIVERSITY OF CALIFORNIA, Oakland, CA (US)

(72) Inventors: Seung-Wuk Lee, Walnut Creek, CA (US); Woo-Jae Chung, El Cerrito, CA (US); Jin-Woo Oh, Albany, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/430,677

(22) Filed: Jun. 4, 2019

(65) Prior Publication Data

US 2019/0390243 A1 Dec. 26, 2019

Related U.S. Application Data

(62) Division of application No. 15/105,547, filed as application No. PCT/US2014/071963 on Dec. 22, 2014, now Pat. No. 10,590,459.

(Continued)

(51) Int. Cl.
*G01N 35/00* (2006.01)
*G01N 33/00* (2006.01)
(Continued)

(52) U.S. Cl.
CPC .................. *C12Q 1/02* (2013.01); *C12N 7/00* (2013.01); *C12Q 1/6825* (2013.01); *G01N 21/78* (2013.01);
(Continued)

(58) Field of Classification Search
CPC .......... C12Q 1/02; C12Q 1/6825; C12N 7/00; C12N 2795/14131; G01N 21/78;
(Continued)

(56) References Cited

U.S. PATENT DOCUMENTS 5,403,484 A  4/1995  Ladner et al.
5,766,905 A  6/1998  Studier et al.
(Continued)

FOREIGN PATENT DOCUMENTS

WO  WO 2009/009186  1/2009
WO  WO 2015/095882  6/2015

OTHER PUBLICATIONS

Berliner JFT, May OE. Studies in vapor pressure II the mononitrotoluenes. Journal of the American Chemical Society 48, 2630-2634 (1926).
(Continued)

*Primary Examiner* — Brian J. Sines
(74) *Attorney, Agent, or Firm* — Tom Hunter; Weaver Austin Villeneuve & Sampson LLP

(57) ABSTRACT

The present invention provides, inter alia, a device comprising a colorimetric detection layer configured to undergo a color change upon interaction with a first analyte of interest. The detection layer comprises a first plurality of self-assembled fiber bundles. At least a fraction of the fiber bundles undergo a change from a first conformation to a second conformation upon interaction with the first analyte of interest, thereby undergoing a color change. The invention also provides a method for using the system to detect an analyte of interest.

16 Claims, 45 Drawing Sheets
(43 of 45 Drawing Sheet(s) Filed in Color)
Specification includes a Sequence Listing.

Related U.S. Application Data

(60) Provisional application No. 61/919,663, filed on Dec. 20, 2013.

(51) Int. Cl.

| | |
|---|---|
| *G01N 33/48* | (2006.01) |
| *G01N 21/78* | (2006.01) |
| *C12Q 1/02* | (2006.01) |
| *C12N 7/00* | (2006.01) |
| *C12Q 1/6825* | (2018.01) |
| *G01N 21/81* | (2006.01) |
| *G01N 33/22* | (2006.01) |
| *G01N 15/06* | (2006.01) |

(52) U.S. Cl.
CPC ........... *G01N 21/783* (2013.01); *G01N 21/81* (2013.01); *G01N 33/227* (2013.01); *C12N 2795/14131* (2013.01); *G01N 2333/01* (2013.01)

(58) Field of Classification Search
CPC .......... G01N 21/81; G01N 7/00; G01N 21/00; G01N 27/00; G01N 31/00; G01N 33/00; G01N 1/22; G01N 35/00; G01N 33/48; G01N 15/06; G01N 21/783; G01N 33/227; G01N 2333/01
USPC ...... 422/50, 68.1, 400, 82.05, 82.09, 83, 85, 422/86; 436/43, 164, 169, 173
See application file for complete search history.

(56) References Cited

U.S. PATENT DOCUMENTS

| | | | |
|---|---|---|---|
| 5,885,808 | A | 3/1999 | Spooner et al. |
| 6,210,976 | B1* | 4/2001 | Sabbadini .......... G01N 33/6893 435/7.1 |
| 6,261,554 | B1 | 7/2001 | Valerio et al. |
| 7,332,321 | B2 | 10/2008 | Belcher et al. |
| 7,527,981 | B2 | 5/2009 | Farwell et al. |
| 7,632,637 | B1* | 12/2009 | Boss ................ G01N 33/56911 435/235.1 |
| 7,794,657 | B2 | 9/2010 | Stewart |
| 8,957,013 | B2 | 2/2015 | Jaworski et al. |
| 10,590,459 | B2 | 3/2020 | Lee et al. |
| 2001/0019820 | A1 | 9/2001 | Li |
| 2005/0153386 | A1* | 7/2005 | Farwell .............. G01N 33/5432 435/34 |
| 2005/0164299 | A1* | 7/2005 | Stewart ............ G01N 33/54373 435/7.1 |
| 2005/0180992 | A1* | 8/2005 | Belcher ................. A61K 35/76 424/204.1 |
| 2006/0292559 | A1 | 12/2006 | Reddy |
| 2007/0065884 | A1 | 3/2007 | Zuker |
| 2008/0180259 | A1* | 7/2008 | Jung ................. G01N 35/0092 340/627 |
| 2011/0311490 | A1 | 12/2011 | Lee et al. |
| 2014/0072189 | A1 | 3/2014 | Jena et al. |
| 2016/0056361 | A1 | 2/2016 | Darwish |
| 2016/0312262 | A1 | 10/2016 | Lee et al. |

OTHER PUBLICATIONS

Bonifacio, L. D. et al. Towards the Photonic Nose: A Novel Platform for Molecule and Bacteria Identification. Advanced Materials 22, 1351-1354, (2010).
Bradbury, J. W. & Vehrencamp, S. L. Principles of animal communication. xiii, 882 p. (Sinauer Associates, Sunderland, MA) (1998).
Burgess, I. B. et al. Encoding Complex Wettability Patterns in Chemically Functionalized 3D Photonic Crystals. Journal of the American Chemical Society 133, 12430-12432, (2011).
Burgess, I. B. et al. Wetting in Color: Colorimetric Differentiation of Organic Liquids with High Selectivity. ACS Nano 6, 1427-1437 (2012).
Chung, W.-J. et al. Biomimetic self-templating supramolecular structures. Nature 478, 364-368, (2011).
Crookes, W. J. et al. Reflections: The Unusual Proteins of Squid Reflective Tissues. Science 303, 235-238, (2004).
Dang, X. et al. Virus-templated self-assembled single-walled carbon nanotubes for highly efficient electron collection in photovoltaic devices. Nature Nanotechnology 6, 377-384, (2011).
Debouck et al., in supplement to Nature Genetics, 21:48-50 (1999).
Fink, Y. et al. A Dielectric Omnidirectional Reflector. Science 282, 1679-1682 (1998).
Forster, J. D. et al. Biomimetic Isotropic Nanostructures for Structural Coloration. Advanced Materials 22, 2939-2944, (2010).
Ge, J. & Yin, Y. Responsive Photonic Crystals. Angewandte Chemie International Edition 50, 1492-1522, (2011).
Goldman, E. R., et al., Selection of phage displayed peptides for the detection of 2,4,6-trinitrotoluene in seawater. Analytica Chimica Acta 457, 13-19, (2002).
Hickman et al., J. Vac. Sci. Technol. 12:607-16 (1994).
Holtz, J. H. & Asher, S. A. Polymerized colloidal crystal hydrogel films as intelligent chemical sensing materials. Nature 389, 829-832 (1997).
Jaworski, J. W. et al., Evolutionary Screening of Biomimetic Coatings for Selective Detection of Explosives. Langmuir 24, 4938-4943 (2008).
Kang, Y., Walish, J. J., Gorishnyy, T. & Thomas, E. L. Broad-wavelength-range chemically tunable block-copolymer photonic gels. Nature Materials 6, 957-960, (2007).
Kelly, T. L., Garcia Sega, A. & Sailor, M. J. Identification and Quantification of Organic Vapors by Time-Resolved Diffusion in Stacked Mesoporous Photonic Crystals. Nano Letters 11, 3169-3173, (2011).
Kim, J. H., Moon, J. H., Lee, S.-Y. & Park, J. Biologically inspired humidity sensor based on three-dimensional photonic crystals. Applied Physics Letters 97, 103701-103703 (2010).
Kim, T. H. et al. Selective and Sensitive TNT Sensors Using Biomimetic Polydiacetylene-Coated CNT-FETs. ACS Nano 5, 2824-2830, (2011).
Kinoshita, S. & Yoshioka, S. Structural Colors in Nature: The Role of Regularity and Irregularity in the Structure. ChemPhysChem 6, 1442-1459 (2005).
Kleinfield et al., J. Neurosci. 8:4098-120 (1998).
Kolle, M. et al. Mimicking the colorful wing scale structure of the Papilio blumei butterfly. Nature Nanotechnology 5, 511-515 (2010).
Kramer, R. M., Crookes-Goodson, W. J. & Naik, R. R. The self-organizing properties of squid reflectin protein. Nature Materials 6, 533-538 (2007).
Kumar et al., Langmuir 10: 1498-511 (1994).
Lee, S. et al., Ordering of Quantum Dots Using Genetically Engineered Viruses. Science 296, 892-895, (2002).
Lee, Y. J. et al. Fabricating Genetically Engineered High-Power Lithium-Ion Batteries Using Multiple Virus Genes. Science 324, 1051-1055, (2009).
Lim, S. H., et al., An optoelectronic nose for the detection of toxic gases. Nature Chemistry 1, 562-567, (2009).
Mao, C. et al. Virus-Based Toolkit for the Directed Synthesis of Magnetic and Semiconducting Nanowires. Science 303, 213-217, (2004).
Mao, C. et al., Virus-Based Chemical and Biological Sensing. Angewandte Chemie-International Edition 48, 6790-6810 (2009).
Merzlyak, A. et al., Genetically Engineered Nanofiber-Like Viruses for Tissue Regenerating Materials. Nano Letters 9, 846-852, (2009).
Mrkish, M.; Whitesides, G. M., Ann. Rev. Biophys. Biomol. Struct. 25:55-78 (1996).
Nam, K. T. et al, Virus-Enabled Synthesis and Assembly of Nanowires for Lithium Ion Battery Electrodes. Science 312, 885-888, (2006).
Noh, H. et al. How Noniridescent Colors Are Generated by Quasi-ordered Structures of Bird Feathers. Advanced Materials 22, 2871-2880, (2010).

(56) References Cited

OTHER PUBLICATIONS

Ostmark H, Wallin S, Ang HG. Vapor Pressure of Explosives: A Critical Review, Propellants Explosives Pyrotechnics 37, 12-23 (2012).

Potyrailo, R. A. et al. Morpho butterfly wing scales demonstrate highly selective vapor response. Nature Photonics 1, 123-128, (2007).

Prum, R. O. & Torres, R. Structural coloration of avian skin: convergent evolution of coherently scattering dermal collagen arrays. Journal of Experimental Biology 206, 2409-2429 (2003).

Prum, R. O. & Torres, R. H. Structural coloration of mammalian skin: convergent evolution of coherently scattering dermal collagen arrays. Journal of Experimental Biology 207, 2157-2172 (2004).

Prum, R. O., Torres, R. H., Williamson, S. & Dyck, J. Coherent light scattering by blue feather barbs. Nature 396, 28-29 (1998).

Rittfeldt L. Determination of vapor pressure of low-volatility compounds using a method to obtain saturated vapor with coated capillary columns. Analytical Chemistry 73, 2405-2411 (2001).

Sharma, V., et al. Structural Origin of Circularly Polarized Iridescence in Jeweled Beetles. Science 325, 449-451, (2009).

Sigal, G., Whitesides, G., Anal Chem. 68, 490, (1996).

Sanghvi, A. et al., Biomaterials functionalization using a novel peptide that selectively binds to a conducting polymer. Nature Materials 4, 496-502, (2005).

Tao, A. R. et al. The role of protein assembly in dynamically tunable bio-optical tissues. Biomaterials 31, 793-801 (2010).

Vigneron, J. P. et al. Switchable reflector in the Panamanian tortoise beetle *Charidotella egregia* (Chrysomelidae: Cassidinae). Physical Review E 76, 031907 (2007).

Vukusic, P. & Sambles, J. R. Photonic structures in biology. Nature 424, 852-855 (2003).

Xia, Y;. Whitesides, G., J. Am. Chem. Soc. 117:3274-75 (1995).

Young, R. E. & Mencher, F. M. Bioluminescence in mesopelagic squid: diel color change during counterillumination. Science 208, 1286-1288 (1980).

Zakhidov, A. A. et al. Carbon Structures with Three-Dimensional Periodicity at Optical Wavelengths. Science 282, 897-901 (1998).

PCT International Search Report and Written Opinion dated Mar. 20, 2015 issued in PCT/US2014/071963.

PCT International Preliminary Report on Patentability and Written Opinion dated Jun. 21, 2016 issued in PCT/US2014/071963.

U.S. Office Action dated Mar. 29, 2018 issued in U.S. Appl. No. 15/105,547.

U.S. Final Office Action dated Oct. 4, 2018 issued in U.S. Appl. No. 15/105,547.

U.S. Advisory Action dated May 2, 2019 issued in U.S. Appl. No. 15/105,547.

U.S. Notice of Allowance dated Nov. 6, 2019 issued in U.S. Appl. No. 15/105,547.

\* cited by examiner

BIOMIMETIC VIRUS-BASED COLORIMETRIC SENSORS

CROSS REFERENCE TO RELATED APPLICATIONS

This application is a Divisional of U.S. patent application Ser. No. 15/105,547 filed on Jun. 16, 2016, which is a 371 application of PCT International Application No. PCT/US14/71963 filed on Dec. 22, 2014, which claims benefit of U.S. Provisional Application No. 61/919,663 filed on Dec. 20, 2013, all of which are incorporated herein by reference their entireties.

STATEMENT OF GOVERNMENTAL SUPPORT

This invention was made with government support under 0832819 awarded by the National Science Foundation and under DE-AC02-05CH11231 awarded by the U.S. Department of Energy. The government has certain rights in the invention.

INCORPORATION BY REFERENCE OF SEQUENCE LISTING PROVIDED AS A TEXT FILE

A Sequence Listing is provided herewith as a text file, "UCLA-P097D1US_ST25.txt" created on Aug. 29, 2019 and having a size of 2.64 KB. The contents of the text file are incorporated by reference herein in their entirety.

FIELD OF THE INVENTION

This invention relates generally to sensors based on fibrous molecules.

BACKGROUND OF THE INVENTION

Many animals change their skin colors to communicate, to express mood, for camouflage, or to respond to environmental changes[1-3]. In the tissues of these animals, various nano and microscale components play roles in generating distinct colors and achieving rapid color changes[4,5]. Inspired by nature, sensors are being developed that change color in response to target chemicals by employing biomimetic structures and mechanisms. In particular, structurally colored biomaterials, such as butterfly wings, beetle exocuticles, cephalopod skins, mammalian skins, and avian skins/feathers[6-14], provide insight into developing colorimetric sensors. These materials exhibit brilliant colors that are derived from their hierarchically organized structures and are resistant to photobleaching[7]. Furthermore, they can rapidly shift colors upon exposure to chemical vapors due to structural and/or refractive index changes[15]. Therefore, both structurally colored materials in nature and their synthetic analogues are being explored as simple and portable colorimetric sensor platforms[16-21].

A significant drawback of previous structural color sensors is their limited intrinsic affinity for specific targets of interest (e.g., explosives and pathogens) and resulting poor selectivity against analytes with similar chemical structures. Current methods to promote target specificity by either chemically incorporating specific recognition motifs or by synthesizing arrays of cross responsive platforms for "artificial nose" type pattern recognition are promising[19,22-24], but incorporating analyte-responsive elements into the sensing devices is still challenging because it requires complex designs and multistep synthetic pathways. Furthermore, many structurally colored sensors exhibit viewing-angle dependent color changes (iridescence) that may complicate analysis.

SUMMARY OF THE INVENTION

Various embodiments disclosed herein relate to the field of nanoscale sensors, and more particularly to an apparatus and method for ultrasensitive sensing of analyte of interest, such as chemical and/or biological molecules, using nanoscale sensors. Methods of fabricating a nanoscale sensor apparatus are also disclosed. The nanoscale sensors are able to display real-time signals from a single analyte of interest. The nanoscale sensors are of use in numerous applications, including detection of explosives, pathogens, and in attack, e.g., bio-attack, alarming systems. The invention also finds use in drinking water monitoring, biomolecule characterization in research, constructing an artificial neuronal post-synaptic membrane, food quality test, allergic species detection, forensic examination, pollution monitoring, personnel biological identification and clinical diagnosis.

The present invention also relates to devices and systems for detecting, and methods of detecting the presence or absence and/or quantification of analytes of interest, e.g., explosives, pathogens, substances or molecules by fiber bundles comprised of a plurality of fibrous molecules. In an exemplary embodiment, the invention provides a target sensor including a plurality of fiber bundles immobilized on a solid surface. In some embodiments, the invention relates to detecting the presence, absence, or quantity of an analyte of interest in air, in liquid solution or on a surface. In some embodiments, the invention relates to detecting the presence, absence, or quantity of a molecule in air, in liquid solution or on a surface. In some embodiments, the invention relates to a method of detecting the presence, absence, or quantity of a pathogen or substance derived from a pathogen in air, in liquid solution or on a surface.

An exemplary device includes a detection layer formed from a plurality of aligned fiber bundles. In some embodiments, the device comprises immobilized virus or viral components directionally oriented on a surface. In some embodiments, the device comprises a plurality of immobilized virus or viral proteins. In some embodiments, the virus is a phage or a phage viral protein or modified analog thereof.

In an exemplary embodiment, the invention provides a device comprising a detection layer configured to undergo an optically responsive structural change upon interaction with a first analyte of interest. The detection layer is deposited on a substrate, and comprises a first plurality of self-assembled fiber bundles. At least a fraction of the first plurality of fiber bundles undergoes a change from a first conformation to a second conformation upon interaction with the first analyte of interest, thereby undergoing the optically responsive structural change.

In various embodiments, the present invention provides a device comprising a colorimetric detection layer configured to undergo a color change upon interaction with a first analyte of interest. The detection layer comprises a first plurality of self-assembled fiber bundles. At least a fraction of the fiber bundles undergo a change from a first conformation to a second conformation upon interaction with the first analyte of interest, thereby undergoing a color change.

The invention further relates to a method of isolating a molecule or substance comprising exposing any device or sensor disclosed herein to a gas, solution or a surface comprising the analyte of interest or surface suspected of comprising the analyte of interest. In some embodiments, the analyte of interest is an explosive, a pathogen, or radioactive isotope. In some embodiments, the method comprises contacting a swab or other sampling element to a surface or solution comprising the analyte of interest or suspected of comprising the analyte of interest, exposing the swab or other sampling element to any device or sensor disclosed herein, and detecting a color change.

The invention also relates to a device or sensor with a solid surface comprising at least one or a plurality viruses or viral proteins oriented in a longitudinal fashion.

In various embodiments, the invention provides a device comprising: (i) a phage bundle structure comprising a plurality of genetically engineered bacteriophages capable of binding to a analyte of interest, wherein the binding of one or more of the genetically engineered bacteriophages to the analyte of interest causes a color change of the phage bundle structure, and (ii) a means for detecting said color change. An exemplary phage bundle structure comprises helical nanofilament bundles of aligned genetically engineered bacteriophages. In some embodiments, the phage bundle structure resides on a substrate.

Further in accordance with the present invention, the device and/or sensors and/or arrays disclosed herein are used to identify and/or characterize the safety of food or water. For example, in some embodiments the devices or sensors provided herein are used to identify food samples or water samples comprising a pathogen from food samples or water samples that do not comprises a pathogen.

In various embodiments, the invention also provides a method of detecting an analyte of interest comprising: (a) providing the system of the present invention, (b) contacting one or more analyte of interest to the one or more of the genetically engineered bacteriophages of the system, and (c) displaying a resulting that indicates a color change.

In an exemplary embodiment, the invention provides an apparatus configured to accomplish the methods described herein or is the means for detecting the color change resulting from interaction with the analyte of interest. A suitable apparatus includes hardware for accomplishing the process operations and a system controller having instructions for controlling process operations in accordance with the disclosed embodiments. The system controller will typically include one or more memory devices and one or more processors configured to execute the instructions so that the apparatus will perform a method in accordance with the disclosed embodiments, such as the workflow depicted in FIG. 30. Machine-readable media containing instructions for controlling process operations in accordance with the disclosed embodiments may be coupled to the system controller.

In some embodiments, the genetically engineered bacteriophage is a recombinant M13 bacteriophage comprising an amino acid sequence that can bind the analyte of interest.

Other objects, advantages and exemplifications of the invention will be apparent from the detailed description below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and others will be readily appreciated by the skilled artisan from the following description of illustrative embodiments when read in conjunction with the accompanying drawings.

FIG. 2A) Phages genetically engineered to recognize analyte of interest through directed evolution, replicate to create identical copies and then self-assemble into colored matrices composed of quasi-ordered bundled structures. FIG. 2B) Composite of AFM images from different matrices (bands) of a Phage litmus. Each matrix is composed of quasi-ordered fiber bundles with different diameter and interspacing and exhibits a different color. FIG. 2C) A fabricated Phage litmus exhibiting four distinct colors; orange, green, blue, and deep blue (in red box). Changes in relative humidity (RH) result in changes in colors. Depending on the initial phage bundle structure, each phage matrix swells with a different ratio and exhibits a different color change.

FIG. 3A) Photographs of the Phage litmus after exposure to hexane, diethyl ether, isopropyl alcohol, ethanol, methanol, and, DI-water, respectively. FIG. 3B) Real-time RGB (red, green, and blue) color change profile of a Phage litmus after exposure to DI-water. Each plot represents the RGB color intensity change from each matrix of a Phage litmus. Time-dependent RGB color change profiles for the other VOC sensing experiments are shown in FIG. 14. FIG. 3C) VOC color fingerprints used to selectively distinguish various chemicals. FIG. 3D) Principle component analysis plot of the color changes resulting from the exposure of the Phage litmus to different VOCs.

FIG. 4A) 2700 copies of the TNT binding receptor (WHWQ) within the TNT binding peptide (ADDWHWQEGDP, SEQ ID NO:1) identified by directed evolution are genetically engineered onto the surface of M13 phage (TNT-phage). FIG. 4B) Using the iPhone-based analysis system, TNT is detectable down to 300 ppb in the gas phase. The dashed redline indicates the sensitivity limit of the TNT-Phage litmus against TNT. FIG. 4C) Photos and processed color fingerprints from the TNT-Phage litmus after TNT, DNT, and MNT exposure. The TNT-Phage litmus selectively detects the target TNT (20 ppm) over other molecules with similar chemical structures, such as DNT (20 ppm) and MNT (300 ppm).

FIGS. 6A, 6B, 6C) Reflectance spectra from the $3^{rd}$, $4^{th}$, and $5^{th}$ phage litmus bands from FIG. 5.

FIG. 8A) AFM images and two-dimensional FFT images of the Phage litmus matrices at RH 35%. Each band is composed of different diameter phage bundle fiber s by controlling the pulling speed. A different periodicity of phage bundles within each band can exhibit a different color. As pulling speed is increased, the power distribution is expanded in the horizontal direction due to increased high frequency components from the thinner and more narrowly spaced phage bundles. FIG. 8B) AFM images and two-dimensional FFT images of the Phage litmus matrices at RH 90%. When RH increased from 35% to 90%, the phage bundle within each band swelled with a different ratio depending on the initial phage bundle structure. FIG. 8C) Comparison of the spatial power spectra of each band in the Phage litmus at RH 35% and 90%. When RH increased from 35% to 90%, the width of spatial power spectrum was reduced due to the decreased high frequency components coming from the thicker and more widely spaced phage bundles through swelling. The fitting curve was calculated by Gaussian function ($w_{1/2}$: full width at half maximum). The scale bars in FIG. 8A and FIG. 8B are 5 μm.

(FIG. 10B) $2^{nd}$ band 365 nm to 416 nm; (FIG. 10C) $3^{rd}$ band 331 to 371 nm; (FIG. 10D) $4^{th}$ band 313 to 336 nm. FIG. 10E) When humidity increased from 35% to 90%, the peak wavelength positions shifted to longer wavelengths (Δλ=124, 75, 55, and 28 nm), bundle diameters (D) increased (ΔD=120, 87, 55, and 32 nm), and matrix thicknesses (T) increased (ΔT=82, 51, 40, and 23 nm) at the $1^{st}$, $2^{nd}$, $3^{rd}$, and $4^{th}$ bands, respectively. The bundle diameters and matrix thicknesses were determined from measurements of twenty different bundles from AFM images. The bundle diameter was measured as the full width at half maximum (FWHM) from AFM height profiles. FIG. 10F) AFM height profiles of the $1^{st}$ matrix cross-section, shown in FIG. 2C, at 35% RH (black line) and 90% RH (red line).

FIG. 11A) GISAXS patterns of the Phage litmus, (X-ray propagation parallel to the nanofilament structures) before the application of humidity (left) and after exposure to 100% relative humidity (right). FIG. 11B) In situ line averaged GISAXS spectra taken every 3 min up to 30 min after humidity exposure. With the application of humidity, the (100) and (110) peaks from the semantically-ordered nanofilament structures gradually disappeared.

FIG. 17A) SPR spectroscopy investigation of the TNT-binding-phage immobilized substrates showed that the resulting engineered TNT-binding-phage could recognize the target TNT (500 pM) in a sequence specific manner. Alanine-substituted control phage (WAW, WHA, and AHW) and wild-type phage exhibited significantly reduced binding affinity for the TNT molecules. FIG. 17B) Selectivity screening of the TNT-binding-phage against the same concentrations of TNT (500 pM), DNT (500 pM), and MNT (500 pM). The TNT-binding-phage responded selectively to the TNT over the similarly structured chemicals DNT and MNT.

FIG. 18A) Two-dimensional FFT diffraction pattern of the TNT-Phage litmus before (control) and after TNT gas (20 ppm) exposure. FIG. 18B) Experimental diffraction pattern obtained from a laser incident on the TNT-Phage litmus before (control) and after TNT exposure. The TNT-Phage litmus bound with TNT exhibited a narrower diffraction pattern, which is in good agreement with the obtained FFT image shown in FIG. 18A. Scale bar is 2 mm.

FIG. 19A) Fourier transform infrared (FT-IR) spectroscopy (Nicolet AVATAR 350 FT-IR spectrometer equipped with a SMART MIRacle ZnSe ATR accessory) data of TNT-Phage litmus bound with TNT in gas and liquid phases. After exposure of the TNT to TNT-Phage litmus, observed a TNT peak in the FT-IR spectrum (1352 $cm^{-1}$; Symmetric $NO_2$ stretch) was observed. FIG. 19B) Within the FT-IR spectrum, there are absorbance peaks at 2922 and 2853 $cm^{-1}$ attributed to the stretching vibration mode of the C—H bond in benzene and the alkyl groups in Trp (W) and His (H). After binding between TNT-binding phage (WHW) and TNT, it is clearly observed that the intensity of the C—H vibration band becomes weak as the TNT concentration is increased. In order to normalize the changes of C—H vibration intensity, we obtained ratio of $v_{2922cm}^{-1}/v_{1652cm}^{-1}$ ($v_{2922cm}^{-1}$ is the peak related with C—H vibration mode in Trp and His which is decreased with increasing TNT concentration, and $v_{1652cm}^{-1}$ is the peak related with C═O stretch mode which is one of peaks maintained a constant intensity with increasing TNT concentration.). The ratio of $v_{2922cm}^{-1}/v_{1652cm}^{-1}$ significantly decreased with TNT concentration due to the multivalent binding between Trp and His, and TNT.

FIG. 20D) In the FT-IR spectra, the intensity change of the C—H bond vibration band between the control and sensing samples in vapor (20 ppm) and liquid (400 μM) TNT, was negligible.

FIG. 24A) Upon exposure to TNT (20 ppm), DNT (400 ppm), and MNT (20,000 ppm) vapors, the TNT-Phage litmus responded selectively to the TNT molecules. FIG. 24B) In a 300 ppm ethanol vapor background the TNT-Phage litmus also responded selectively to the TNT molecules. FIG. 24C) Control experiment using the 4E-Phage litmus. There was negligible color change to TNT (20 ppm), DNT (400 ppm), and MNT (20,000 ppm) vapors in a 300 ppm EtOH background.

FIG. 27A) Image of initial screen allowing choice of analysis mode. FIG. 27B) Image of screen showing alignment and sizing of image prior to analysis. FIG. 27C) Image of results screen showing RGB values.

FIG. 28A) An example single Phage litmus from which we want the RGB component values. FIG. 28B) iColor user interface and output. In this embodiment, S4 mode (four-color analysis mode) is used. The program delimits 4 equal areas with lengths equal to the total length divided by 4. The program then averages all the RGB component values of every pixel of each area and displays the results onscreen. The brightness of the synthesized image is that of the sample.

FIG. 29A) An example of two Phage litmuses from which we want to compare RGB component values. FIG. 29B) iColor user interface and output. Comparison mode is very similar to the single channel modes, except that instead of having the averages of the different areas, we are displaying the difference between the 8-bit RGB component values of the reference and of the sample. They can go from about −255 to about +255. The synthetic analysis image is the subtracted image. The color is taken from the formula. $R_s = (R_r - R_l)/2 + 128$, where $R_s$, $R_r$, and $R_l$ are the RGB values of the synthetic image, the reference, and the sample respectively. This synthetic image gives a very unique signature for this sample. For example, when the difference is 0, the value would be 128 which would give a neutral grey. The brightness used is the average brightness of the litmus areas. The standard deviations displayed are those of the litmus substrate.

DETAILED DESCRIPTION

Introduction

Figure 1:
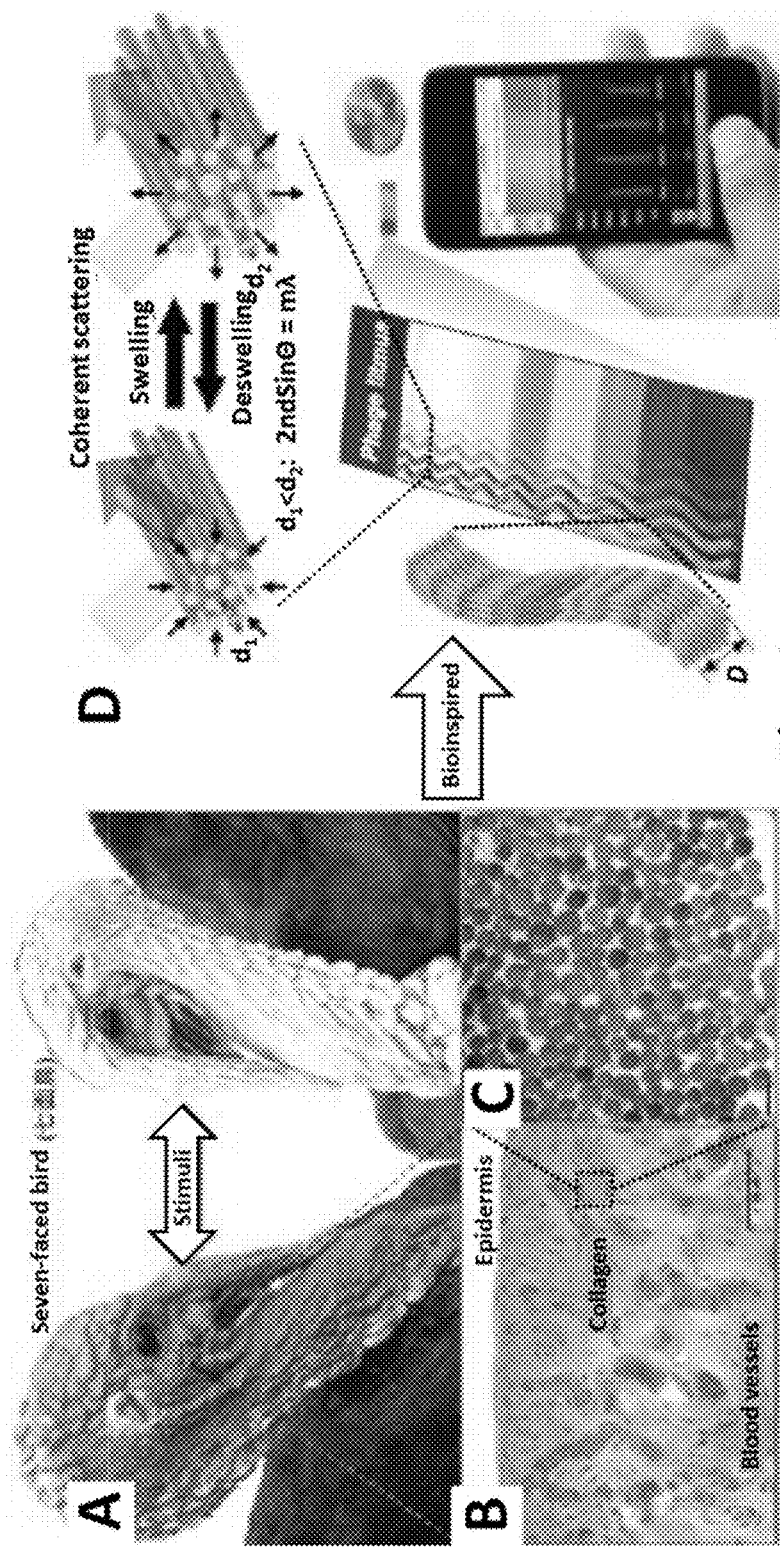
FIG. 1, panels A-D, shows a schematic of a biomimetic colorimetric sensor system. Panel A) Turkeys autonomously change their red skin to white and/or blue when excited. The blue color is associated with structural colorization of collagen nanostructures[11], although their color change mechanism is not known with molecular detail. As a result, turkeys are known as "seven-faced birds" in Korea and Japan. Turkey images published with permission of the photographer, Valerie Burtchett. Panel B) A histological section of turkey skin stained with Masson's trichrome shows that turkey skin consists mainly of collagen and highly vascularized tissues (50 µm scale bar). Panel C) Transmission electron micrograph of perpendicularly aligned collagen bundled fibers in the dermis (200 nm scale bar). Panel D) Bioinspired phage-based colorimetric sensors, termed Phage litmus, are composed of hierarchical bundles like the collagen fibers in turkey skins. Application of analytes of interest (chemical stimuli) causes color shifts due to structural changes, such as bundle spacing ($d_1$ and $d_2$), and coherent scattering. Using a handheld device's camera (iPhone) and a software package of the invention (iColor Analyzer), analytes of interest are detected in a selective and sensitive manner.

There is an increasing demand for assays for detection, quantitative identification, and notification of the presence of chemical, biological, radiological, nuclear, or explosive ("CBRNE") hazards across a broad range of disciplines, including defense, food safety, homeland security, and medical diagnostics, among many others. While there is existing technology for the detection and quantitative identification of chemical and biological hazards, these sensors are generally large, bulky, and/or slow sensor systems that require considerable time and effort to utilize or to move from one location to another. Accordingly, there is a continued need for fast, efficient, and portable sensor systems for hazard detection, as well as for systems that subsequently notify a user of any hazard that is detected.

The biological and chemical agents can be, for example, any biological agent of interest, including but not limited to those used as a biological weapon, including but not limited to numerous bacterium, virus, prion, plant disease, and fungus varieties, as well as biological toxins. Examples of chemical agents of interest include mustard gas, chloride gas, and sarin, among many other examples. Some examples of prime targets for detection by the present system include microorganisms such as *Bacillus anthracis*, members of the genii *Burkholderia, Rickettsia, Shingella, Vibrio*, and *Yersinia pestis*, viruses such as the smallpox virus, and toxic proteins such as ricin (from *Ricinus communis*) and botulinum toxin (from *Clostridum botulinum*), among many other possible biological or chemical agents.

There is similarly an increasing demand for rapid and efficient detection, quantitative identification, and notification of the presence of drugs and other molecular targets, including but not limited to explosives and narcotics, among others.

Detecting the presence of a molecular target and/or a CBRNE hazard or contaminant is only the first step in properly responding to the threat. Notifying the system or user that the hazard has been detected is an important aspect of any CBRNE system, and must function quickly and efficiently without false positives (indicating the presence of the threat to the user or system even though the threat is not present) or false negatives (failing to notify the user or system of the presence of the detected threat). According to some systems, the presence of a CBRNE hazard or contaminant may result in some sort of alarm or other notification system to be initiated, but can often be distanced from the threat or detection event in distance and/or time. In much slower systems, the presence of the CBRNE hazard or contaminant is can only be detected—and therefore reported—in a laboratory setting, thereby resulting in significant time delays in a possible response to the threat. Innovative technologies are therefore required for both the detection and reporting of the presence of CBRNE hazards and contaminants. Innovative technologies are similarly required for both the detection and reporting of the presence of drugs and other molecular targets.

Before the present invention is described, it is to be understood that this invention is not limited to particular embodiments described, as such may, of course, vary. It is also to be understood that the terminology used herein is for the purpose of describing particular embodiments only, and is not intended to be limiting.

Abbreviations

As used herein, "CBRNE", refers to a class of analytes of interest detectable with a device of the invention. The abbreviation "CBRNE" represents chemical, biological, radiological, nuclear and explosive analytes of interest.

Definitions

As used herein and in the appended claims, the singular forms "a", "and", and "the" include plural referents unless the context clearly dictates otherwise. Thus, for example, reference to "a peptide" includes a plurality of such peptides, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a "plurality" of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The use of the terms "binding" or "bind" to describe the interaction between the fiber bundle of the detection layer of the device and the analyte of interest means the association of the analyte of interest and the fiber bundle through such interactions as hydrogen bonding, van der Waals interaction, hydrophobic interaction, pi-pi interaction, physisorption, chemisorption and the like.

"Anchor", "Anchoring", "immobilize" and "immobilized" refers to the interaction between the substrate and the fiber bundle detection layer of the device. The fiber bundles can be immobilized on the substrate by any convenient interaction including, hydrogen bonding, van der Waals interaction, hydrophobic interaction, pi-pi interaction, and the like.

As used herein, "fiber", e.g., "nanofiber", refers to any elongated structure having a nanoscale cross-section such as, but not limited to, nanowires, nanobelts, nanoribbons, or other nanofibrous materials.

"An optically responsive structural change" refers to a change in the device or a component of the device of the invention in which the interaction of the device or component thereof with light is altered between states in which the analyte of interest is bound and unbound to the device or component thereof. An exemplary "optically responsive structural change" is one in which the device or component thereof interacts with different wavelengths of light (e.g., reflects different wavelengths of light) upon binding the analyte of interest. An exemplary "optically responsive structural change" is one in which the detection layer swells upon binding the analyte of interest. An exemplary "optically responsive structural change" is a detectable change observable upon binding the analyte of interest.

As used herein, "explosive" refers to explosive compounds, explosive byproducts, and explosive precursors, unless the context dictates otherwise. Explosives can generally be nitro-based explosives, ammonia and inorganic salt-based explosives, peroxide-based explosives, byproducts thereof, precursors thereof, and mixtures of these explosives. In one aspect, the explosive can be nitro-based and can be selected from the group consisting of trinitrotoluene (TNT); dinitrotoluene (DNT); 2,3-dimethyl-2,3-dinitrobutane (DMNB); 1,3,5-trinitroperhydro-1,3,5-triazine (RDX); pentaerythritol tetranitrate (PETN); octahydro-1,3,5,7-tetranitro-1,3,5,7-tetrazocine (HMX); nitromethane; nitroglycerin; nitrocellulose; ethylene glycol dinitrate; ammonium nitrate; urea nitrate; and the like. RDX and PETN have extremely low vapor pressure which makes them difficult to detect using conventional technologies.

Further exemplary explosives include ammonia or inorganic salt-based such as, but not limited to, ammonia nitrate ($NH_4NO_3$), urea nitrate (($NH_2)_2COHNO_3$), and highly oxidative reagents such as potassium nitrate ($KNO_3$), potassium chlorate ($KClO_3$), and potassium perchlorate ($KClO_4$), dimethyl methylphosphonate, and combinations of these explosives.

Non-limiting examples of peroxide-based explosives can include acetone peroxides; triacetone triperoxide (TATP); peroxyacetone; tri-cyclic acetone peroxide (TCAP); diacetone diperoxide (DADP); hexamethylene triperoxide diamine (HMTD); and composites or combinations thereof. Other explosives and explosive additives can also be detected using a device of the invention.

The term "addressable location" as used herein means a discrete surface area or position on a solid support onto which one or a plurality of fiber bundles form a discrete detectable layer. Exemplary fiber bundles comprise viruses or viral proteins, which are immobilized or absorbed such that exposure of the one or plurality of fiber bundles to a sample comprising an analyte of interest, for a sufficient time, period results in association between the fiber bundle and the analyte of interest in a detectable manner. In some embodiments, the one or plurality of addressable locations of the array is spotted manually by a pipet or automatically by a robotic device.

The terms "association value" as used herein means a single quantitative value that can be used as a criterion for whether a particular sample comprises or does not comprise a particular quantity of an analyte of interest such that, when normalized against a quantitative value calculated for a control sample, the association value can be used to confirm the presence of an analyte of interest and/or to determine the relative degree of contamination in a fluid or on a surface. In an exemplary embodiment, the association value is used in a predictive manner for the diagnosis, prognosis, clinical treatment plan of a subject. In some embodiments, the association value means a single quantitative value. In some embodiments, the quantitative value is calculated by combining quantitative data regarding the association of a substance to one or a plurality of fiber bundles through an interpretation function or algorithm.

The terms "longitudinal axis" refers to an axis of the fiber bundle, e.g., the filamentous molecule, capsid protein running lengthwise of the filamentous material. In the case of phage, for instance, if the phage lengthwise on a z axis (with its side of about 6.6 nm running up the z axis) the longitudinal axis is an axis that runs on through the longest length of the virus or filamentous protein comprising subunits or an axis substantially aligned thereto.

An "array", as that term is used herein, typically refers to an arrangement of entities (in some embodiments, a plurality of fiber bundles) in spatially discrete, generally addressable, locations of substrate with respect to one another, and usually in a format that permits simultaneous exposure of the arranged entities to potential analytes of interest, etc. In some embodiments, an array comprises entities arranged in spatially discrete locations on a substrate. In some embodiments, spatially discrete locations on an array are arranged in a regular pattern with respect to one another (e.g., in a grid or matrix). In some embodiments, the array comprises a confluent layer of a plurality of viruses or viral proteins that are directionally immobilized to the spatially discrete locations on the substrate.

The term "recognition moiety" is used herein to refer to any entity that binds an analyte of interest. In an exemplary embodiment, the recognition moiety selectively binds the analyte of interest, for example, the recognition moiety has a greater affinity for TNT than either DNT or MNT in a mixture of these explosives. In various embodiments, the recognition moiety specifically binds the analyte of interest. Recognition moieties may be of any chemical type. In some embodiments, recognitions moieties are polypeptides or nucleic acid molecules (e.g., aptamers). In some embodiments, recognition moieties are antibodies with a specific affinity for an analyte of interest. In some embodiments, recognitions moieties are carbohydrates.

As is used herein, the term "comparable" is used to refer to two entities that are sufficiently similar to permit comparison, but differing in at least one feature.

"Detector", as this term is used herein, refers to a device operating in tandem with a sensor of the invention to detect a signal event related to a detection mechanism occurring within the detection layer. Detection mechanisms in many existing sensors involves changes in properties such as conductivity, absorbance, luminescence, fluorescence and the like. The difficulty faced by these sensors, however, include the small magnitude of the signal event which can make detection of the signal difficult or affect the selectivity or make the sensor subject to false positive readings. The detection system described herein uses fiber bundles to sense CBRNE threats, hazards, and contaminants, as well as drugs and other small molecules. The fiber bundles can be, for example, virus, polysaccharide, protein or nucleic acid fibers, which are generally known in the art, or virus, polysaccharide, protein or nucleic acid fibers created especially for use in a device/system of the present invention.

In addition to, or as an alternative to, the colorimetric detection/reporter system described herein, an audible or legible detection system can be used to provide notice to a user of the existence of a CBRNE agent or other target. For example, the system can audibly announce the CBRNE agent detected, such as triggering a speaker to say the words "ALERT, TNT DETECTED" when the system detects the explosive trinitrotoluene, or "ALERT, PATHOGEN DETECTED" when the system detects a certain pathogen. According to one embodiment, this audible notification can be the result of detecting the colorimetric described herein, or can be used without the colorimetric component. In addition to audible, legible or colorimetric notification, many other forms of notification that will alert the wearer or user that a CBRNE threat, hazard, or contaminant has been detected by the system are possible. In various embodiments, the concentration of the analyte of interest is detected by the detection system. In various embodiments, the identity and/or concentration and/or physical location of the analyte of interest is communicated to a central hub (e.g., a server) by the system. In an exemplary embodiment, the information collected by the system is transmitted over a social media application (e.g., Twitter, Facebook, etc.).

"Multiplexing", as this term is used herein, refers to detection of two or more analytes of interest at two or more addressable locations on a device of the invention. In various embodiments, the invention provides a multimode platform incorporating multiple sensor materials for selective detection of specific analytes, including explosives and drugs. As such, in one embodiment, a multimode sensor platform can comprise an array of fiber bundles oriented on a substrate in a plurality of detection zones, wherein the individual fiber bundles are separately addressable. Each detection zone can comprise at least one plurality of individual fiber bundles within the array. The fiber bundles can be responsive to association with a corresponding analyte of interest and the detection zone can be colorimetrically responsive to the corresponding analyte of interest.

The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

As used herein, "conservative" amino acid substitutions has the meaning generally recognized in the art. Polypeptides and analogs thereof include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties.

It should be understood that the polypeptides comprising polypeptide sequences a described herein are intended to include polypeptides bearing one or more insertions, deletions, or substitutions, or any combination thereof, of amino acid residues as well as modifications other than insertions, deletions, or substitutions of amino acid residues.

The term "nucleic acid" refers to a molecule comprising two or more linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) can also be used in accordance with some aspects of this invention.

"Sequence homology" or "sequence identity" are used herein interchangeably for nucleotides and amino acids sequences determined using FASTA, BLAST and Gapped BLAST (Altschul et al., Nuc. Acids Res., 1997, 25, 3389, which is incorporated herein by reference in its entirety) and PAUP* 4.0bIO software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol, 1990, 215, 403-410, which is incorporated herein by reference in its entirety). Software for performing BLAST analyses is publicly available through the National Center for Biotechnology Information (http://www.ncbi.nlm.nih.gov). One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" or percentage of sequence identity" can be calculated using PAUP* 4.0bIO software (D. L. Swofford, Sinauer Associates, Massachusetts). The average similarity of the consensus sequence is calculated compared to all sequences in the phylogenic tree.

For the purpose of this disclosure, fiber refers to generally cylindrical structures that may go by different names, including but not limited to, nanofibers, fibrils, nanofibrils, filaments, or nanofilaments. The length, diameter, and aspect ratio (ratio of length over diameter) may vary over a considerable range. Generally, the fibers may be characterized by an aspect ratio of at least 25, at least 50, at least 75, at least 100, or even at least 250, 500, or 1,000 or greater. The diameter of the fibers is typically less than about 20 microns, and more particularly, less than about one micron, including down to about 50 nm, with a minimum diameter of the diameter of the individual virus particles comprising the fibers. The average diameter can be, for example, about 50 nm to about 20 microns, or about 100 nm to about 500 nm. The length of the fibers may vary considerably, but typically will be at least 10 microns and preferably at least 50 microns. The fiber bundles can be macro- or micro- or sub-micro-scale (e.g., nanoscale).

As used herein, the term "sample" refers to any sample obtained or derived from a source of interest, as described herein. In some embodiments, a source of interest comprises an object or a surface of an object, an ambient atmosphere, a liquid, an organism, such as an animal or human. In some embodiments, a biological sample comprises biological tissue or bodily fluid. In some embodiments, a biological sample may be or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, the sample may be a water sample or food sample. In some embodiments, the sample or test sample may be reconstituted in solution after swabbing a surface or food or collecting water or other liquid for detection of contaminants.

EXEMPLARY EMBODIMENTS

Sensors

In an exemplary embodiment, the invention provides a device comprising a detection layer configured to undergo an optically responsive structural change upon interaction with a first analyte of interest. The detection layer is deposited on a substrate, and comprises a first plurality of self-assembled fiber bundles. At least a fraction of the first plurality of fiber bundles undergoes a change from a first conformation to a second conformation upon interaction with the first analyte of interest, thereby undergoing the optically responsive structural change.

In various embodiments, the present invention provides a device comprising a colorimetric detection layer configured to undergo a color change upon interaction with a first analyte of interest. The detection layer comprises a first plurality of self-assembled fiber bundles. At least a fraction of the fiber bundles undergo a change from a first conformation to a second conformation upon interaction with the first analyte of interest, thereby undergoing a color change.

In various embodiments, the invention provides colorimetric sensors in which the detectable layer is immobilized on a substrate. The sensors are readily incorporated in to various systems that enhance the utility of the sensors.

In some embodiments, the device is a sensor comprising at least three surfaces arranged in at least three successive layers, wherein the first surface comprises a substrate area, the second surface comprises one or a plurality of fibrous molecules (e.g., viruses or viral proteins), wherein at least a portion of the one or plurality of viruses or viral proteins or analogs thereof are directionally immobilized to the first surface; and wherein the third surface comprises at least one porous layer or coating in contact with the at least one or plurality of viruses, viral proteins or analogs thereof of the second surface. In some embodiments, at least one of the at least three surfaces is arranged in a planar or substantially planar orientation.

Sensors of the invention can be configured to detect and/or measure one or more of the following types of environmental information: volatile organic chemicals (VOCs), hydrocarbons, polycyclic aromatic hydrocarbons (PAHs), carcinogens, explosives, signatures from chemical weapons, toxins, electromagnetic energy, optical radiation, X-rays, gamma rays, microwave radiation, terahertz radiation, ultraviolet radiation, infrared radiation, radio waves, atomic energy alpha particles, atomic energy beta-particles, climate, humidity, temperature, pressure, barometric pressure, soot density, airborne particle density, airborne particle size, airborne particle shape, airborne particle identity, light intensity, light frequency, light flicker, light phase, ozone, carbon monoxide, carbon dioxide, nitrous oxide, sulfides, airborne pollution, foreign material in the air, viruses, bacteria, allergens, pollen, exhaust from engines, vapors and/or fumes, fuel, signatures for mineral deposits and/or oil deposits.

An exemplary sensor is described herein by reference to the use of a plurality of M13 phage bundles immobilized on a substrate. This focus is for simplicity of illustration of an exemplary embodiment of the invention and should not be construed as limiting the invention.

In an exemplary embodiment, the invention provides a bioinspired phage-based colorimetric sensor, termed Phage litmus, which is composed of hierarchical bundles like the collagen fibers in turkey skins. Application of analytes of interest (chemical stimuli) causes color shifts due to structural changes, such as bundle spacing ($d_1$ and $d_2$), and coherent scattering. Using a handheld device's camera (iPhone) and a software package of the invention (iColor Analyzer), analytes of interest are detected in a selective and sensitive manner. FIG. 1.

An exemplary phage bundle structure of use in the present invention is taught in Example 1, herein. The phage bundle structure comprises a plurality of the recombinant M13 bacteriophages of the present invention are that directionally aligned to each other and made, for example, by a pulling method as taught in Chung, W.-J. et al. Biomimetic self-templating supramolecular structures. *Nature* 478, 364-368, (2011), and U.S. patent application Ser. No. 12/891,699, which are hereby incorporated by reference. In some embodiments, the phage bundle structure is made on or deposited on any suitable substrate that does not interfere in the assembly of the phage bundle structure and the ability of the bacteriophage to bind to the analyte of interest. In some embodiments, the substrate has at least one flat surface on which the phage bundle structure(s) are made or deposited. In some embodiments, the substrate is gold-coated wafer, such as a Si wafer.

To overcome current challenges of color sensors for limitation of diversity of target material, a novel colorimetric sensor using virus (bacteriophage) can be created. The invention provides highly sensitive and selective novel bio-inspired phage based colorimetric sensors, which are made with modifiable custom-built structures and functions through self-assembly and combinatorial screening process of basic building block M13 phage. Through phage display and genetic engineering, any kind of recognition motif can be imparted on the phage of the detection layer, incorporating the specific function of detection of the analyte of interest to the phage based colorimetric sensor. FIGS. 2A-2D.

In an exemplary embodiment, phages genetically engineered to recognize an analyte of interest through directed evolution, replicate to create identical copies and then self-assemble into colored matrices composed of quasi-ordered bundled structures.

In some embodiments, the device is configured such that one or more phage bundle structure, such as on a substrate, are interchangeable. In some embodiments, the device can detect multiple targets at the same time (multiplexing, microarray). In some embodiments, the physical dimension of the device is equal to or smaller than 6×1 mm.

Exemplary devices or colorimetric sensors of the present invention are very sensitive and selective. In some embodiments, the device is portable, its use is rapid, and can be a simple but effective means of detecting various analyte of interest, such as harmful chemical and biological toxins. Thus the device can be used for the purposes of protecting human health and national security.

In an exemplary embodiment, the output of the device of the invention is relatively insensitive to the incident angle of illumination and/or viewing. FIG. 5, FIGS. 6A-6C.

In various embodiments, the switch in the fiber bundles between the first conformation and the second conformation is accompanied by a physical change in the fiber bundles, e.g., an optically responsive structural change, e.g., swelling of the fiber bundle.

In various embodiments, the fiber bundle in the second conformation is swollen with respect to the fiber bundle in said first conformation. The first plurality of self-assembled fiber bundles comprises a filamentous member selected from filamentous viruses, filamentous fungi, filamentous bacteria, filamentous polysaccharides, filamentous polypeptides and a combination thereof. In an exemplary embodiment, the first plurality of self-assembled swellable fiber bundles comprises a filamentous phage virus. In an exemplary embodiment, the first plurality of self-assembled swellable fiber bundles comprises a member selected from filamentous M13 phage, filamentous chitin, filamentous cellulose, filamentous collagen and a combination thereof.

Figure 11A:
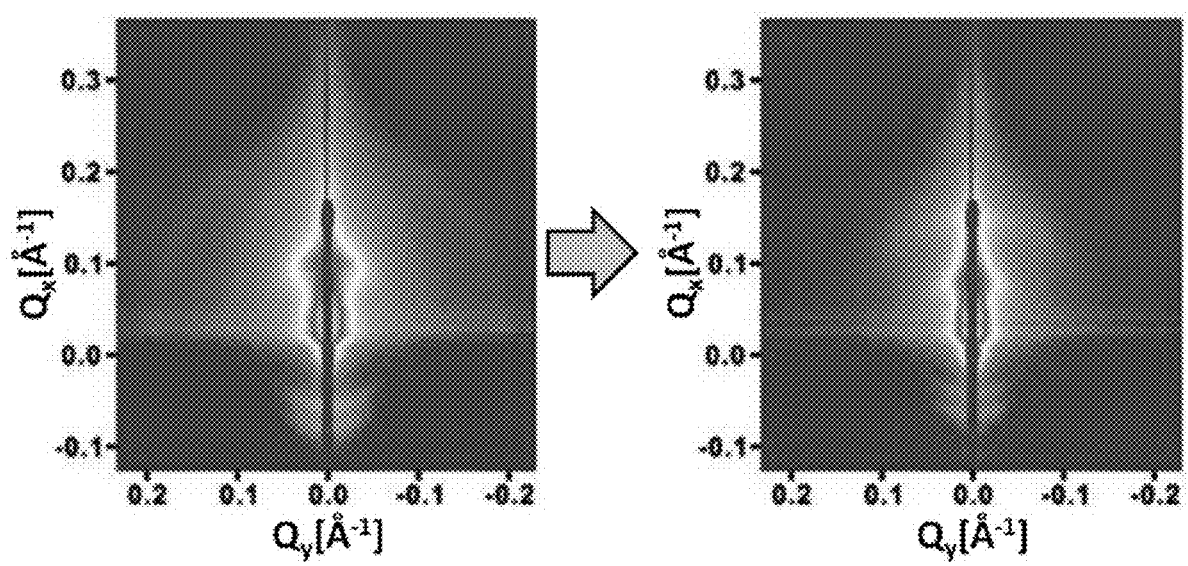
FIGS. 11A-11B illustrate in situ Grazing Incidence Small Angle X-ray Scattering (GISAXS) characterization of the Phage litmus during exposure to humidity.
Figure 11B:
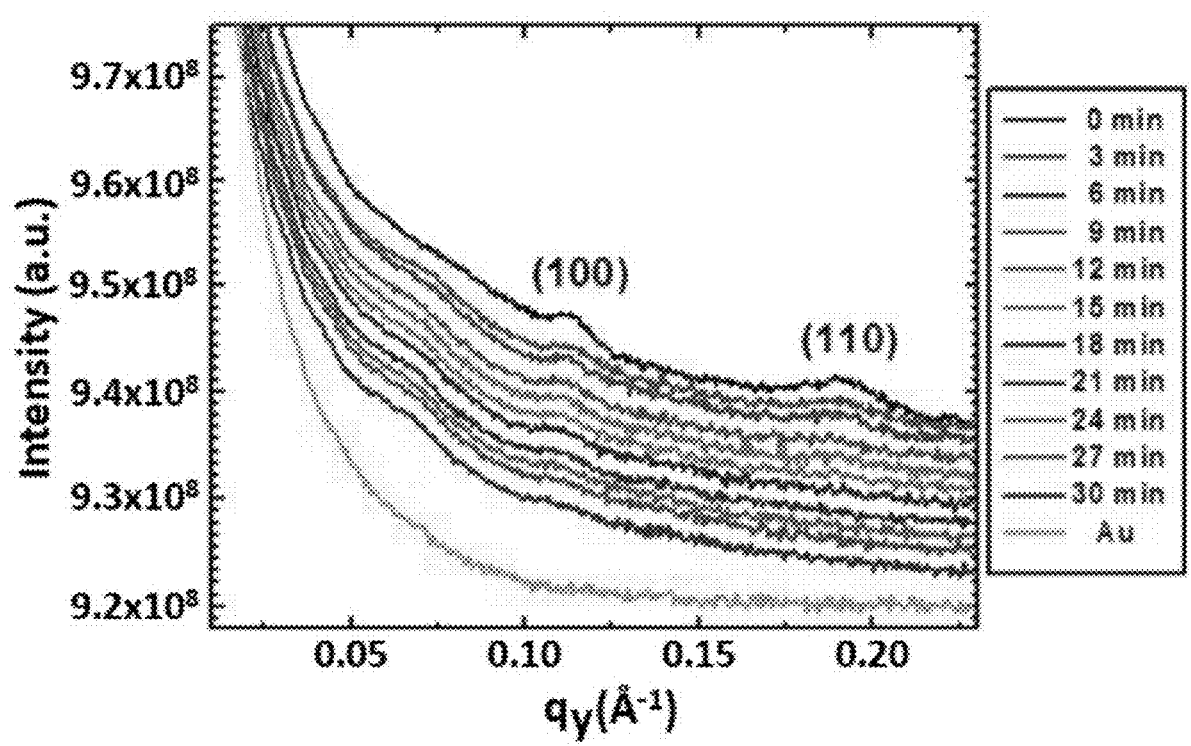
Figure 12:
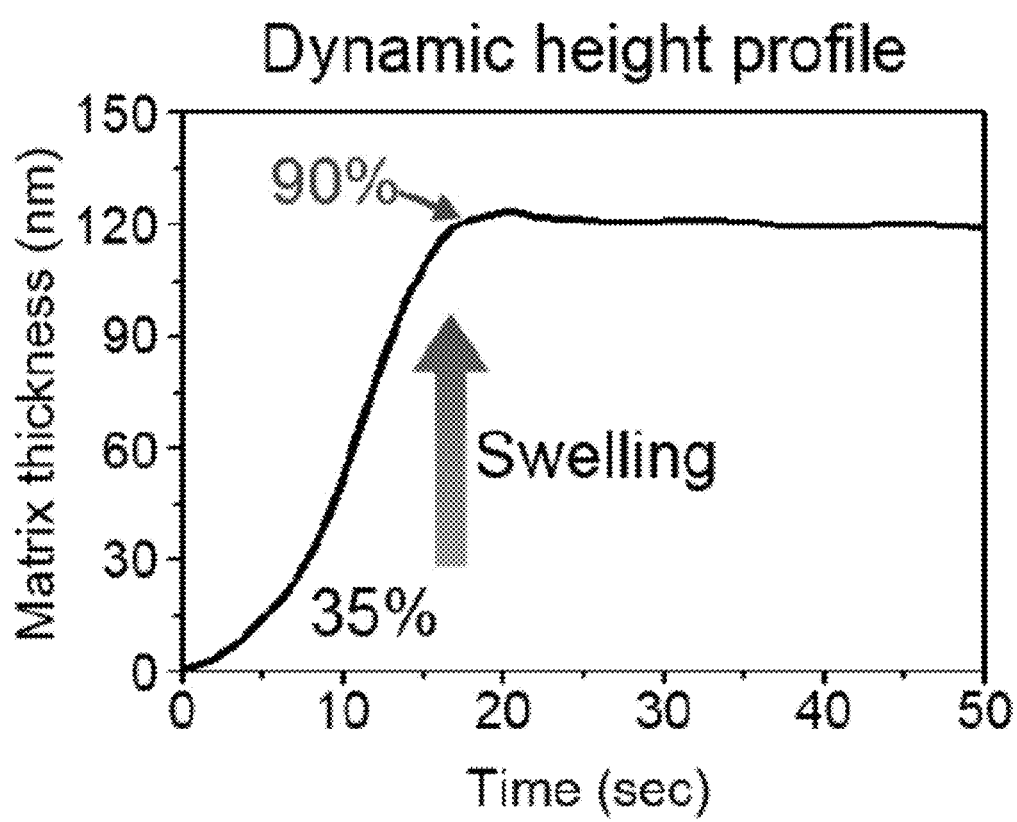
FIG. 12. Dynamic height profile at different humidity levels. The $1^{st}$ band of the Phage litmus swelled within 20 seconds of increasing the relative humidity from 35% to 90%.
Figure 13:
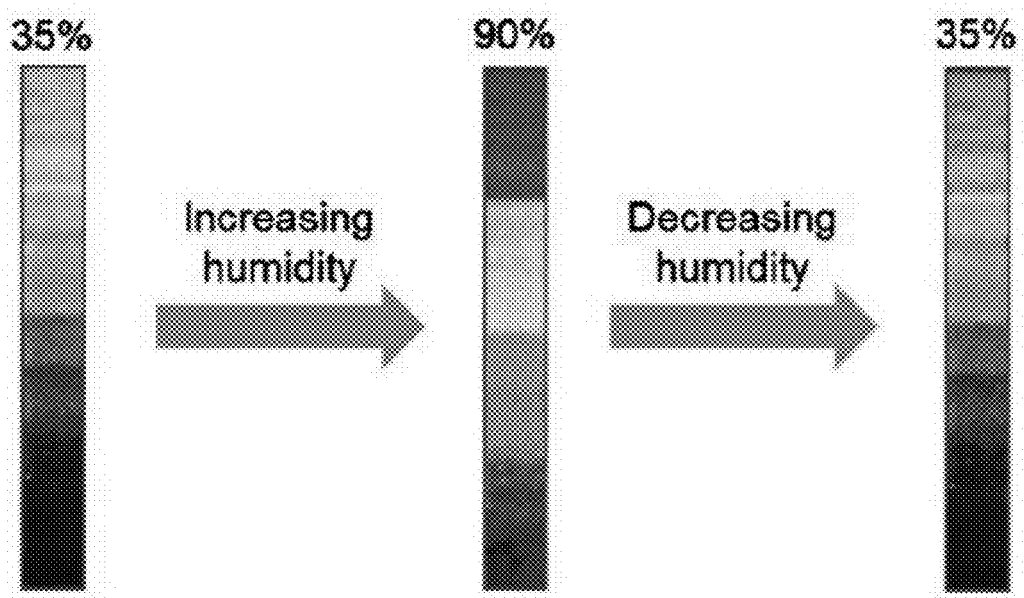
FIG. 13. Reversibility of Phage litmus response to humidity. The color of the Phage litmus could be reversibly changed by relative humidity. At 90% RH, the colors of the Phage litmus red-shifted and after drying to the original RH the color patterns of the Phage litmus sensor returned their original colors. 20 times repeating dynamic DI-water exposure showed good color reproducibility.

In various embodiments, the device of the invention is of use to detect relative humidity. The fiber bundles swell or contract as the humidity in the ambient environment increases or decreases, respectively. FIG. 8A-FIG. 12. In various embodiments, the effect of humidity on the detection layer is reversible. FIG. 13.

Compared with conventional sensors, the device or colorimetric sensor of the present invention can be portable for on-site and/or in-situ analysis. The device or colorimetric sensor of the present invention can possess several advantages over conventional colorimetic sensors: First, the device can be easily fabricated with multiple different colorimetric matrices through one-step self-assembly process by controlling the film growth conditions. Under omni-directional illumination, the device or colorimetric sensor can show very little color difference with viewing angle. Second, the function of the phage matrices can be tailored through directed evolution for a specific analyte of interest. Furthermore, a commonly used handheld device (such as iPhone, Apple Inc., Cupertino, Calif.) can be used to analyze the multi-color recognition patterns quantitatively through interactive data analyses process.

Figure 7A:
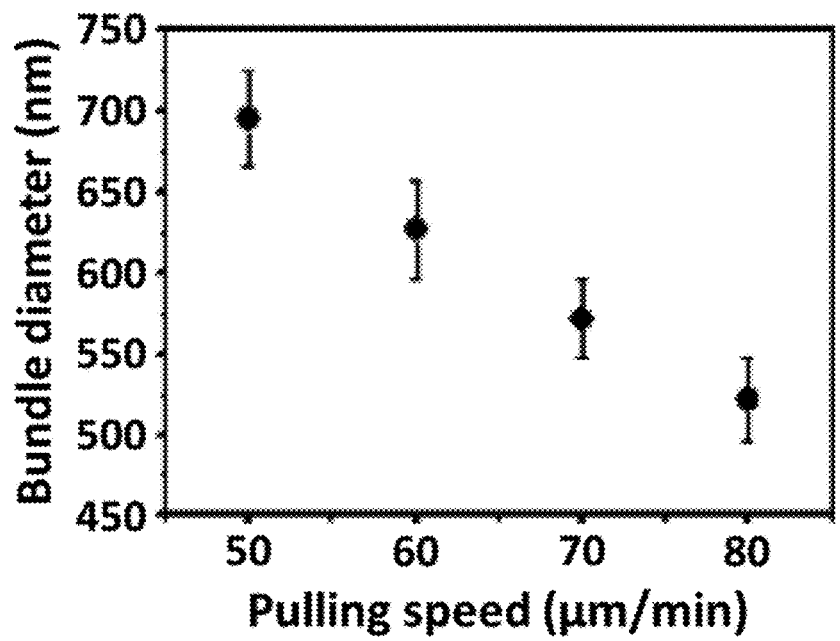
FIGS. 7A-7B illustrate modulation of phage bundle structures by different pulling speeds. The effects of different pulling speeds (50-80 μm/min) on (FIG. 7A) phage bundle diameter and (FIG. 7B) phage litmus matrix thickness. Thickness measurements were made on at least 10 different areas of the phage matrices.
Figure 7B:
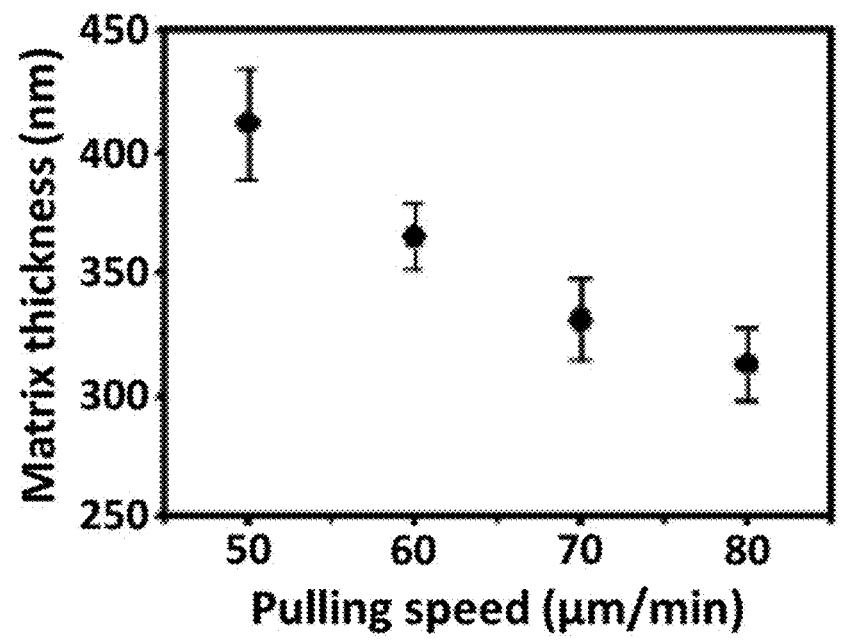
Figure 8A:
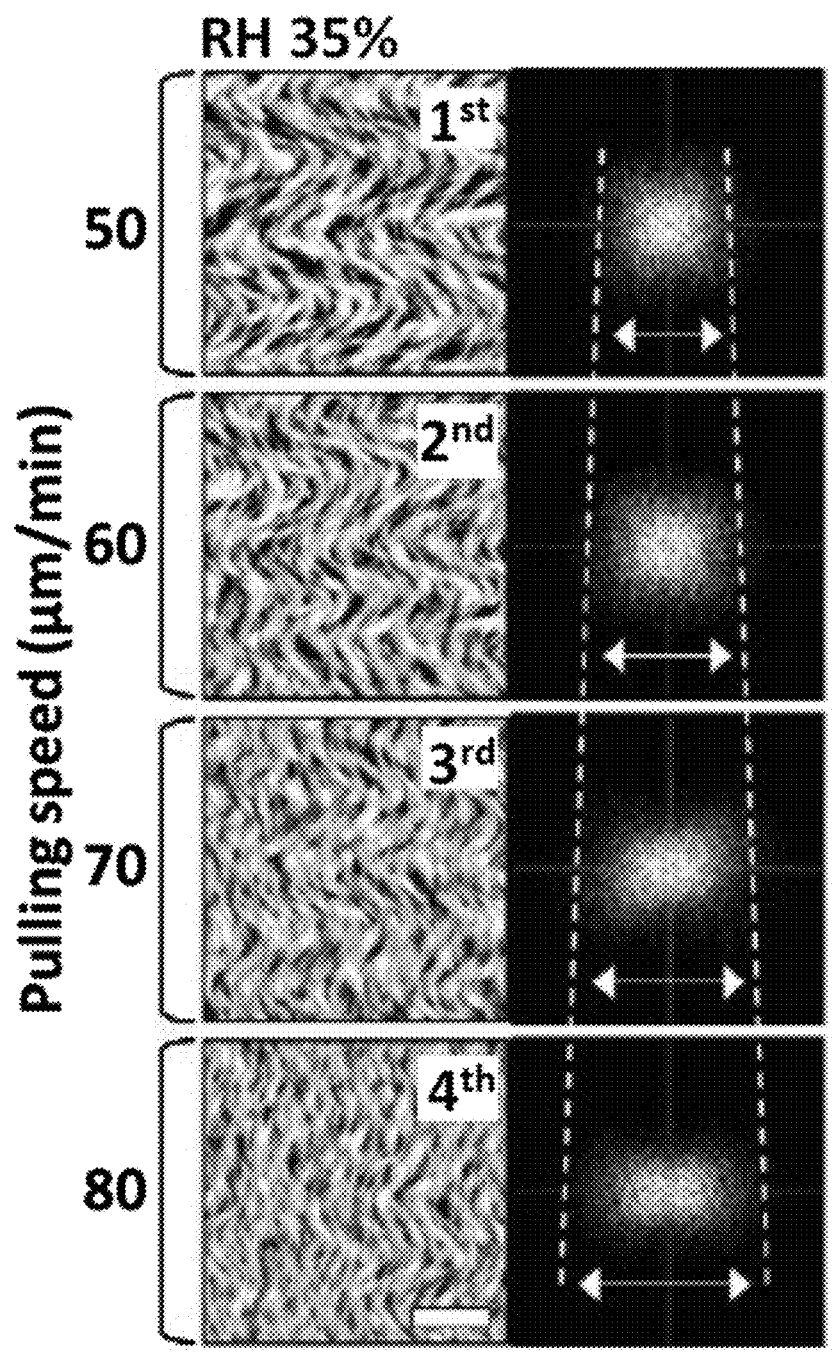
FIGS. 8A-8C show AFM images and two-dimensional fast Fourier transformation (FFT) analysis of quasi-ordered phage bundles at relative humidities (RH) of 35% and 90%, respectively.
Figure 8B:
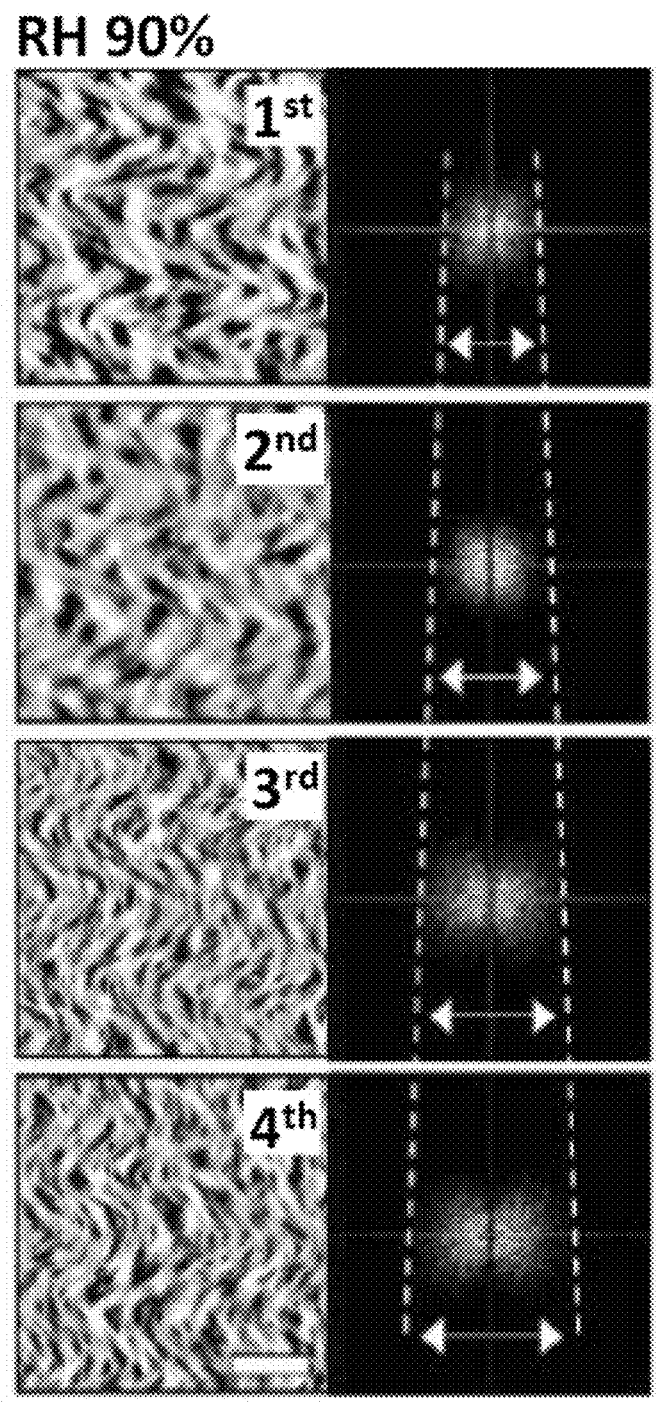
Figure 8C:
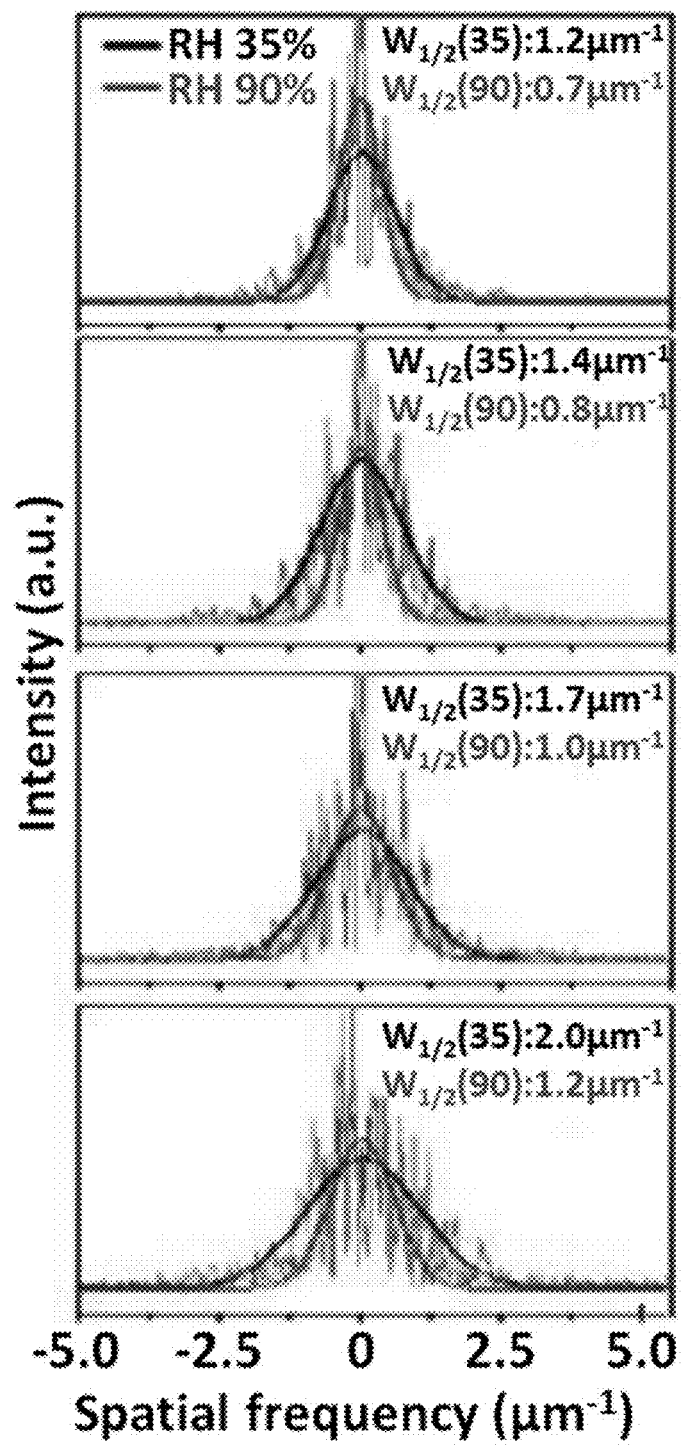

In some embodiments, the device comprises a phage display which comprises unique bacteriophages which can specific bind an analyte of interest. The device can be used to detect a analyte of interest in a selective and sensitive manner. Individual M13 phage is composed of ~2,700 copies of a major coat protein (pVIII) and five copies of minor coat proteins (pIII and pIX) located at either end. Through directed evolution, one skilled in the art can impart recognition receptors on the phage (pVIII part; each phage has ~2,700 of specific recognition receptors) and induce a specific response of the phage. Phage matrices with well-ordered phage-bundled structures are fabricated by vertical pulling substrates from phage solution, whereby competing interfacial forces play a critical role in formation of ordered structures at the air/liquid/solid interfaces. The films produce comprise helical nanofilament bundles aligned parallel to a pulled direction. By controlling the pulling speed, one skilled in the art can modulate phage bundle size which is strongly related to the spacing of the ordered structures (FIGS. 7A-7B). In an exemplary embodiment, a device of the invention is manufactured using a pulling speed of from about 50-80 µm/min.

Because the resulting films are composed of quasi-ordered phage bundles, it can induce coherent scattering of visible light, exhibiting distinct biological structure colors which are not strongly iridescent. The device or phage based colorimetric device is configured to be a sensor which exhibits characteristic color changes depending on the analyte of interest it is exposed it. Furthermore, when the commonly used handheld device can be used to analyze the multi-color recognition patterns through interactive data analyses process, and detect and analyze the analyte of interest. The process is very sensitive and selective over similar chemical structures.

In some embodiments, the device or colorimetric phage sensor possesses multiple advantages over conventional colorimetric sensor, such as easy tailoring of functionality (e.g., through directed evolution) and structure of sensor device, portability, on-site and in-situ analysis using commonly used handheld device, etc. The device can be utilized in a variety of fields (such as organic/inorganic chemical industry, military industry, etc.) for detection of various explosive molecules, various organic compounds, environmental hormone, waste water's BOD, heavy metal, and agricultural pesticides, and the like.

In some embodiments, the present invention has multiple advantages over conventional colorimetric sensors: first, it is easily fabricated with multiple different colorimetric matrices for pattern recognition analysis; second, the function of the phage matrices is tailored through directed evolution based on phage display for detection of any analyte of interest; and, third, it can utilize the commonly used handheld device (e.g., a smart phone, e.g., iPhone, Apple Inc., Cupertino, Calif., Android or MS phone; digital camera and the like) for on-site and/or in-situ analysis.

In some embodiments, the device can quantitatively analyze the color change(s) of the phage based colorimetric sensor in a systematic and convenient manner, for example, using an array of charge-coupled devices (CCD; camera function) of a commonly used handheld device (such as an iPhone; Apple Inc., Cupertino, Calif.) and using an 8-bit RGB mode component to quantify the RGB CCD components using the home-built software (termed iColor analyzer, which is further described herein). Using the iColor analyzer system, one skilled in the art can generate the fingerprint colorimetric sensing profiles of the various organic solvents (such that each analyte of interest or organic solvent has its own unique fingerprint colorimetric sensing profile) and distinguish them in a selective manner. The device or phage based colorimetric sensor coupled with the iColor analyzer can be used as a practical pattern recognition sensor for various kinds of toxic chemicals and biological hazard materials in a sensitive and selective manner.

The Detection Layer

A variety of detectable layer fiber structures can be made from elongated structures. The structures can comprise biomolecules including biomolecular macromolecules and oligomers, including viruses, polypeptides, polysaccharides, and nucleic acids. The structures can comprise naturally occurring materials as well as synthetic materials and genetically engineered materials in blended and composite arrangements. In an exemplary embodiment, these structures comprise a virus.

Exemplary fiber bundles can be formed comprising aligned, crosslinked, rod-like particles as fiber building blocks. Exemplary particles of use in forming fiber bundles have a cross sectional diameter of about 5 nm to about 20 nm, and a length of about 60 nm to about 6,000 nm. More particularly, the length can be about 250 nm to about 1,000 nm. In various embodiments, the particle have a cross sectional diameter in the micrometer range, e.g., at least about 1 µm, 5 µm, 10 µm, 100 µm, 250 µm, or greater.

The material of the fiber bundle is not particularly limited so long as fibers can be prepared. In general, virus particles which are long, filamentous structures can be used. See, e.g., Genetically Engineered Viruses, Christopher Ring (Ed.), Bios Scientific, 2001. Virus particles which can function as flexible rods can be used.

In one embodiment, virus particles are used which are not genetically engineered. However, in general, desirable properties can be achieved when the virus is genetically engineered. In particular, viruses can be used which have been subjected to biopanning so that the virus particles specifically can recognize and bind to materials which were the object of the biopanning. The viruses can be converted to fiber form with or without a conjugate moiety.

Use of filamentous virus in so called directed evolution or biopanning is further described in the patent literature including, for example, U.S. Pat. Nos. 5,223,409 and 5,571,698 to Ladner et al. ("Directed Evolution of Novel Binding Proteins").

The size and dimensions of the virus particle can be such that the particle is elongated. For example, fibrous viral material can be formed comprising aligned, crosslinked, rod-like particles, wherein the viral particles have a cross sectional diameter of about 5 nm to about 20 nm, and a length of about 60 nm to about 6,000 nm. More particularly, the length can be about 250 nm to about 1,000 nm.

Mixtures of two or more different kinds of viruses can be used. Mixtures of virus particles with non-virus materials can be used.

Virus particle can include both an entire virus and portions of a virus including at least the virus capsid. The term virus can refer to both viruses and phages. Entire viruses can include a nucleic acid genome, a capsid, and may optionally include an envelope. Viruses of use in the present invention may further include both native and heterologous amino acid oligomers, such as cell adhesion factors. The nucleic acid genome may be either a native genome or an engineered genome. "Virus particle" further includes portions of viruses comprising at least the capsid.

In general, a virus particle has a native structure, wherein the peptide and nucleic acid portions of the virus are arranged in particular arrangements. In various embodiments, the native structure is preserved when the virus is incorporated into a fiber bundle. The virus and/or nucleic acids may be replicated after being fabricated into a fiber form. If during fiber formation, viral re-infectivity is lost, information may be still stored, programmed, propagated, and addressable through proteins and engineered nucleic acids, including DNA oligomers, in the viral fiber.

Exemplary viruses of use in the detection layer include those including an expressed amino acid oligomer as a specific binding site. Amino acid oligomers can include any sequence of amino acids whether native to a virus or heterologous. Amino acid oligomers may be any length and may include non-amino acid components. Oligomers having about 5 to about 100, and more particularly, about 5 to about 30 amino acid units as specific binding site can be used. Non-amino acid components include, but are not limited to sugars, lipids, drugs, enzymes, or inorganic molecules, including electronic, semiconducting, magnetic, and optical materials.

A wide variety of virus fibers may be used to practice the present invention. The fibers may comprise a plurality of viruses of a single type or a plurality of different types of viruses. Exemplary virus particles comprising of use in the present invention are helical viruses. Examples of helical viruses include, but are not limited to, tobacco mosaic virus (TMV), phage pf1, phage fd1, CTX phage, and phage M13. These viruses are generally rod-shaped and may be rigid or flexible. One of skill in the art may select viruses depending on the intended use and properties of the desired fiber.

In various embodiments, the viruses of use in the present invention are engineered to express one or more peptide sequences including amino acid oligomers on the surface of the viruses. The amino acid oligomers may be native to the virus or heterologous sequences derived from other organisms or engineered to meet specific needs. Expression of amino acid oligomers allows the viruses and fibers comprising the fibers to be engineered to specific applications. For example, the fibers comprising engineered fibers may contain amino acid oligomers that recognize a particular analyte of interest or class of analytes of interest. In various embodiments, the expressed amino acid oligomer binds and detects an organic molecule, such as an explosive or biological warfare agent.

In an exemplary embodiment, the virus expresses a polypeptide that comprises the sequence DDWHWQEQ (SEQ ID NO:2). In various embodiments, the virus expresses a polypeptide sequence that comprises a polypeptide subsequence having at least 90%, at least 92%, at least 94%, at least 96% or at least 98% sequence homology with the polypeptide of SEQ. ID. NO.: 1.

In some embodiments, the genetically engineered bacteriophage is a recombinant M13 bacteriophage comprising one or more recombinant phage coat protein comprising an amino acid sequence capable of binding the analyte of interest. The recombinant phage coat protein is a recombinant pIIII, pIX, or pVIII. The signal peptide is a peptide of any suitable length that does not interfere with the self-assembly of the M13 phage into the phage bundle structure.

The recombinant phages can be made in by the methods taught herein with the appropriate peptide sequence as selected by one skilled in the art. In addition, examples of methods for making the genetically engineered bacteriophage are taught in U.S. patent application Ser. No. 12/891,699, International Patent Application No. PCT/US2009/038449, and U.S. Provisional Application Ser. Nos. 61/039,755 and 60/911,760; all of which are hereby incorporated by reference. Examples of methods for making the genetically engineered bacteriophage or amino acid sequences that bind TNT and/or DNT are taught in U.S. patent application Ser. No. 12/578,428, International Patent Application No. PCT/US2008/060260, and U.S. Provisional Application Ser. Nos. 61/032,770 and 60/911,760; all of which are hereby incorporated by reference.

In some embodiments of the invention, the M13 phage display various peptides that bind a analyte of interest on at least 10%, 20%, 30%, 40%, 50%, 60%, 70%, 80%, 90%, or all 2,700 copies of its major coat proteins.

The M13 phage is a bacterial virus composed of a single-stranded DNA encapsulated by various major and minor coat proteins. It has a long-rod filament shape that is approximately 880 nm long and 6.6 nm wide. Through genetic modification, short peptide signaling molecules (<8 residues) can be displayed on all 2700 copies of the pVIII major coat protein, which covers most of the phage surface (>98%).

The M13 phage has several properties that make it ideal for use in the present invention. M13 phage is non-lytic, producing little cell debris during amplification and simplifying the amplification and purification processes. Therefore, mass amplification of the virus can be easily realized through its infection of E. coli cells, resulting in a monodisperse population of the phage. Due to their monodispersity and long-rod shape, phage have the ability to self-assemble and have been extensively studied as highly organized liquid crystalline systems. The concentration of the viral suspension, ionic strength of the solution, and externally applied force fields are used to modulate viral organization in these systems and have previously been optimized for the construction of one-, two-, and three-dimensional phage-based materials. In addition, through the insertion of random gene sequences into the phage genome, a large combinatorial library can be displayed on the phage major and minor coat proteins.

The large surface area of the recombinant M13 phage of the present invention and its ability to present ligands or analyte of interest in high densities make it useful in the present invention. An engineered M13 phage has the potential for presenting a very high ligand density of ~$1.5 \times 10^{13}$ epitopes/cm$^2$ (3.3 nm radius, 880 nm length, 2700 pVIII units/phage).

A recombinant nucleic acid encoding a recombinant M13 bacteriophage genome can be used to for the replication of the M13, and be a replicon in a suitable microorganism, such as bacterial host cell, such as E. coli. Nucleic acid sequences and methods of maintaining and replicating such replicons are well known to one skilled in the art.

The recombinant phages comprise a short peptide motif of amino acids that is displayed on a coat protein of M13 phage. The coat protein can be pIII, pVIII, and/or pIX. In some embodiments, the peptide is 1-50, 1-25, 1-13, or 1-8 amino acid residues long. One skilled in the art can create partial libraries that contained randomized framing amino acids around the sequence of interest, before could successfully display the desired sequences, that also accommodated phage requirements for replication and packaging by bacteria.

Peptide sequences that bind to TNT and/or DNT are taught in U.S. patent application Ser. No. 12/578,428, International Patent Application No. PCT/US2008/060260, and U.S. Provisional Application Ser. Nos. 61/032,770 and 60/911,760; all of which are hereby incorporated by reference.

A number of prior art references teach the engineering of viruses to express amino acid oligomers and may be used to assist in practicing the present invention. For example, U.S. Pat. No. 5,403,484 by Ladner et al discloses the selection and expression of heterologous binding domains on the surface of viruses. U.S. Pat. No. 5,766,905 by Studier et al discloses a display vector comprising DNA encoding at least a portion of capsid protein followed by a cloning site for insertion of a foreign DNA sequence. The compositions described are useful in producing a virus displaying a protein or peptide of interest. U.S. Pat. No. 5,885,808 by Spooner et al discloses an adenovirus and method of modifying an adenovirus with a modified cell-binding moiety. U.S. Pat. No. 6,261,554 by Valerio et al shows an engineered gene delivery vehicle comprising a gene of interest and a viral capsid or envelope carrying a member of a specific binding pair. U.S. Published Patent Application 2001/0019820 by Li shows viruses engineered to express ligands on their surfaces for the detection of molecules, such as polypeptides, cells, receptors, and channel proteins.

Conjugates

In the present invention, the virus can be conjugated with a conjugate material altering the properties of the virus, e.g., having an affinity for an analyte of interest, or mineralizing the virus. The conjugate material is not particularly limited. In general, it will be selected for a particular application. The conjugate material can be conjugated to the virus particles by being subjected to viral biopanning against the conjugate material, and then the conjugate material is specifically bound to the virus particle by, for example, a surface treatment. Conjugate material can be preformed and then bound to the virus or it can be directly formed or nucleated on the virus. The virus can act as a catalyst for formation of or biomineralization of the conjugate material on the virus.

Examples of general types of conjugate materials include protein, peptide, nucleic acid, DNA, RNA, oligonucleotide, drugs, enzymes. Conjugate molecules can be inorganic, organic, particulate, nanoparticulate, small molecule, single crystalline, polycrystalline, amorphous, metallic, magnetic, semiconductor, polymeric, block copolymer, functional polymer, conducting polymeric, light-emitting, phosphorescent, organic magnet, chromophore, and fluorescent materials.

The conjugate material can be directly bound to the virus, or can be linked to the virus by an intermediate linking moiety which can both bind to the virus and the conjugate material.

Analytes of Interest

The intended analyte of interest binding to a detection layer in a detectable manner may be a combination of different but related molecules, such as analogs. In some embodiments of the invention, the analyte of interest is a small organic compound. Typically the small organic compound has a molecular weight of no more than 1,000 daltons. In some embodiments, the small compound has a molecular weight of no more than 500 daltons. In certain embodiments, the small compound has a molecular weight of no more than 250 daltons. In some embodiments, the small compound has a molecular weight of at least 50, 100, 150, or 200 daltons. In various embodiments, the small organic compound has as molecular weight of less than 50 daltons. In some embodiments, the analyte of interest is in the gaseous phase when it binds to the fiber bundle, e.g., genetically engineered bacteriophage. In an exemplary embodiment, the analyte is not a small molecule, but is an oligomer or polymer, e.g., a nucleic acid (e.g., DNA, RNA), a peptide, a saccharide, or a synthetic oligomer or polymer. In various embodiments, the oligomer or polymer is associated with a virus or other infectious agent (e.g., smallpox, anthrax). Exemplary oligomers and polymers of interest include those associated with biological agents of war, particularly weaponized biological agents of war.

In certain embodiments the small organic compound is a substituted benzene derivative. Substituted benzene derivatives comprise at least one alkyl or one nitro functional groups. The alkyl functional group can be a methyl. In some embodiments, the substituted benzene derivative is a nitroaromatic compound comprising at least one nitro functional group. Nitroaromatic compounds include, without limitation, 2,4,6-trinitrotoluene (TNT), 2,4-dinitrotoluene (DNT), 2,4,6-trinitrobenzene (TNB), nitrobenzene, methylnitrobenzenes, methyldinitrobenzenes, methyltrinitrobenzene, ethylnitrobenzenes, ethyldinitrobenzenes, ethyltrinitrobenzene, dinitrobenzenes, trinitrobenzene, nitrotoluenes, dinitrotoluenes, nitroxylene, dinitroxylene, trinitroxylene, and nitrostyrene.

Figure 21:
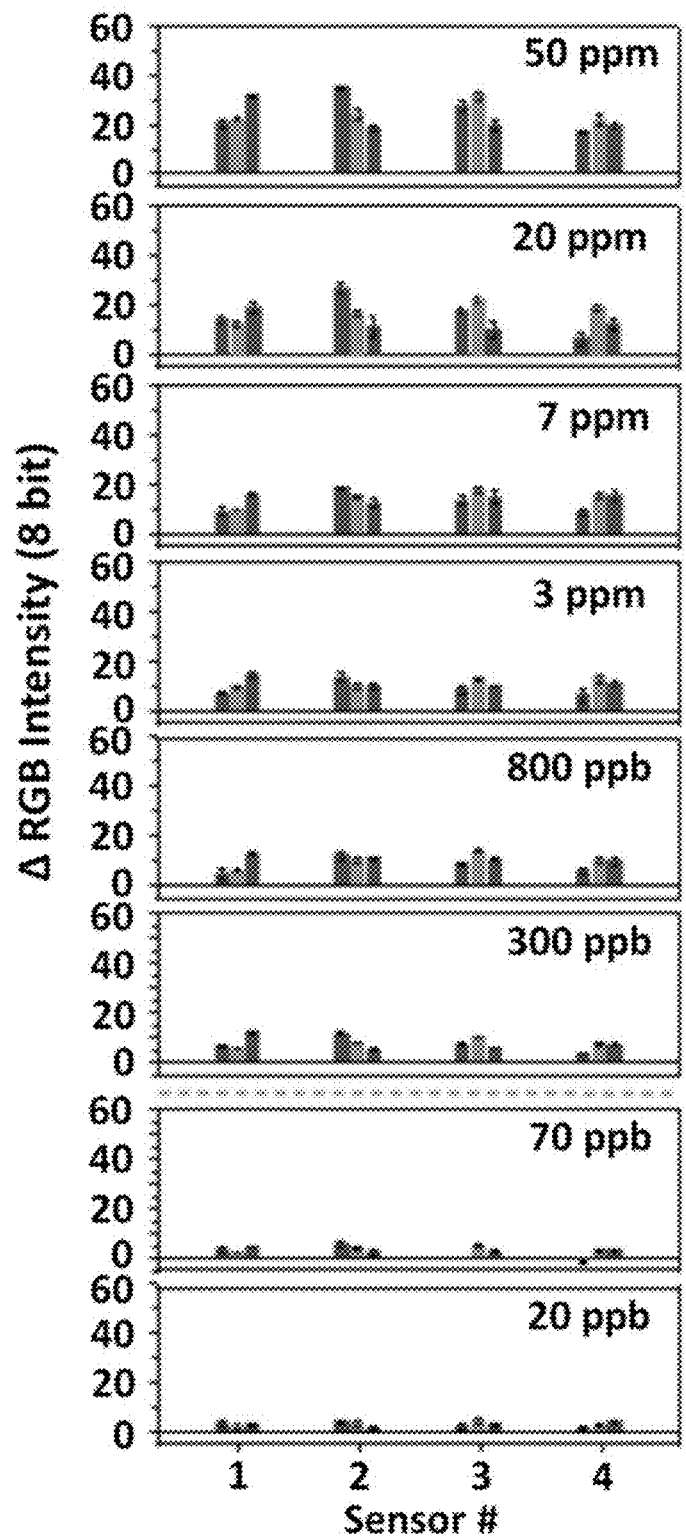
FIG. 21. RGB color patterns of the TNT-Phage litmus sensor in response to different TNT concentrations. The difference in RGB color intensity was decreased as TNT concentration decreased. In the gas phase, the TNT concentrations in the ppb range can be measured, for example, TNT was effectively analyzed using the iColor device at a concentration of 300 ppb. The dashed redline indicates the sensitivity limit of the TNT-Phage litmus against TNT in a gas phase.

In an exemplary embodiment, the invention provides a sensor that selectively detects TNT. In various embodiments, the sensor of the invention selectively detects the presence of TNT in the presence of one or more of DMT and MNT. FIG. 1, FIGS. 17-20D, FIGS. 24A-24C. In various embodiments, the response of the sensor of the invention is concentration dependent with respect to the concentration of TNT. FIG. 21.

Figure 14:
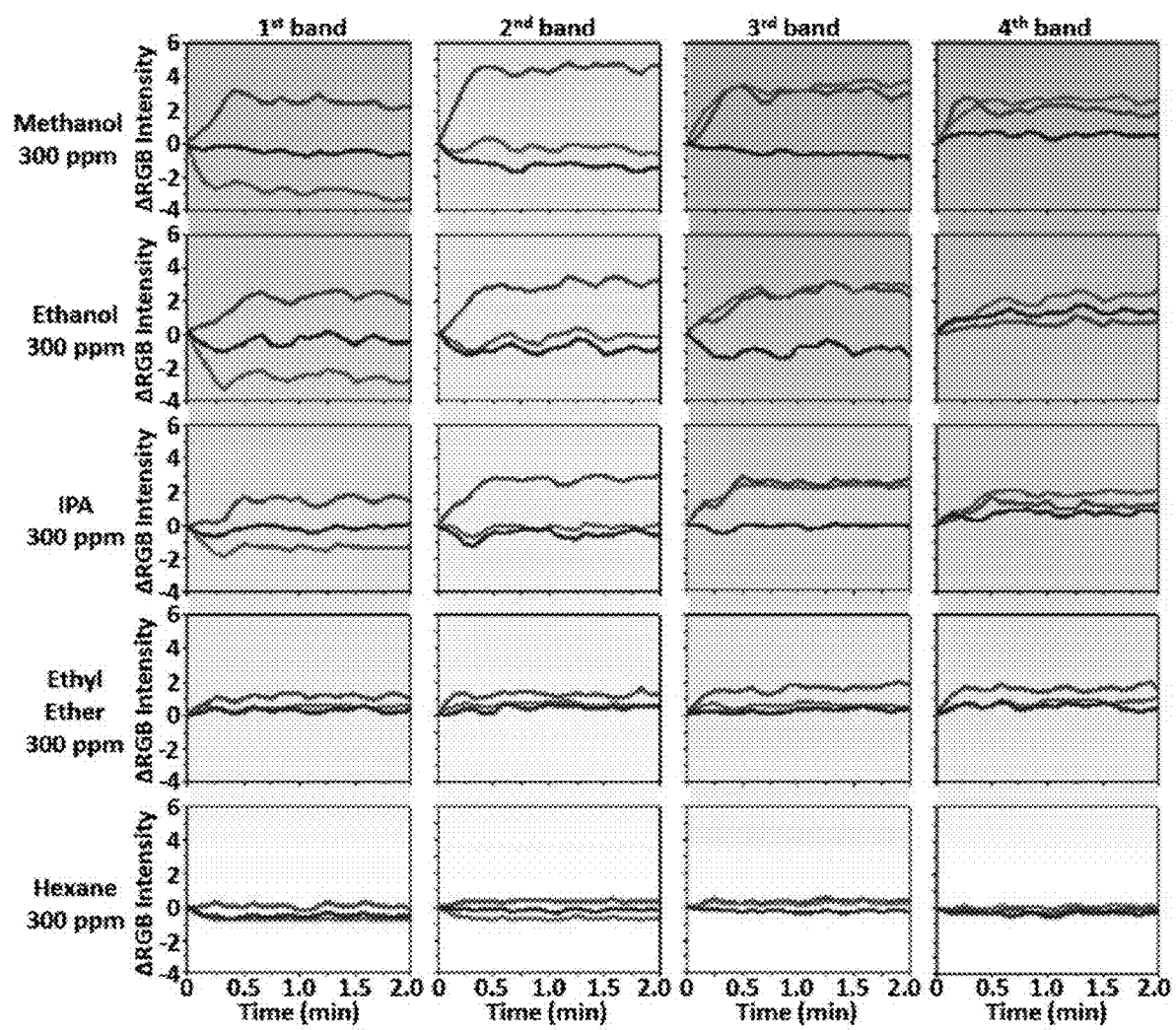
FIG. 14. Real time RGB color component analysis of Phage litmus upon exposure of methanol (MeOH), ethanol (EtOH), isopropyl alcohol (IPA), diethyl ether (Ether), and n-hexane (Hexane). All color matrices in the Phage litmus responded to target chemicals simultaneously in 30 seconds.
Figure 15:
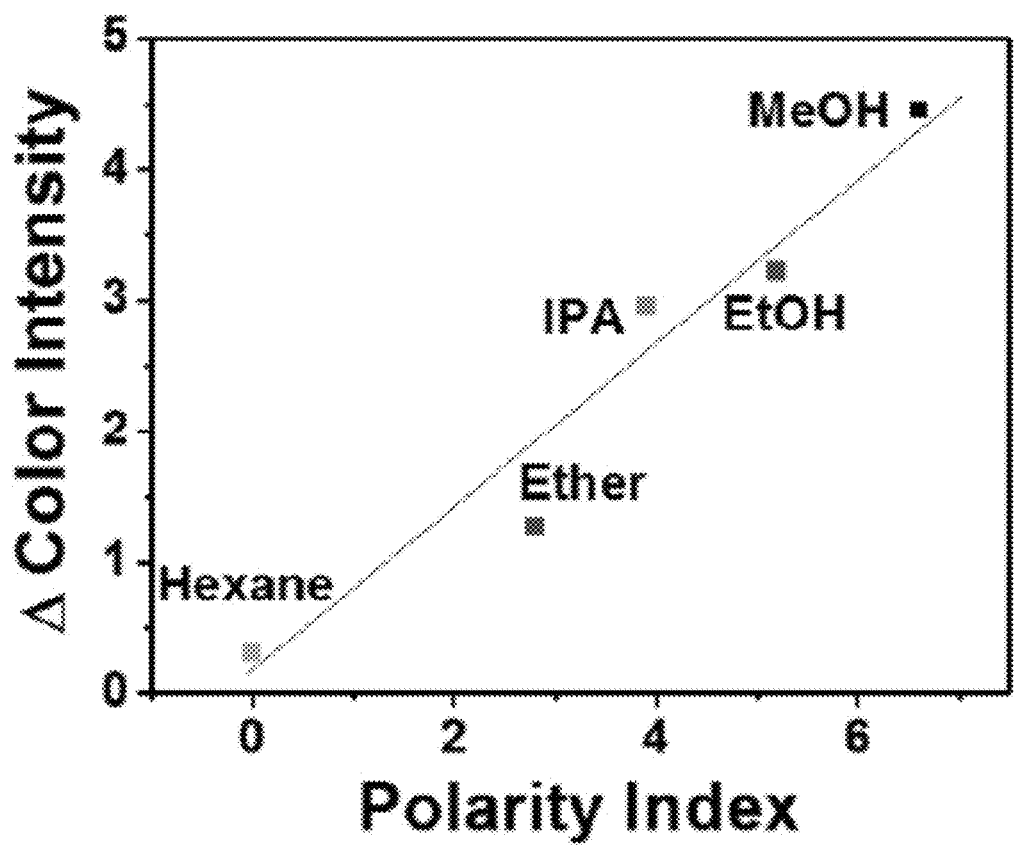
FIG. 15. Correlation between the response magnitude of Phage litmus and the polarity index of volatile organic compounds (VOCs). The Phage litmus response increased with increasing VOC polarity.
Figure 16:
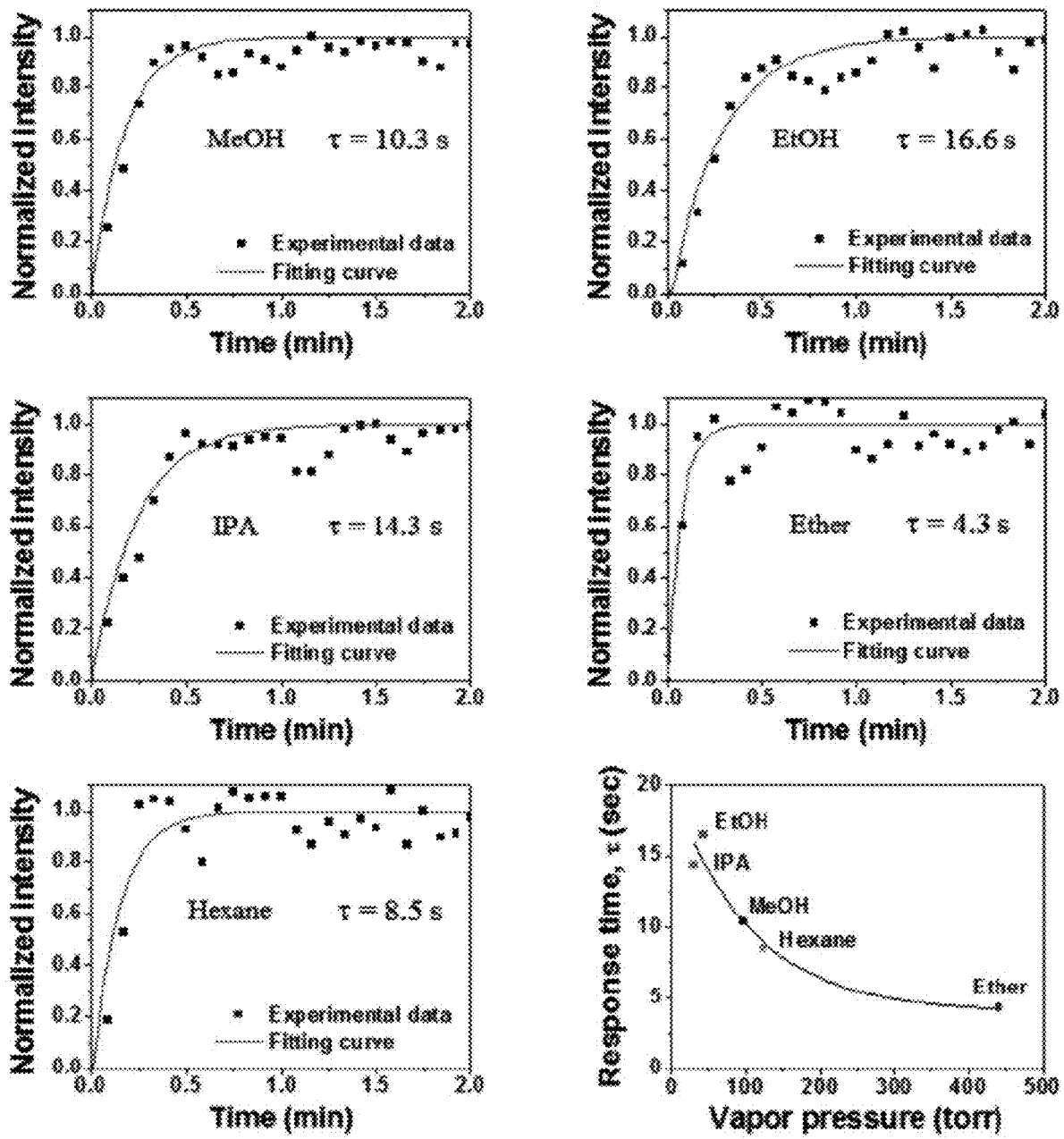
FIG. 16. The effect of volatile organic compound (VOC) vapor pressure on Phage litmus response. The response time of Phage litmus decreased with increasing VOC vapor pressures. The time constants, τ were calculated by fitting the evolution of the growth of the color intensity, i(t), with the following exponential function. $i(t)=a\{1-\exp(-t/\tau)\}$.
Figure 17A:
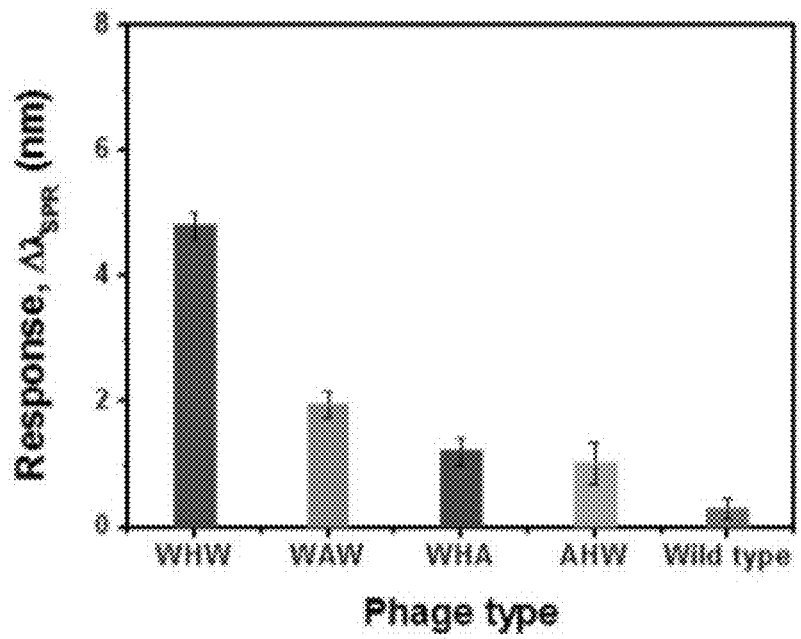
FIGS. 17A-17B illustrate comparative binding assays of TNT-binding phage (WHW). To confirm the specific multivalent interaction between TNT-binding phage and TNT, a binding assay experiment was performed against TNT-binding-phage, alanine-substituted phages and wild type phage using an SPR technique.
Figure 17B:
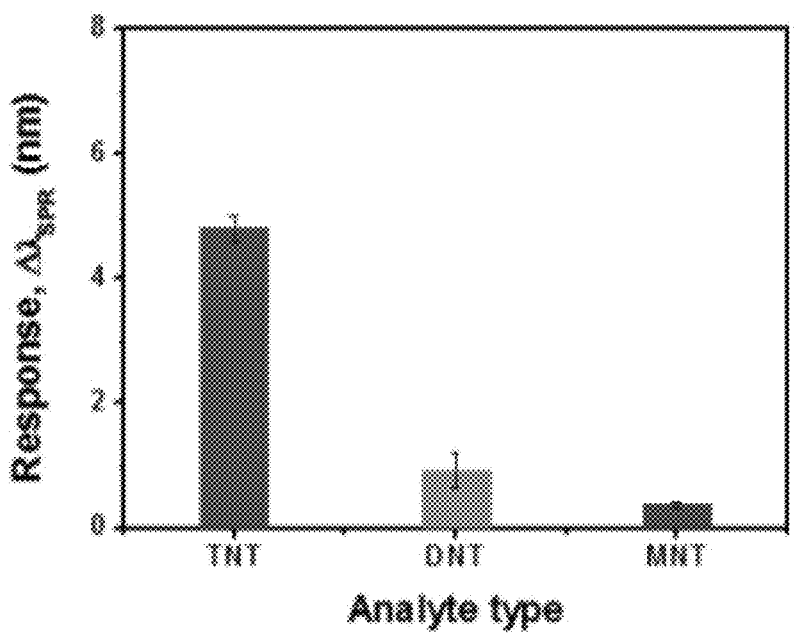
Figure 18A:
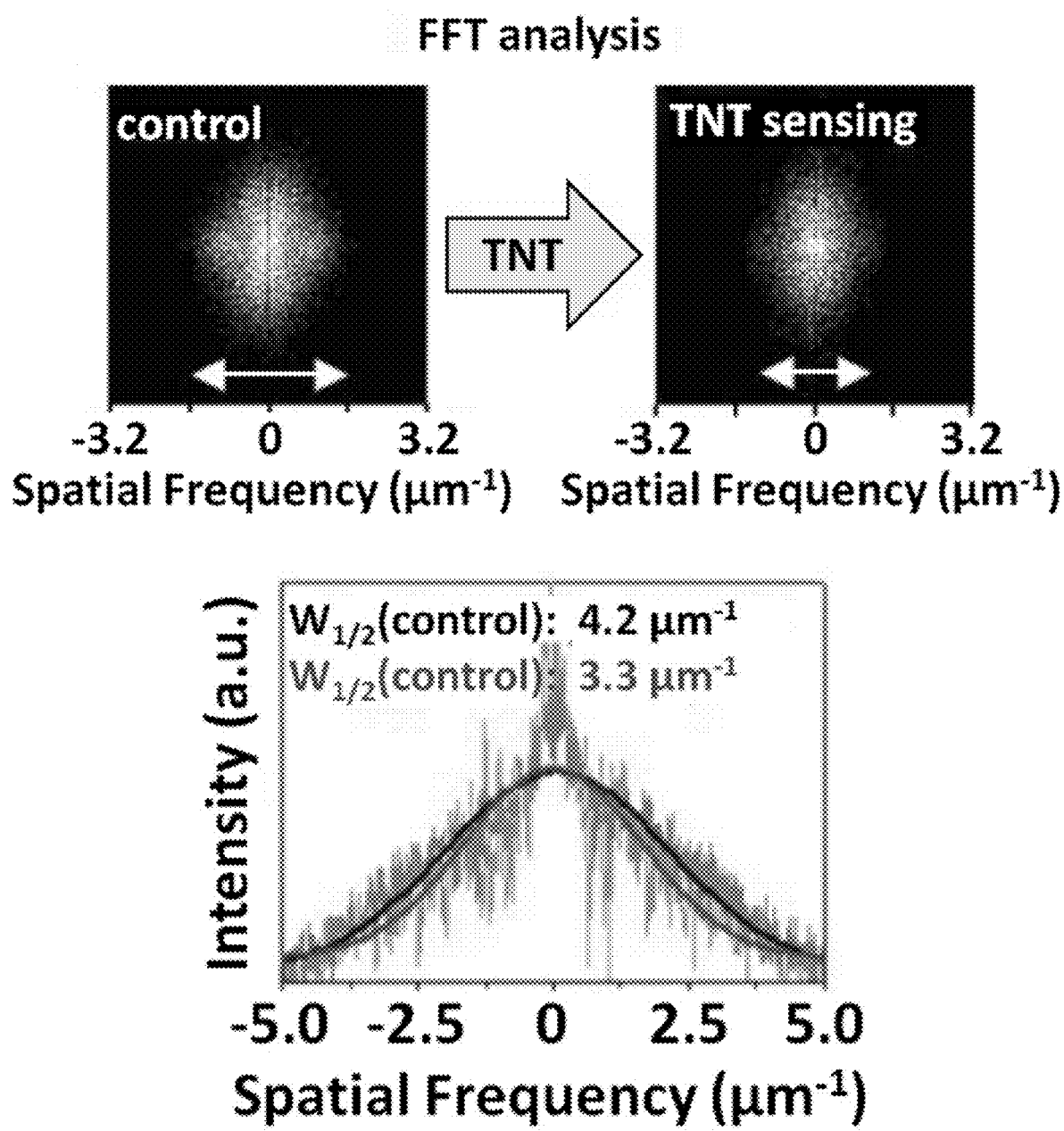
FIGS. 18A-18B illustrate TNT-Phage litmus structure modulation by TNT binding.
Figure 18B:
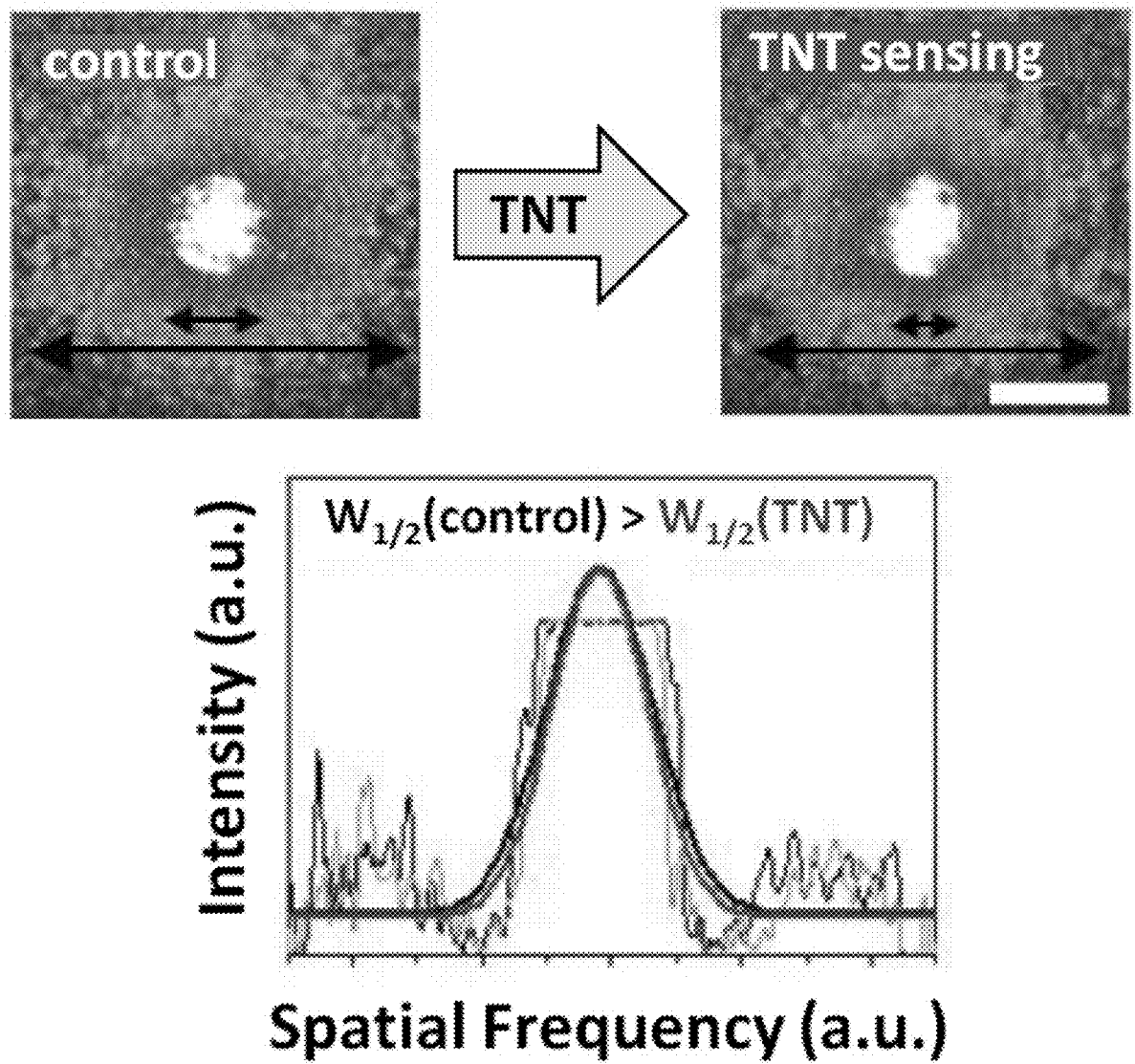

In various embodiments, the small organic molecule is a volatile organic compound (VOC), e.g., a solvent. Exemplary VOCs include aromatic hydrocarbons, chlorocarbons, fluorocarbons, chlorofluorocarbons, and formaldehyde. FIG. 14-FIG. 16.

In some embodiments, the analyte of interest is not particularly volatile, or is essentially non-volatile at standard temperature and pressure.

In some embodiments, the small organic compound has a vapor pressure ranging from about $1\times10^{-9}$ to about $1\times10^{-6}$. In certain embodiments, the small organic compound has a vapor pressure ranging from about $4\times10^{-9}$ to about $4\times10^{-7}$.

In some embodiments, the invention provides explosives detection sensors capable of detecting an explosive material with a moderate to high vapor pressure. Conventional detectors can typically detect (with varying levels of sensitivity) higher vapor pressure explosive materials, because the material is present, at least in part, in the air/atmosphere that has been exposed to the solid material. In some embodiments, the explosives detection device of the present teachings are also capable of detecting an explosive material with a low vapor pressure.

In various embodiments, the invention provides a device capable of detecting low vapor pressure explosives. Detecting low vapor pressure explosive materials is generally difficult, because a solid sample leaves very little trace of the material in the air/atmosphere. As used herein, a material having "low vapor pressure" refers to a material with a vapor pressure of less than about $1\times10^{-5}$ Torr at room temperature/atmospheric pressure. As used herein, a material having "moderate to high vapor pressure" refers to a material with a vapor pressure of greater than about $1\times10^{-5}$ Torr at room temperature/atmospheric pressure.

Vapor pressure can also be denoted by the concentration of particles present in the air/atmosphere around the material. Accordingly, as used herein, "low vapor pressure" material can also refer to a material with a vapor pressure of less than about 10 ppb at room temperature/atmospheric pressure and "moderate to high vapor pressure" material can also refer to a material with a vapor pressure of greater than about 10 ppb at room temperature/atmospheric pressure.

In some embodiments, the explosives detection device of the present invention is capable of detecting an explosive material with a vapor pressure of less than about $1\times10^{-6}$ Torr at room temperature/atmospheric pressure. In some embodiments, the explosives detection device of the present invention is capable of detecting an explosive material with a vapor pressure of less than about $1\times10^{-7}$ Torr at room temperature/atmospheric pressure. In some embodiments, the explosives detection device of the present invention is capable of detecting an explosive material with a vapor pressure of less than about $1\times10^{-8}$ Torr, less than about $1\times10^{-9}$ Torr, or less than about $1\times10^{-10}$ Torr at room temperature/atmospheric pressure. Vapor pressures of certain explosives materials may be found, for example, in Moore, D. S., *Rev. Sci. Instrum.* 75 (8): 2499-2512, 2004.

Explosive materials with a low vapor pressure include, but are not limited to, octahydro-1,3,5,7-tetranitro-1,3,5,7-tetrazocine (HMX), hexahydro-1,3,5-trinitro-1,3,5-triazine (RDX), ammonium perchlorate (AP), methyl-2,4,6-trinitrophenylnitramine (Tetryl), picric acid (PA), hexanitrostilbene (HNS) and pentaerythritol tetranitrate (PETN), 1,3,5-trinitrobenzene (TNB), 1,3-dinitrobenzene (DNB), methyl-2,4, 6-trinitrophenylnitramine (Tetryl), nitrobenzene (NB), 2,4, 6-trinitrotoluene (TNT), 2,4-dinitrotoluene (2,4DNT), 2,6-dinitrotoluene (2,6DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), and 2,3-dimethyl-2,3-dinitrobutane (DMNB).

In some embodiments, the device or method of the invention is capable of detecting an explosive material in an amount less than about 1 ppb. In some embodiments, the device or method is capable of detecting an explosive material in an amount less than about 0.01 ppb. The explosive material is detectable as a gas or in an air or liquid solution.

In some embodiments, the present teachings provide a highly sensitive sensor device. Accordingly, in some embodiments, the device is capable of detecting an explosive material in very small amounts. In some embodiments, the substrate is capable of detecting the presence of explosive material in a vapor at concentrations as low as about 200 ppb. In some embodiments, the substrate is capable of detecting the presence of explosive material in a vapor at concentrations as low as about 150 ppb. In some embodiments, the substrate is capable of detecting the presence of explosive material in a vapor at concentrations as low as about 100 ppb, as low as about 75 ppb, as low as about 50 ppb, as low as about 25 ppb, as low as about 10 ppb, as low as about 5 ppb, as low as about 1 ppb, as low as about 0.5 ppb, as low as about 0.1 ppb, as low as about 0.01 ppb, or even as low as about 0.001 ppb. In some embodiments, the substrate is capable of detecting the presence of explosive material in a vapor at concentrations as low as about 1 ppt, as low as about 0.5 ppt, as low as about 0.1 ppt, or even as low as about 0.01 ppt. In some embodiments, explosive material in a vapor at concentrations as low as about 250 ppb can be visualized by viewing the sensor with the naked eye. In some embodiments, explosive material in a vapor at concentrations as low as about 100 ppb can be visualized by viewing the sensor with the naked eye. In some embodiments, explosive material in a vapor at concentrations as low as about 50 ppb can be visualized by viewing the sensor with the naked eye.

In some cases, sensitivity of the detection layer and, therefore the device, is measured by the amount (in weight) of explosive material required to produce a detectable color change in the detection layer of a device of the invention. In some embodiments, the substrate is capable of producing detectable color change in the presence of an explosive material in an amount less than about 1 µg, less than about 500 ng, less than about 250 ng, less than about 100 ng, less than about 50 ng, or less than about 25 ng. In some embodiments, the substrate is capable of producing detectable color change in the presence of an explosive material in an amount less than about 10 ng. In some embodiments, the substrate is capable of producing detectable color change in the presence of an explosive material in an amount less than about 5 ng. In some embodiments, the substrate is capable of producing detectable color change in the presence of an explosive material in an amount less than about 1 ng, less than about 0.1 ng or less than about 0.01 ng.

In some embodiments, the present teachings provide a device that allows for quick detection of explosive materials. In some embodiments, for example, the device is capable of detecting an explosive material in less than about 6 minutes. In some embodiments the device is capable of detecting an explosive material in less than about 5 minutes. In some embodiments the device is capable of detecting an explosive material in less than about 4 minutes. In some embodiments the device is capable of detecting an explosive material in less than about 3 minutes, less than about 2 minutes, less than about 1 minute, less than about 30 seconds, less than about 20 seconds, or less than about 10 seconds. In some embodiments the device is capable of detecting an explosive material in less than about 5 seconds. The time of detection can vary within the parameters above, but will generally depend upon the concentration of explosive material exposed to the substrate.

The focus of the preceding discussion on explosives is purely for purposes of illustration. As set forth herein and as will be apparent to those of skill in the art, the detection layer and devices of the invention are of use to detect a wide range of analytes of interest. In some embodiments, the analyte of interest is a toxic compound, explosive a carcinogenic compound, an insecticide compound, or the like. In some embodiments, the analyte of interest is an organohalogen compound, such as an organobromine compound, organochlorine compound, organofluorine compound, organoiodine compound, or the like. In some embodiments, the organobromine compound is a polybrominated diphenyl ether (PBDE), bromomethane, or the like.

Substrates

Substrates that are useful in practicing the present invention can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semi-conductors. Further the substrates can be substantially impermeable to liquids, vapors and/or gases or, alternatively, the substrates can be permeable to one or more of these classes of materials.

Exemplary substrate materials include, but are not limited to, inorganic crystals, inorganic glasses, inorganic oxides, metals, organic polymers and combinations thereof.

Inorganic Crystal and Glasses

Inorganic crystals and inorganic glasses that are appropriate for substrate materials include, for example, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, C. H. L., Crystal Growth Theory and Techniques, Plenum Press, New York 1974. Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

Inorganic Oxides

Inorganic oxides can also form a substrate of the device of the present invention. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In an exemplary embodiment, the substrate is a rigid structure that is impermeable to liquids and gases. In this embodiment, the substrate consists of a glass plate onto which a metal, such as gold is layered, e.g., by evaporative deposition.

Metals

Metals are also of use as substrates in the present invention. The metal can be used as a crystal, a sheet or a powder. The metal can be deposited onto a backing by any method known to those of skill in the art including, but not limited to, evaporative deposition, sputtering and electroless deposition.

Any metal that is chemically inert towards the detection layer will be useful as a substrate in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

Organic Polymers

Organic polymers are a useful class of substrate materials. Organic polymers useful as substrates in the present invention include polymers which are permeable to gases, liquids and molecules in solution. Other useful polymers are those which are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins. See, Cognard, J. ALIGNMENT OF NEMATIC LIQUID CRYSTALS AND THEIR MIXTURES, in Mol. Cryst. Liq. Cryst. 1:1-74 (1982). Presently preferred organic polymers include polydimethylsiloxane, polyethylene, polyacrylonitrile, cellulosic materials, polycarbonates and polyvinyl pyridinium.

In an exemplary embodiment, the substrate is permeable and it consists of a material, that is permeable to liquids, vapors and/or gases. The liquids and gases can be pure compounds (e.g., chloroform, carbon monoxide) or they can be compounds which are dispersed in other molecules (e.g., toxins or explosives in air, solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In those embodiments wherein the permeability of the substrate is not a concern and a layer of a metal film is used, the film can be as thick as is necessary for a particular application. Exemplary films are of a thickness of from about 0.01 nanometer to about 1 micrometer. In a further exemplary embodiment, the film is of a thickness of from about 5 nanometers to about 100 nanometers. In yet another exemplary embodiment, the film is of a thickness of from about 10 nanometers to about 50 nanometers.

Substrate Surfaces

In various embodiments, the structure of the surface of the substrate has an effect on the anchoring of the detection layer which is associated with the surface of the substrate. The surface can be engineered by the use of mechanical and/or chemical techniques. The surface of each of the above enumerated substrates can be substantially smooth. Alternatively, the surface can be roughened or patterned by rubbing, etching, grooving, stretching, oblique deposition or other similar techniques known to those of skill in the art. Of particular relevance is the texture of the surface which is in contact with the fiber bundles of the detection layer.

Thus, in one preferred embodiment, the substrate is glass or an organic polymer and the surface has been prepared by rubbing. Rubbing can be accomplished using virtually any material including tissues, paper, brushes, polishing paste, etc. In a preferred embodiment, the rubbing is accomplished by use of a diamond rubbing paste. In another preferred embodiment, the face of the substrate that contacts the mesogenic compounds is a metal layer that has been obliquely deposited by evaporation. In a further preferred embodiment, the metal layer is a gold layer.

The substrate can also be patterned using techniques such as photolithography (Kleinfield et al., *J. Neurosci.* 8:4098-120 (1998)), photoetching, chemical etching and microcontact printing (Kumar et al., *Langmuir* 10: 1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y; Whitesides, G., *J. Am. Chem. Soc.* 117:3274-75 (1995). Similarly, using photolithography, patterns with features as small as 1 µm have been produced. See, Hickman et al., *J. Vac. Sci. Technol.* 12:607-16 (1994). Patterns which are useful in the present invention include those which comprise features such as wells, enclosures, partitions, recesses, inlets, outlets, channels, troughs, diffraction gratings and the like.

In a presently preferred embodiment, the patterning is used to produce a substrate having a plurality of adjacent wells, wherein each of the wells is isolated from the other wells by a raised wall or partition and the wells do not fluidically communicate. Thus, an analyte, or other substance, placed in a particular well remains substantially confined to that well. In another preferred embodiment, the patterning allows the creation of channels through the device whereby an analyte can enter and/or exit the device.

The pattern can be printed directly onto the substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art. See, for example, Kleinfield et al., *J. Neurosci.* 8:4098-120 (1998). Following removal of the photoresist, a second organic layer, having a structure different from the first organic layer can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similarly, positively or negatively charged compounds can be confined to wells having walls made of compounds with charges similar to those of the confined compounds. Similar substrate configurations are accessible through microprinting a layer with the desired characteristics directly onto the substrate. See, Mrkish, M.; Whitesides, G. M., *Ann. Rev. Biophys. Biomol. Struct.* 25:55-78 (1996).

In an exemplary embodiment, the patterned substrate controls the alignment of the fiber bundles.

Microarrays

The invention also provides microarrays including immobilized fiber bundle detection layers. Moreover, the invention provides methods of interrogating these microarrays for detecting the presence of an analyte of interest.

In an exemplary embodiment, the first plurality of self-assembled fiber bundles are deposited on said substrate in a first matrix and in a second matrix. In various embodiments, the first plurality of self-assembled fiber bundles is deposited on the substrate in a first matrix and a second plurality of self-assembled swellable fiber bundles is deposited on the substrate in a second matrix. The molecules in the first matrix differ from those in the second matrix. The difference may be any difference that leads to a difference in a signal event between the first matrix and the second matrix. Exemplary differences include chemical structure differences, differences in fiber dimension (e.g., swelling), differences in degree of pulling (elongation) of the fibers, differences in the composition, pattern or structure of the substrate, and differences in a molecule expressed on or conjugated to the surface of the fiber. Other differences include, differences in spacing between a first fiber bundle and a second fiber bundle of the first matrix and the second matrix.

In an exemplary embodiment, the detection layer of the first matrix and that of the second matrix have detectable colorimetric differences upon binding the respective analyte of interest. Thus, for example, the color of the first matrix on binding an analyte of interest is different than the color of the second matrix upon binding an analyte of interest.

Microarrays of the invention are analogous, to nucleic acid microarrays consisting of a multitude of immobilized nucleic acids, which proved revolutionary tools for the generation of genomic information, see, Debouck et al., in supplement to *Nature Genetics*, 21:48-50 (1999).

In various embodiments, the detection layers of the present invention are utilized in a microarray format. Exemplary microarrays comprise n detection layers that comprise identical or different fibrous species. In an exemplary embodiment, n is a number from 2 to 100, more preferably, from 10 to 1,000, and more preferably from 100 to 10,000. In a still further preferred embodiment, the n detection layers are patterned on a substrate as n distinct locations in a manner that allows the identity of each of the n locations to be ascertained and, therefore, the identity of analytes of interest interacting with the layers to be determined.

In yet another exemplary embodiment, the invention also provides a method for preparing a microarray of n detectable layers. The method includes attaching fiber bundles of the detection layers to selected regions of a substrate. A variety of methods are currently available for making arrays of biological macromolecules, such as arrays of nucleic acid molecules.

An exemplary method for making ordered arrays of detection layers on a substrate is a "dot blot" approach. In this method, a vacuum manifold transfers a plurality, e.g., 96, aqueous samples of fibrous bundles from 3 millimeter diameter wells to a substrate. The detection layer is immobilized on the porous membrane any art-recognized method. A common variant of this procedure is a "slot-blot" method in which the wells have highly-elongated oval shapes.

Another technique employed for making ordered arrays of detection layers uses an array of pins dipped into the wells, e.g., the 96 wells of a microtiter plate, for transferring an array of fibrous bundles to a substrate, such as a porous membrane. One array includes pins that are designed to spot a membrane in a staggered fashion. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990).

Immobilization of Detectable Layer (e.g., Phage)

The devices of the invention can include a detection layer that is immobilized on a substrate. The fiber bundles of the detection layer can interact adventitiously through a non-specific interaction with the substrate surface or they can be anchored to the surface through a specific interaction. An exemplary immobilized detection layer is composed of fiber bundles of phage.

In an exemplary embodiment, a phage preparation is immobilized to a biosensor substrate. A phage preparation can be passively immobilized to a biosensor surface. The phage surface can be blocked and an antigen (e.g. small molecule, carbohydrate, polymer, peptide, soluble protein, antigen mimic of a cellular receptor, or mammalian cells) can be screened for binding to the immobilized phage. The binding of the antigen specifically to the phage is measured by the change in signal generated by such a binding event, typically via optical, electrical or visual means. Antigen binding to the phage can be ranked by concentration of the phage, off-rate of the antigen, and the ability of the phage to functionally bind an analyte of interest.

A phage preparation can be immobilized to a biosensor surface using specific antibody immobilization. An antibody to a phage coat protein is immobilized to the biosensor surface. The antibody can be passively immobilized to the biosensor surface or via a specific surface such as protein A or a protein A plus anti-Fc surface. The surface can be blocked by a blocker. The binding of the phage specifically to the surface is measured by the change in signal generated by such a binding event, typically via optical, electrical or visual means. The display on the phage (virus) can be a peptide, small protein, and/or an antibody fragment or non-existent. The binding of the cognate ligand is then sequentially measured by the change in signal generated by such a binding event, typically via optical, electrical or visual means. The ligand can be, e.g., a small molecule, carbohydrate, polymer, peptide, soluble protein, antigen mimic of a cellular receptor or a protein on the surface of cells. The protein expressed on the surface of the cell can be, e.g., a membrane-associated protein, a single or multi-transmembrane protein, or a protein channel.

A phage preparation can be immobilized to a biosensor surface by an antigen bound to the biosensor surface. An antigen (such as a small molecule, carbohydrate, polymer, peptide, soluble protein, or antigen mimic of a cellular receptor) is immobilized on the biosensor surface in a passive or specific surface such as an antibody that does not interfere with the desired binding epitope being screened. The antigen surface can be blocked. The binding of the phage preparation specifically to the antigen is measured by the change in signal generated by such a binding event, typically via optical, electrical or visual means. The display on the phage can be, e.g., a peptide, small protein, and/or an antibody fragment. Phage binding to the antigen can be ranked by concentration of the antigen, and the off-rate of the phage.

Molecules can be immobilized onto a biosensor so that they will not be washed away by rinsing procedures, and so that binding to molecules in a test sample is unimpeded by the biosensor surface. Several different types of surface chemistry strategies have been implemented for covalent attachment of molecules to, for example, glass for use in various types of microarrays and biosensors. These same methods can be readily adapted to a biosensor of the invention.

One or more types of molecules can be attached to a biosensor surface by physical adsorption (i.e., without the use of chemical linkers) or by chemical binding (i.e., with the use of chemical linkers). Chemical binding can generate stronger attachment of molecules on a biosensor surface and provide defined orientation and conformation of the surface-bound molecules.

Other types of chemical binding include, for example, amine activation, aldehyde activation, and nickel activation. These surfaces can be used to attach several different types of chemical linkers to a biosensor surface. While an amine surface can be used to attach several types of linker molecules, an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal Chem.* 68, 490, (1996)).

Immobilization of specific binding substances to plastic, epoxy, or high refractive index material can be performed essentially as described for immobilization to glass. However, an acid wash step can be eliminated where such a treatment would damage the material to which the specific binding substances are immobilized.

In some embodiments, the present invention provides sensors and/or kits for explosives detection. In some embodiments, the sensors and/or kits include the explosives detecting substrate described herein. A "sensor" refers to any device or article capable of detecting an explosive material.

In some embodiments, the kits include a sensor device of the invention. In some embodiments, the kit further includes a UV light (e.g. a handheld UV light) and/or instructions for detecting an explosive material. In other embodiments, the kits include a handheld device, e.g., a cellular device, loaded with a software application that enables the device to read the colorimetric signals from the sensor and process the information contained in those signals into a display useful to the end user. As will be apparent to those of skill in the art, essentially any device capable of detecting an optically detectable change is of use in the present invention. Such devices include, but are not limited to spectrometers, photometers, photodiodes, and CCD devices.

The sensor may further comprise other common features of explosives detectors, for example, an emission detector positioned to detect color change (or lack thereof); an inlet for intake of a sample (e.g. vapor sample, solution sample); and/or a sample cell constructed and arranged to receive the sample. In some embodiments, the sensor includes a complementary analytical device (e.g., a device which performs colorimetric detection, absorption spectroscopy, mass spectroscopy, Raman, and/or other appropriate analytical technique). Such analytical devices, when utilized with the explosives detection substrate of the present teachings, can increase the sensitivity of a sensor. In some embodiments, the sensor includes a hand held device that detects color changes. The use of a such a device in conjunction with the explosives detection substrate of the present teachings may increase the sensitivity of a sensor by allowing the detection of very small changes is color or color intensity (e.g., changes that may not be noticeable upon direct visual inspection). The use of such a device in conjunction with the explosives detection substrate of the present teachings may also decrease the time required to detect the presence of an explosive material. For example, it may take a few minutes to visually inspect a substrate for a change in color or color intensity, whereas the use of a sensor (e.g., with a device detecting color change or intensity change) may only require a few seconds. In some embodiments, the sensor includes an absorption spectrometer.

In one embodiment, the sensor also includes an article to provide enhanced rigidity, sensitivity, selectivity, stability, or a combination of any number of these features, to the explosives detection substrate in the sensor. The article can be positioned adjacent the substrate and can be selected from beads, nanoparticles, polymer fibers, waveguides and a film. In one embodiment, a sensor can be provided comprising an explosives detection substrate positioned adjacent to a waveguide. Light emitted by the explosives detection substrate in one area can be captured by internal reflection in the substrate and then reabsorbed and re-emitted in a different region of the sensor. This process can occur many times before reaching a detector, resulting in a sensor with enhanced sensitivity. Sequential emission and reabsorption cycles increase the probability that an excitation will be quenched or trapped by an analyte.

In some embodiments, the kit and/or sensor is a robot or a remote controlled device. For example, in some embodiments, the explosives detection substrate, or optionally the electrospinning system can be incorporated into a remote controlled vehicle, such as an unmanned vehicle or aircraft. Placing the explosives detection device into a non-human system can result in fast screening of test environments in large scale with little or no danger to humans.

Systems

According to another aspect, the article further comprises a transmitter in communication with the target sensor, and the method comprises the step of transmitting a signal in response to detection of the target in the sample. According to an exemplary embodiment, the system comprises a plurality of different types of detection layers, where, for example, each different type of detection layer generates a unique notification signal.

In some embodiments of the present invention, there is provided a monitoring apparatus configured to be worn by a person includes a physiological sensor that is oriented in a direction towards the person and an environmental sensor that is oriented in a direction away from the person. A buffer material is optionally positioned between the physiological sensor and environmental sensors and is configured to selectively reflect and/or absorb energy emanating from the environment and/or the person.

In some embodiments of the present invention, a sensor is combined with a cellular communication device to form a monitoring apparatus. The monitoring apparatus may include a receiver that is configured to receive audio and/or video information from a sensor of the invention, and a communication module that is configured to store and/or process and/or play audio and/or video information received from the sensor. In some embodiments, the communication module may be configured to alert (e.g., via audible and/or visible and/or physical alerts) a person wearing the apparatus when a sensor detects certain environmental information from the vicinity of the person. In some embodiments, the communication module is configured to audibly present environmental information to the person wearing the apparatus. In some embodiments, the communication module may be configured to store content generated by the sensor.

In some embodiments of the present invention, a monitoring apparatus may include a transmitter that is configured to transmit signals produced by environmental sensors associated therewith to a cellular communication device, forming a monitoring system. The monitoring system may be configured to receive feedback regarding monitored health and environmental parameters (e.g., levels of an analyte of interest, humidity, temperature, etc.). As such, personal health and environmental feedback can be an active component of a system of environmental monitoring.

In an exemplary embodiment, the system transmits a signal regarding the environment of the sensor to a social media application (e.g., Twitter, Facebook).

In an exemplary embodiment, sensors of the invention are incorporated into clothing, e.g., the clothing of military personnel or first responders as part of a sensor system.

In an exemplary embodiment, the cellular communication device in operative linkage with the sensor of the invention analyzes the color and/or color intensity displayed by the sensor. FIGS. 27A-29B.

These are only a few examples of the utility of fibers made from engineered viruses, and other applications are readily apparent to one of skill in the art.

Software

In an exemplary embodiment, the invention provides a software program or application of use in processing data from a sensor of the invention. In various embodiments, the software application controls the acquisition of the data from the sensor. In an exemplary embodiment, the software application compiles data from the sensor, processes this data into a visual or audible format and displays or transmits the processed data to a device comprising a user interface capable of displaying (or announcing) the results derived from processing the data.

Thus, in an exemplary embodiment, the application collects data from the sensor, processes the data in a manner selected by the user and displays the processed data on an appropriate user interface. In an exemplary embodiment, the display is a visual or numeric display directly translating the colorimetric data displayed by the sensor. In various embodiments, the display is a binary display showing a difference in two states, e.g., SAFE CONDITION and UNSAFE CONDITION. The display of the process data can be an audible or legible display, a vibration, or other modes of providing warning or transmitting information about ambient environmental conditions.

In an exemplary software application, a workflow is: App starts 2. The user selects between input mode S1~S5, D1~D5 (S/DX denotes single/double sample mode, and the number X denotes the number of regions). At this stage, the regions on the image from which the RGB data will be calculated are defined. 3. The user takes the image of one (the sample) or two samples (the reference and the sample), according to which mode (S/D) the user selected. All the functions of the basic imaging software like light on/off are available. 4. The user expands or contracts and drags the image taken at so that the image fills the guiding window and the regions to be analyzed are aligned. 5. For each row (reference, sample) and for each region (X), the app calculates the mean value of the RGB values (and their standard deviation) if single mode, and the mean values of the difference of RGB between reference and sample if using double mode. 6. The report displays for each region the mean value of the RGB if single mode, and the mean values of the difference of RGB between reference and sample if double mode in table and bar graphs. 7. Saves the screenshot of the reporting image. 8. App ends.

Other workflows of use with sensors and systems of the invention will be apparent to those of skill in the art.

Methods

In an exemplary embodiment, the invention provides a method for detecting a first analyte of interest using a device of the invention. The method comprises contacting a device or system of the invention with a first analyte, wherein the contacting causes at least a fraction of the fiber bundles to undergo a change from the first conformation to the second conformation upon interaction with the first analyte of interest. The conformation change induces a colorimetric change in the detection layer, e.g., a color change. The colorimetric change is detected, e.g., the color change is detected.

In an exemplary embodiment, the first analyte of interest binds with the recognition moiety for said first analyte of interest. An exemplary recognition moiety is conjugated to or expressed on the surface of the fiber bundle.

In some embodiments, the present invention provides methods for detecting an explosive material. Such methods may generally include contacting the explosives detecting substrate described herein with an explosive material for at least about 1 second; measuring a color change in a device of the invention; and comparing the amount and nature of color change with a suitable control. An explosive material can be detected where the color change of the explosives detecting device of the invention is greater than a color change of the suitable control.

According to one embodiment, the invention provides a method of using a system of the invention for detecting a chemical, biological, radiological, or explosive target in a sample using an article of clothing worn by a user, the article comprising a target sensor, wherein the target sensor comprises a plurality of fiber bundles capable of binding to the analyte of interest and responding colorimetrically thereto, the method comprising the steps of: (i) contacting the article with a sample containing or thought to contain an analyte of interest, wherein the detection layer responds colorimetrically in response to binding of the target to the plurality of fiber bundles to produce a colorimetric notification signal; (ii) detecting the colorimetric notification signal, wherein the signal indicates the presence of the analyte of interest in the sample; and (iii) transmitting the signal to a cellular communication device in operative contact with the sensor.

In various embodiments, the colorimetric change on binding the analyte of interest is detected by a detector. The detection may be by any of visual observation, optical detection, microscopy, a spectroscopic technique, an electronic technique or a combination thereof. Visual observation detects a change in a member selected from reflectance, transmission, absorbance, dispersion, diffraction, polarization and combinations thereof, of light impinging on the device. The microscopic methods are selected from light microscopy, polarized light microscopy, atomic force microscopy, scanning tunneling microscopy and a combination thereof. Spectroscopic methods are selected from infrared spectroscopy, Raman spectroscopy, x-ray spectroscopy, visible light spectroscopy, ultraviolet spectroscopy and a combination thereof. Electronic techniques are selected from surface plasmon resonance, ellipsometry, impedometric methods and combinations thereof.

Characterizing Samples and Association Values

The present invention encompasses the recognition that association signatures characteristic of particular analytes of interest are useful in a variety of contexts, for example to identify, characterize, detect, and/or isolate analytes of interest.

The present invention provides systems for determining association signatures characteristic of a given test sample using a device or system of the invention.

The present invention relates to any of the methods described herein comprising a step of determining an association value associated with the presence, absence or quantity of an analyte of interest. The present invention relates to a relationship that analytes of interest can be identified, detected and/or quantified by signals that are proportional to affinity between one or more disclosed components on a disclosed solid support and its binding partner or analyte of interest. In some embodiments, an association signature includes binding information sufficient to compare a particular quantity of interest with a reference sample and/or to identify, characterize, and/or distinguish a particular test sample with respect to other reference that do not comprise an analyte of interest.

In some embodiments, an association signature comprises information respecting absence, presence and/or level of binding interactions with one or more analyte of interest.

In some embodiments, an association signature distinguishes a sample from comparable samples of other origin. For example, in some embodiments, an association signature distinguishes a test sample from a comparable sample taken from a similar geographically placed water resource. In some embodiments, an association signature distinguishes a test sample from comparable sample taken from a similar geographically placed food source. In some embodiments, an association signature distinguishes a test sample from comparable reference sample that differs with respect to extent, degree, or type of exposure to one or more analyte of interest (including explosives, drugs, toxins, contaminants, etc).

In some embodiments, detection or determination of an association signature reveals information about identity, extent, and or nature of one or more components contained within a test sample, and/or of one or more factors present on (e.g., expressed or captured on) in a test sample or on a surface. To give but one example, existence and/or level of particular binding interactions in an association signature of a sample can reveal identity, extent, and or nature of a sample or surface component such as, for example, an explosive binding a recognition moiety specific to the explosive. Presence of the explosive, or other contaminant, can indicate a hazardous condition or place that should be avoided or cleaned prior to use, ingestion or exposure by a subject.

In some embodiments, association signatures are determined by contacting a sample with an array or system disclosed herein; quantifying one or more association values; and compiling the one or more association values to create one or more association signatures. In some embodiments, the step of quantifying one or more association values comprises detecting a quantitative signal or signals relative to the sample binding to one or a plurality of association probes, normalizing the quantitative signals as compared to a control sample, and applying an algorithm or interpretation function disclosed herein to the quantitative signal or signals such that the output of the algorithm or interpretation function disclosed herein comprises one or a plurality of association values. In some embodiments, the step of applying the algorithm or interpretation function disclosed herein is performed by a non-transitory computer program product. In some embodiments, one or more steps of the methods disclosed herein are performed by a non-transitory computer implemented method.

Association values can be determined using a system of the invention.

Once the one or plurality of association values are calculated using the algorithm or interpretation function, one can create or determine an association signature for the sample which, in some embodiments, is a quantitative binding profile of sample relative to the one or plurality of explosives or analogs thereof to which sample has been contacted. A user of the array or system disclosed herein can subsequently compare the association signature sample to one or a plurality of association signatures of control samples. In some embodiments, the association signatures of the one or plurality of control samples is predetermined and/or catalogued so that the user of the array or system disclosed herein can compare the signatures of the sample to the predetermined and/or catalogued control signature to identify the level of molecule or contaminant (e.g., explosive) on a surface, in a fluid (e.g., water, or bodily fluid), or air sample. In some embodiments, the association signatures of the one or plurality of controls is predetermined and/or catalogued so that the user of the array or system disclosed herein can compare the signatures of the test sample to the predetermined and/or catalogued control association signature to qualitatively assess the test sample as having physical characteristics more or less similar to the control association signature. In some embodiments, the user of the array or system disclosed herein and generate a profile related to similarities or dissimilarities as between the test sample association signature and the control association signature. In some embodiments, the control association signature is association signature that quantitatively describes a set of association values from a panel of explosives.

The invention having been described, the following examples are offered to illustrate the subject invention by way of illustration, not by way of limitation.

EXAMPLES

Example 1

Biomimetic Virus-Based Colorimetric Sensors

We constructed a bioinspired, colorimetric sensing material composed of filamentous bacterial viruses (M13 phage) as depicted in FIG. 1. Tunable phage-based structures fabricated using a self-templating assembly process are composed of quasi-ordered phage bundle nanostructures and exhibit viewing-angle independent colors[25]. These films mimic the structure of turkey skins (*M. gallopavo*, Pitman Farms, Sanger, Calif.), which are structurally colored blue due to coherent scattering of light from collagen bundle-based nanostructures (FIG. 1, panels A-C)[11]. Arrays of differently colored phage matrices, termed Phage litmus (FIG. 1, panel D), rapidly swell or shrink upon exposure to external chemicals, resulting in color changes similar to those seen on turkeys when they get flustered (FIG. 1, panel A). The chemicals are identifiable through color pattern analyses in a quantitative manner. To enhance selectivity, a trinitrotoluene (TNT)-binding motif identified by phage display is incorporated onto the phage coats. The TNT-binding phage litmus detects TNT down to 300 ppb with the aid of a common handheld device (iPhone) and can distinguish between similar nitroaromatic molecules (i.e. TNT, dinitrotoluene (DNT), and mononitrotoluene (MNT)). The facile synthesis, ease of use, portability, and successful introduction of tunable receptors suggest that Phage litmus colorimetric sensors can be useful for the detection of a wide variety of harmful toxicants and pathogens to protect human health and national security.

Results

Generation of Multi-Color Phage Litmus.

Figure 2A:
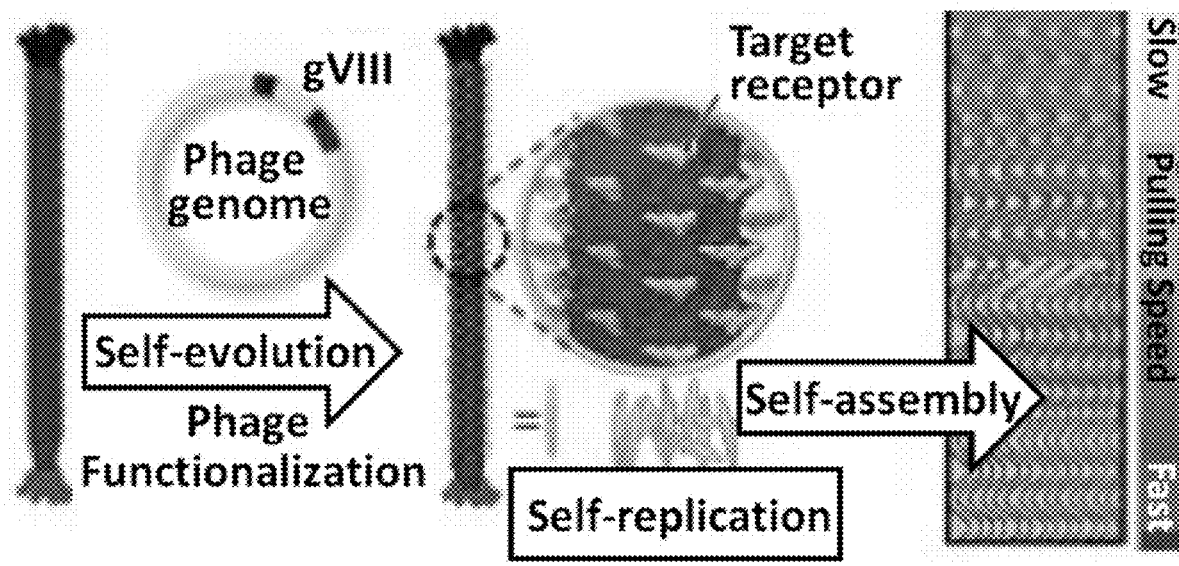
FIGS. 2A-2C show multi-color generation and structural modulation of the Phage litmus.
Figure 2B:
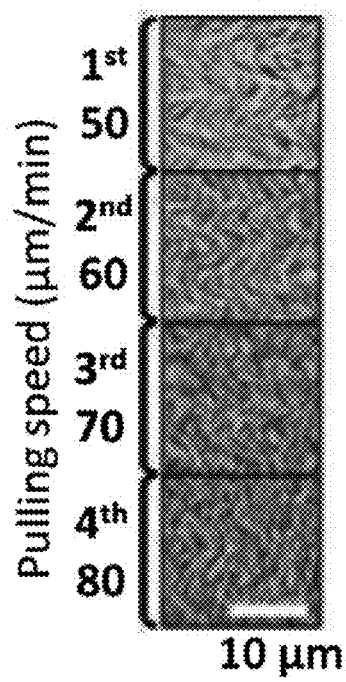

We developed tunable, multi-colored, thin film matrices composed of biomimetic fiber bundle nanostructures using M13 phage (FIG. 2A). M13 phage is a bacterial virus composed of single stranded DNA encapsulated by 2700 copies of the major coat protein (pVIII). Phages generate identical copies of themselves through infection of bacterial host cells. Because of its well-defined, monodisperse shape and its ability to display functional peptides, M13 phage has been utilized to fabricate various functional nanomaterials for semiconductor[26-28], energy[29-31], and bioengineering applications[32]. Recently, inspired by self-templated materials assembly processes in nature, we developed a process to fabricate an array of hierarchical phage-based structures through controlled extraction of a solid substrate from a solution of phage (FIG. 2B)[25]. By controlling the phage deposition process, we could easily fabricate distinct and tunable structurally-colored nanostructures, in which colors do not appear to be strongly angle dependent. (FIG. 2B, FIG. 2C, FIG. 5, FIGS. 6A-6C). Unlike typical synthetic photonic crystals which often rely on crystalline arrays or multi-layer thin films[33,34], the colored regions of our self-templated materials were found to be composed of quasi-ordered fiber bundles that are remarkably similar to the collagen fiber bundles found in structurally colored avian and mammalian skins[10,11]. Atomic force microscopy (AFM) and fast Fourier transform (FFT) analyses showed that the observed colors are attributable to coherent scattering from the fiber bundle structures (FIG. 2B, FIGS. 7A & 7B, and FIGS. 8A-8C). In quasi-ordered structures such as ours, the observed colors are determined by the average inter-particle distance. A similar mechanism for angle-independent structural color generation has been observed in animals and insects due to the presence of quasi-ordered dermal protein arrays[7,13,35].

Phage Litmus Based Humidity Sensor.

Figure 2C:
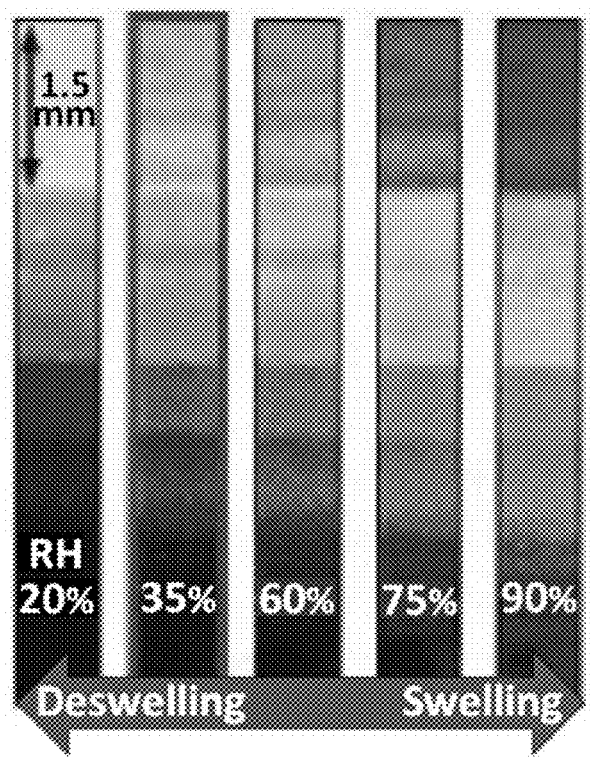
Figure 2D:
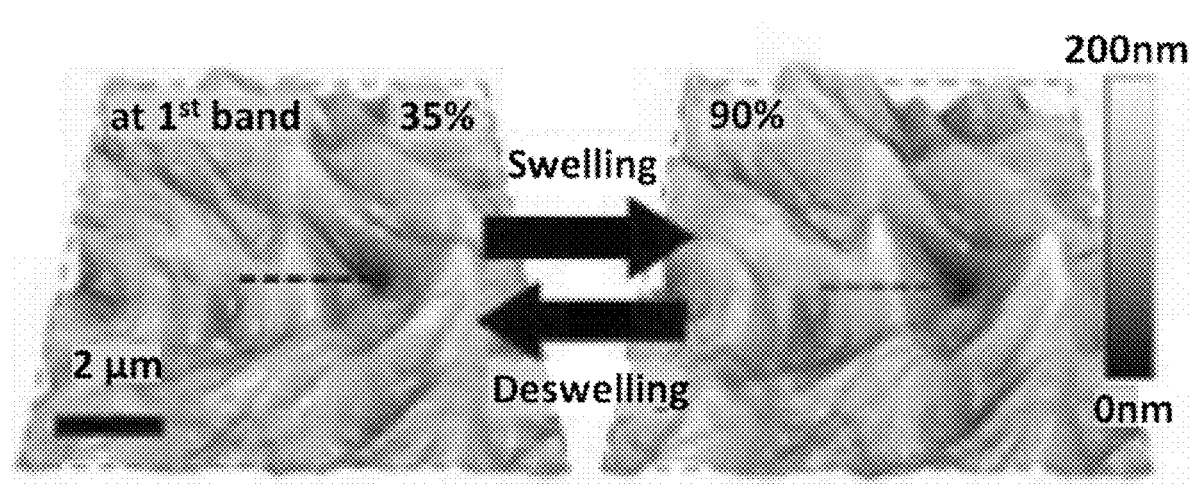
FIG. 2D) AFM images of the $1^{st}$ phage matrix band at 35% and 90% RH, respectively. Changes in color are due to modulation of the phage bundles' structures. Height profiles of the cross section (dotted lines) showed that bundle diameter increase 104 nm after swelling (FIG. 10F).
Figure 2E:
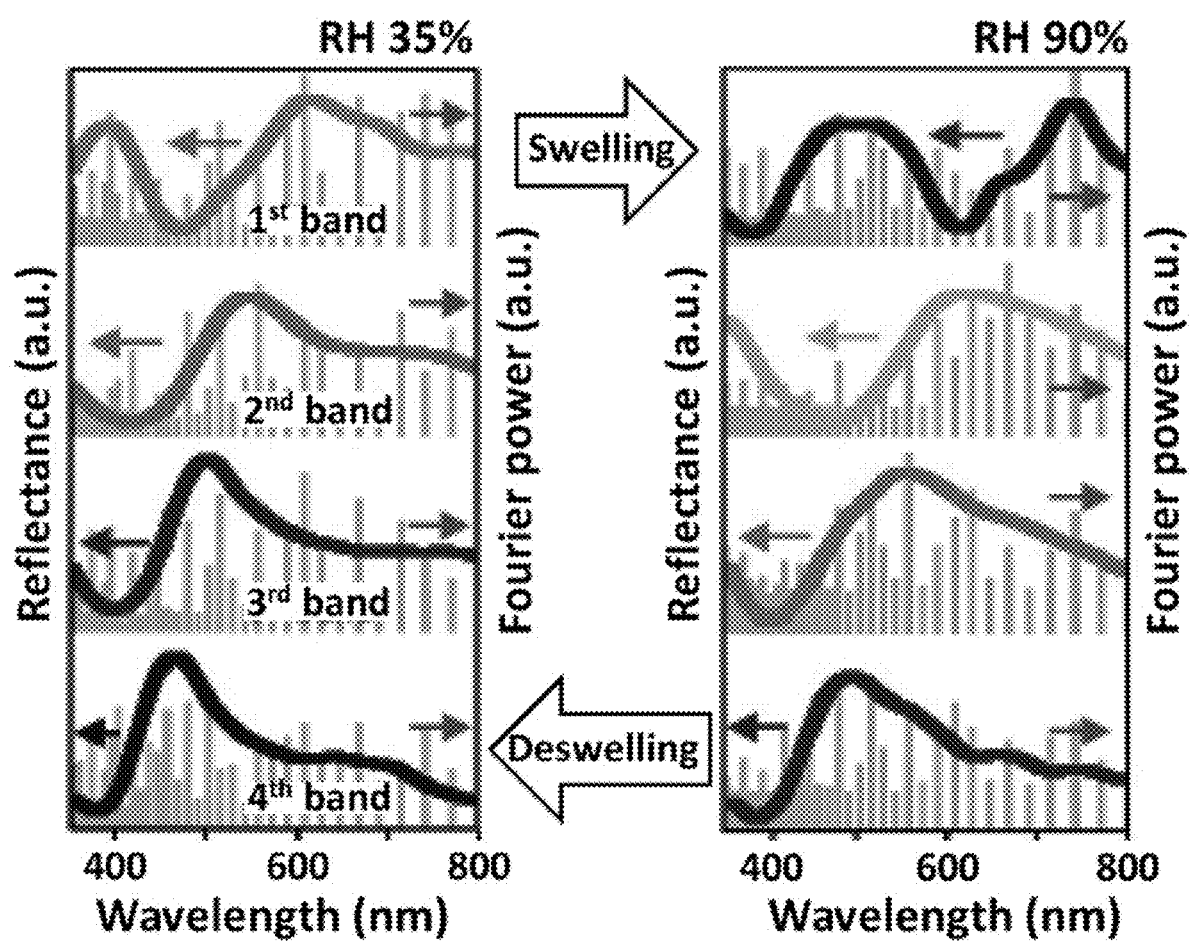
FIG. 2E) Reflectance spectra (colored lines) at normal angle and Fourier power spectra (gray bars) of each phage matrix in 35% and 90% RH generally correspond to each other in hue (position of peak) and chroma (shape of peak) (a.u.: arbitrary units).
Figure 9:
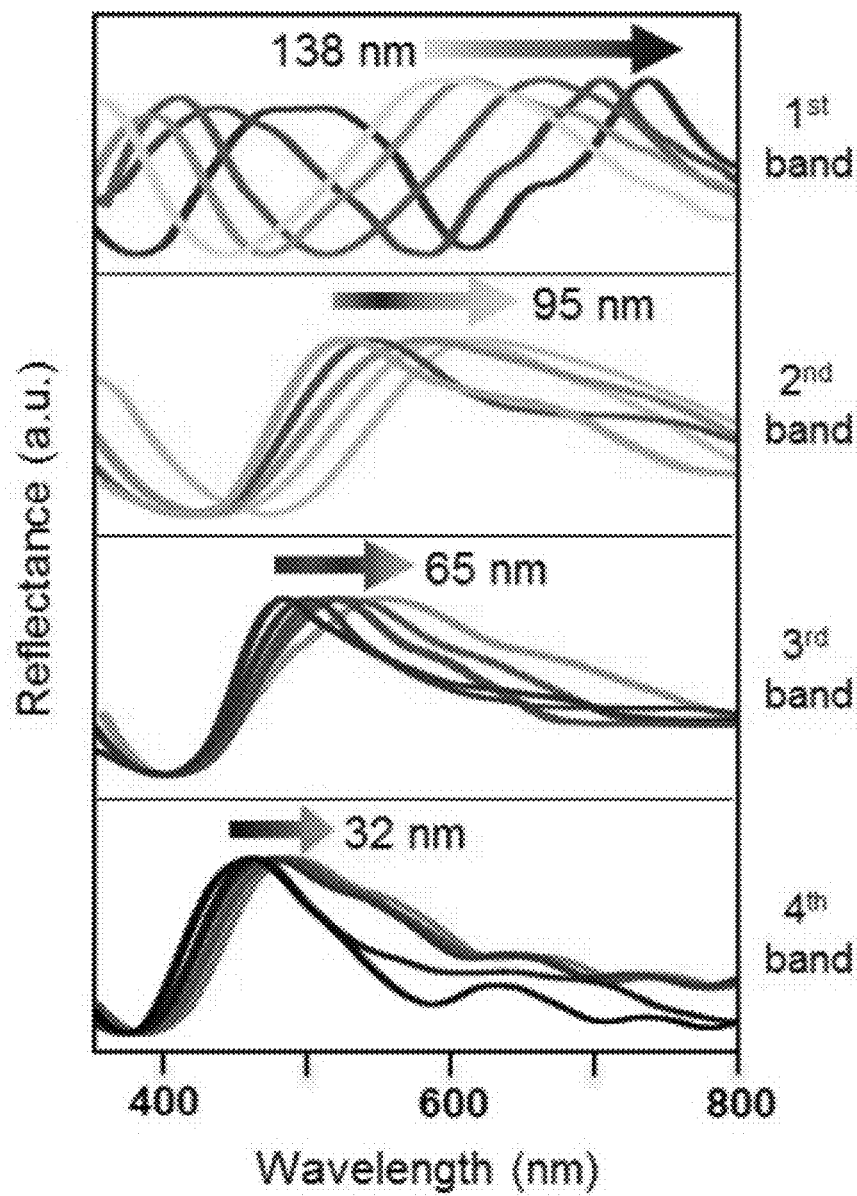
FIG. 9. Reflectance spectra of each color band on Phage litmus matrices upon exposure to RH of 20% to 90%. Reflectance spectra of the Phage litmus at normal angle for the matrices shown in FIG. 2B. As RH increased the color of each band red-shifted to a different extent depending on its initial bundle structure.
Figure 10A:
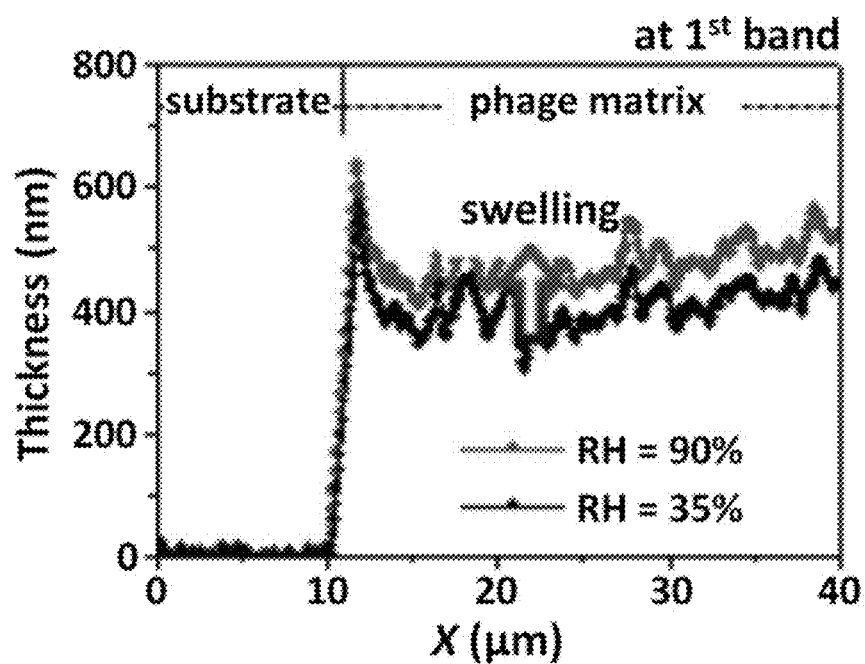
FIGS. 10A-10F shows AFM analysis of the swelling effect of Phage litmus matrices at different humidity levels. The diameter of initial phage bundle structure increased as the RH increased from 35 to 90%: on (FIG. 10A) $1^{st}$ band 412 nm to 494 nm.
Figure 10B:
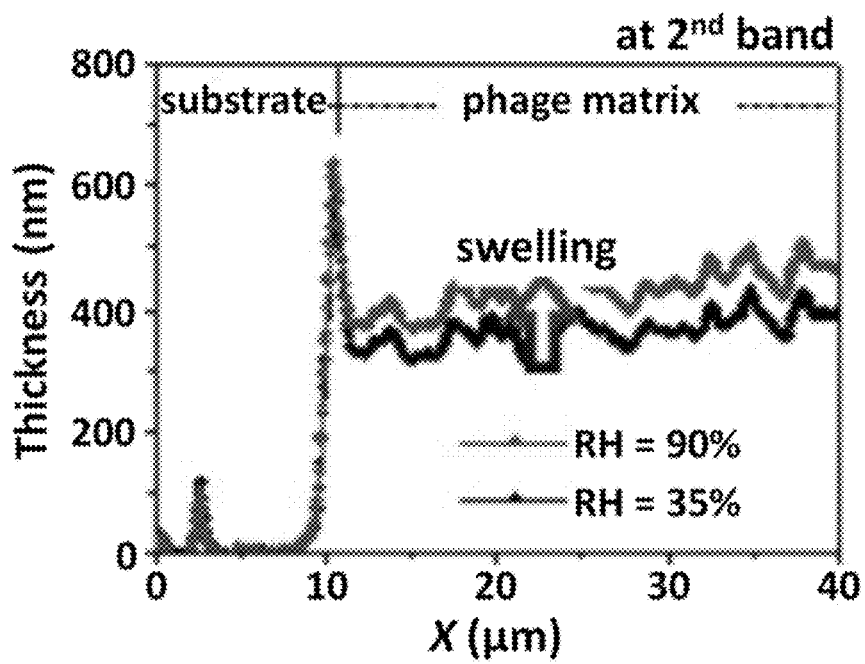
Figure 10C:
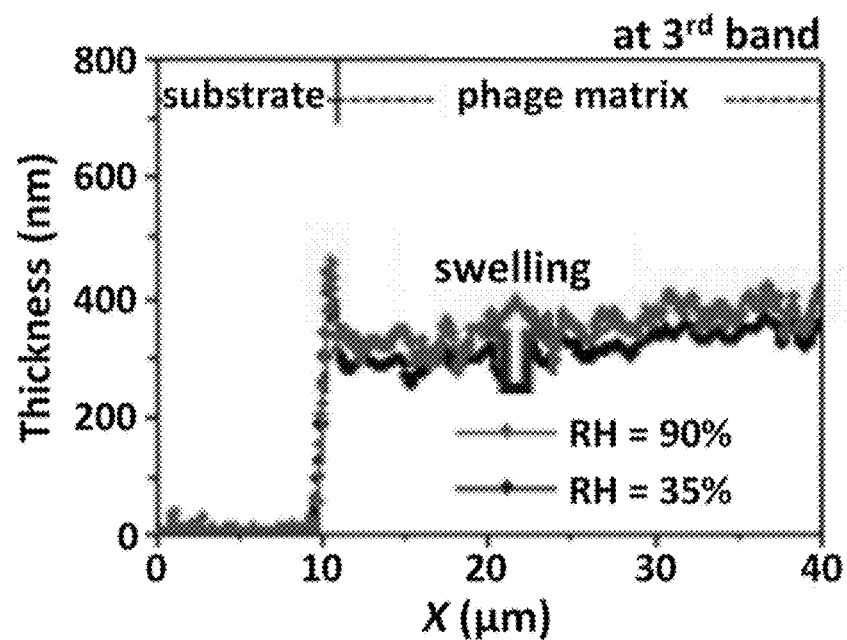
Figure 10D:
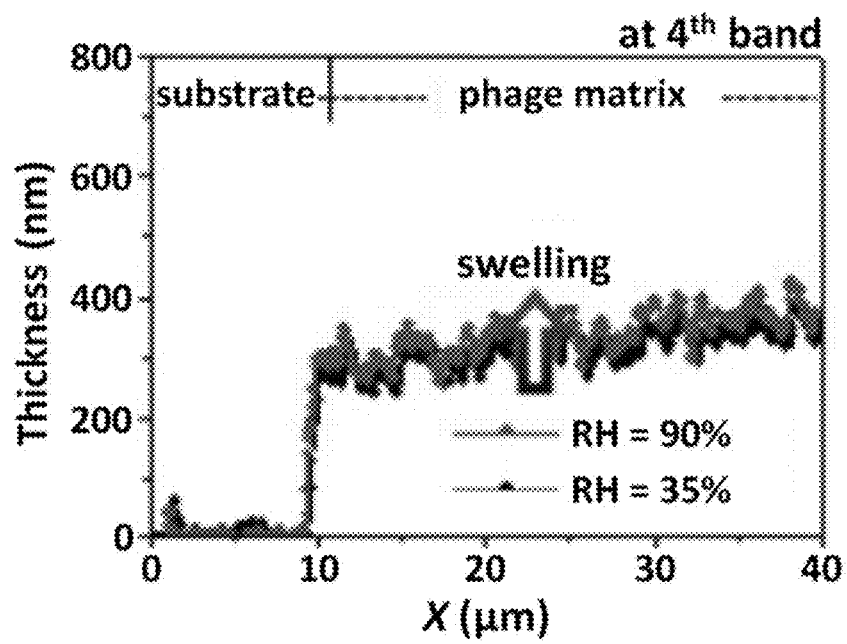
Figure 10E:
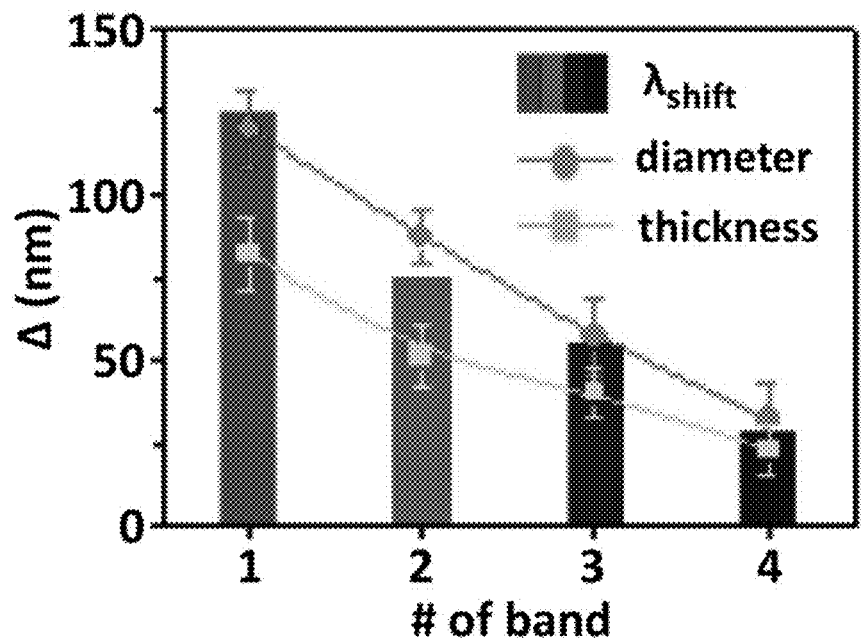
Figure 10F:
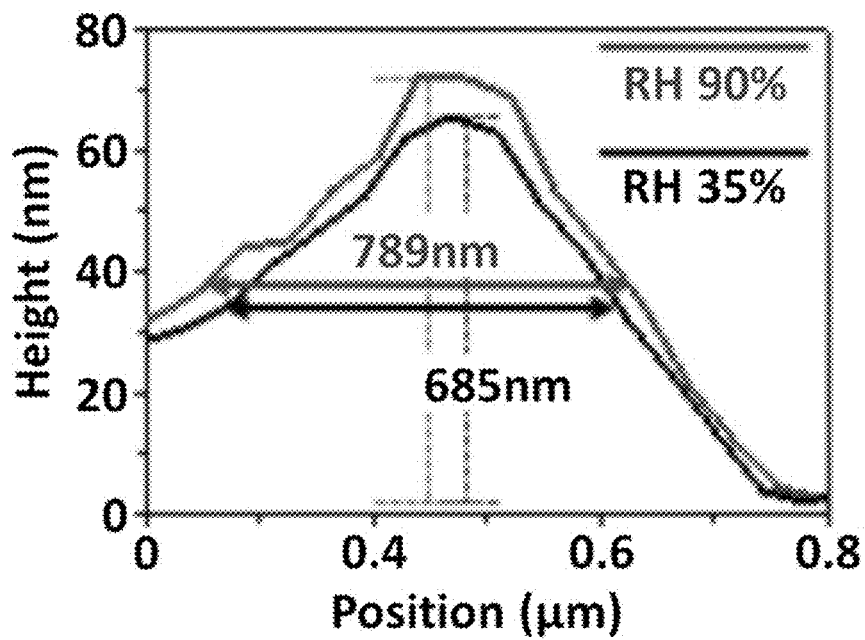

The multi-colored Phage litmus exhibits structural responses upon exposure to chemicals. The color of each band of a Phage litmus red-shifted with increasing humidity, and blue-shifted with decreasing humidity (FIG. 2C). Optical characterization showed that the reflectance spectra correlated to each visible color (FIG. 9). When we increased the relative humidity from 35% to 90%, the observed wavelength of the reflectance spectrum increased (Δ=124, 75, 55, and 28 nm for the $1^{st}$, $2^{nd}$, $3^{rd}$, and $4^{th}$ band, respectively). AFM imaging analysis revealed that the changes in color were due to modulation of the phage bundle structures and subsequent thickness changes (FIG. 2D), with each band swelling to a different extent. When the relative humidity increased from 35% to 90%, the bundle diameter changed by 120, 87, 55, and 32 nm and the band film thickness changed by 82, 51, 40, and 23 nm for the $1^{st}$, $2^{nd}$, $3^{rd}$, and $4^{th}$ matrices, respectively (FIGS. 10A-10F). The most pronounced color change was observed in the bands with the largest bundle diameters. FFT analyses of the AFM images also supported that the color change was due to swelling and increased interspacing between fiber bundles (FIG. 2E and FIGS. 8A-8C). During in situ grazing incidence small angle X-ray scattering (GISAXS) experiments, the (100) and (110) peaks arising from the pseudo-hexagonally packed matrix structure gradually disappeared due to structural changes caused by the exposure to humidity. (FIGS. 11A & 11B). Meanwhile, dynamic height measurements using AFM in a closed cell showed a structure change upon exposure to water vapor within 20 seconds (FIG. 12). Upon removal of stimuli, the Phage litmus recovered its original colors within a few seconds (FIG. 13). The color changes were observed repeatedly and reproducibly through more than a dozen cycles with little color hysteresis.

VOC Detection Using Phage Litmus.

Figure 3A:
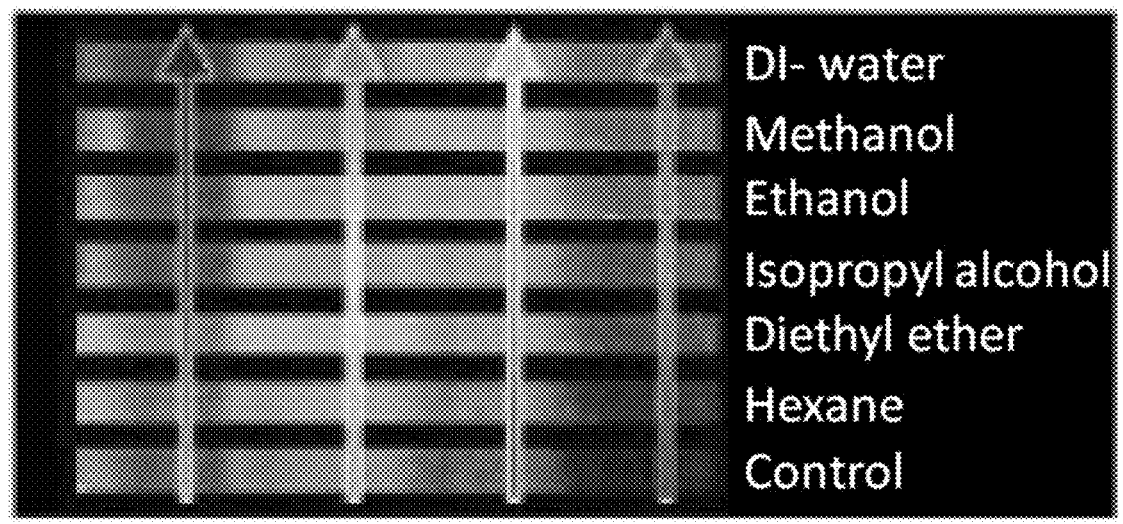
FIGS. 3A-3D illustrate phage litmus sensing of gas phase volatile organic compounds (VOCs).
Figure 3B:
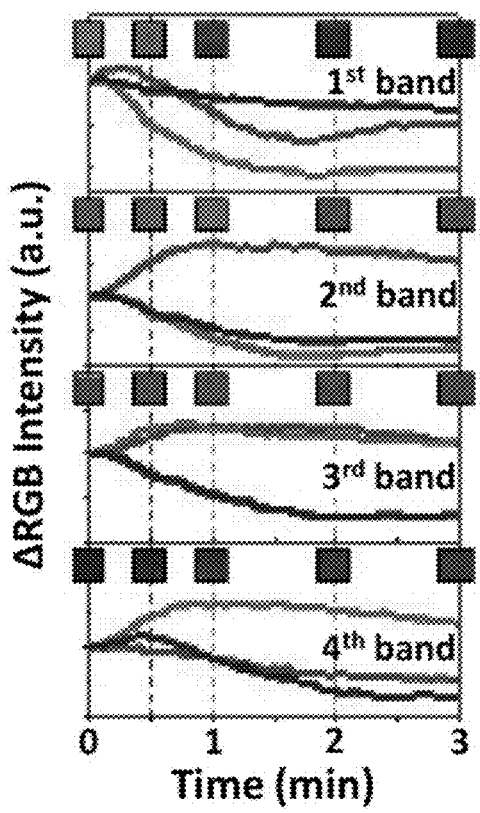
Figure 3C:
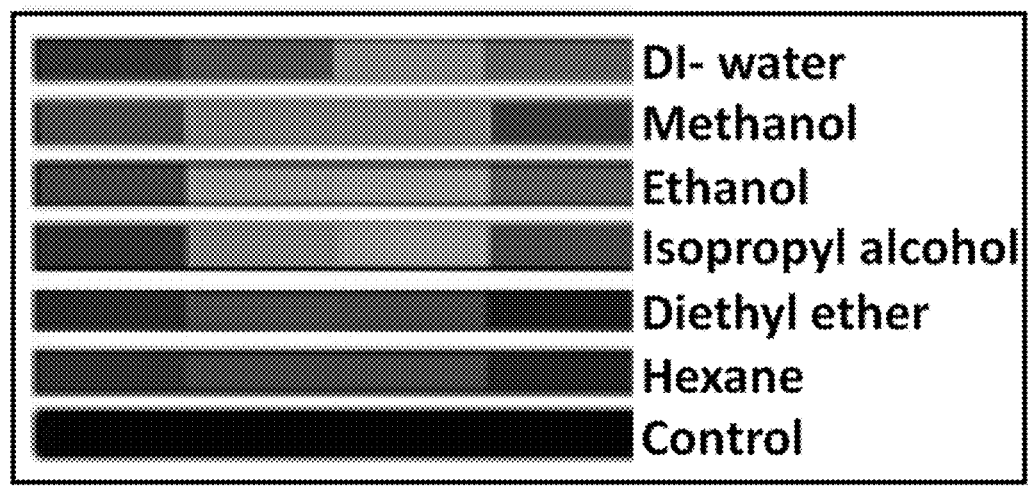
Figure 3D:
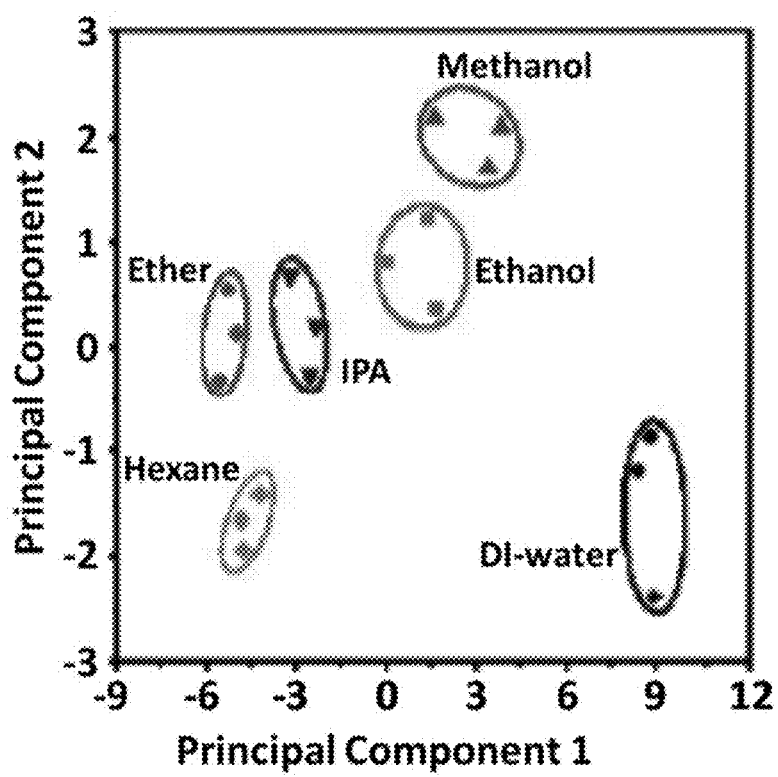

The Phage litmus exhibited characteristic color changes when exposed to volatile organic compounds (VOCs). Upon exposure to hexane, diethyl ether, isopropyl alcohol, ethanol, and methanol, the bands of the Phage litmus immediately changed color. These changes were distinguishable to the naked eye at 300 ppm of VOC (FIG. 3A). Quantitative real time response to the organic solvents was recorded using a charge coupled device (CCD) video camera controlled by a MATLAB program for RGB (red, green, and blue) color component analysis (FIG. 3B and FIG. 14). Using this system, we found that the sensors exhibited distinct color changes in response to the polarity index of the applied VOC (FIG. 15 and FIG. 16). We then created a reference "fingerprint" for each VOC by processing the amount the colors changed and generating synthetic color patterns (FIG. 3C and Table 1). These references could be compared to the pattern generated by exposure to an unknown VOC in order to identify the sample's identity. FIG. 3D shows a two-dimensional principal component analysis (PCA) plot containing points for each of the solvents from three measurements. The first two principal components account for 95% of the variance in the measurements. Clustering of data using PCA allows for assessment of the discrimination capabilities of the system and also demonstrates high reproducibility, as verified by the clustering of the data obtained for each solvent; DI-water (p1), methanol (p2), ethanol (p3), isopropyl alcohol (p4), diethyl ether (p5), and hexane (p6). Based on four different colorimetric matrices, we could clearly discriminate between the VOCs by polarity index; low polarity VOCs tended to group together in the negative range of the plot, well separated from the high polarity VOCs.

TABLE 1

Red-green-blue (RGB) color differences for DI-water, methanol (MeOH), ethanol (EtOH), isopropyl alcohol (IPA), diethyl ether (Ether), and n-hexane (Hexane).

| | R1 | G1 | B1 | R2 | G2 | B2 | R3 | G3 | B3 | R4 | G4 | B4 |
|---|---|---|---|---|---|---|---|---|---|---|---|---|
| DI H$_2$O 1 | −1.08 | −6.84 | −2.07 | 8.45 | −3.41 | −2.50 | 4.45 | 4.85 | −3.46 | 1.42 | 4.68 | 1.01 |
| DI H$_2$O 1 | −0.86 | −7.88 | −1.72 | 8.35 | −4.30 | −3.82 | 3.20 | 4.45 | −3.45 | −0.19 | 3.52 | 0.92 |
| DI H$_2$O 3 | −1.61 | −6.24 | 1.17 | 8.25 | −3.54 | −2.84 | 4.97 | 4.62 | −3.54 | 1.30 | 4.92 | 0.30 |
| MeOH 1 | 1.88 | −4.61 | −0.83 | 5.37 | −1.17 | −2.16 | 3.27 | 4.18 | −1.12 | 1.73 | 3.00 | 0.50 |
| MeOH 2 | 1.58 | −4.04 | −0.04 | 4.82 | 0.05 | −1.17 | 2.90 | 3.55 | −0.16 | 1.42 | 2.49 | 1.47 |
| MeOH 3 | 2.13 | −4.92 | −0.75 | 5.44 | −1.14 | −1.36 | 3.74 | 4.45 | −1.74 | 1.65 | 3.38 | 0.73 |
| EtOH 1 | 1.22 | −4.08 | −0.66 | 3.76 | −0.38 | −0.98 | 2.54 | 3.32 | −1.21 | 1.23 | 2.79 | 1.60 |
| EtOH 2 | 1.81 | −3.71 | −0.27 | 3.95 | −0.03 | −0.88 | 1.97 | 2.87 | −0.71 | 0.17 | 1.22 | −0.06 |
| EtOH 3 | 1.06 | −4.30 | −1.08 | 3.87 | −0.83 | −1.29 | 2.26 | 2.98 | −1.89 | 1.02 | 2.53 | 1.38 |
| IPA 1 | 1.16 | −1.89 | −0.09 | 2.23 | −0.12 | −0.53 | 1.04 | 1.88 | −0.30 | 0.05 | 0.75 | 0.08 |
| IPA 2 | 1.23 | −0.62 | 0.33 | 2.63 | 0.59 | 0.11 | 2.11 | 1.56 | 0.25 | 0.42 | 1.03 | 0.30 |
| IPA 3 | 1.28 | −1.44 | −0.32 | 2.89 | −0.26 | −0.58 | 1.73 | 1.36 | 0.05 | 0.72 | 1.07 | 0.98 |
| Ether 1 | 1.31 | 0.38 | 0.09 | 1.25 | 0.18 | 0.09 | 1.15 | 0.52 | 0.20 | 1.30 | 0.87 | 0.84 |
| Ether 2 | 1.20 | 0.56 | 0.25 | 1.22 | 0.74 | 0.53 | 1.53 | 0.55 | 0.37 | 1.54 | 0.78 | 0.52 |
| Ether 3 | 1.24 | 0.39 | 0.81 | 1.02 | 0.17 | 0.38 | 0.91 | −0.06 | 0.12 | 1.12 | 0.42 | 0.30 |
| Hexane 1 | 0.43 | −0.85 | −0.53 | 1.19 | −0.15 | −0.06 | 0.69 | 0.52 | −0.24 | −0.44 | 0.60 | 0.53 |
| Hexane 2 | 0.47 | −0.53 | −0.34 | 0.52 | −0.50 | −0.17 | 0.99 | 0.06 | −0.30 | 0.41 | 0.09 | −0.09 |
| Hexane 3 | 0.22 | −0.84 | −0.52 | 0.43 | −0.63 | −0.12 | 0.53 | 0.35 | −0.18 | 0.23 | −0.06 | −0.23 |

TNT Detection Using TNT-Phage Litmus.

Figure 4A:
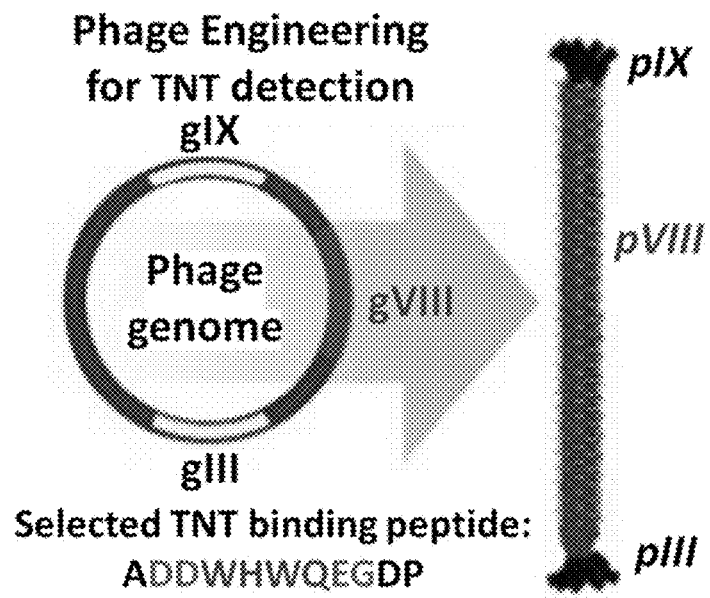
FIGS. 4A-4C illustrate gas phase TNT detection using TNT-Phage litmus.
Figure 4B:
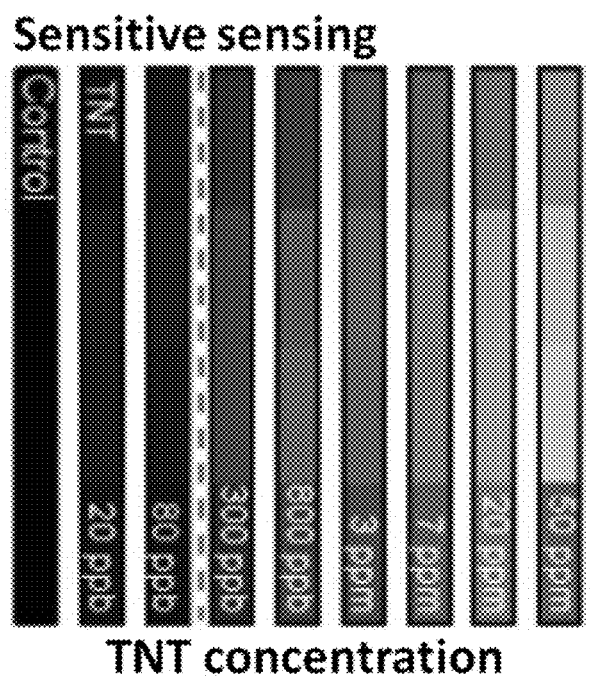
Figure 4C:
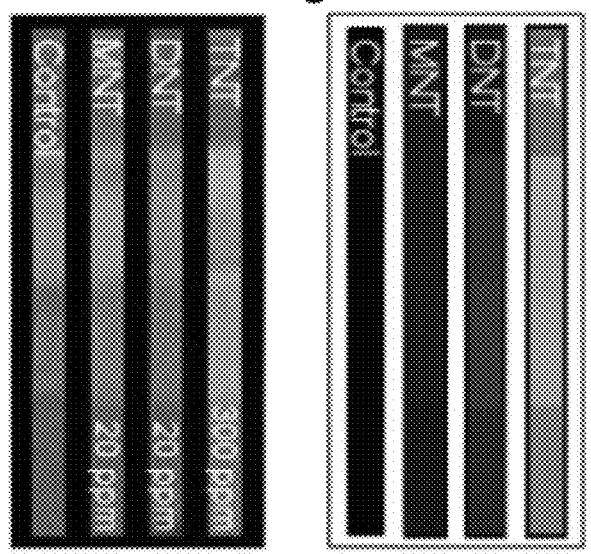
Figure 4D:
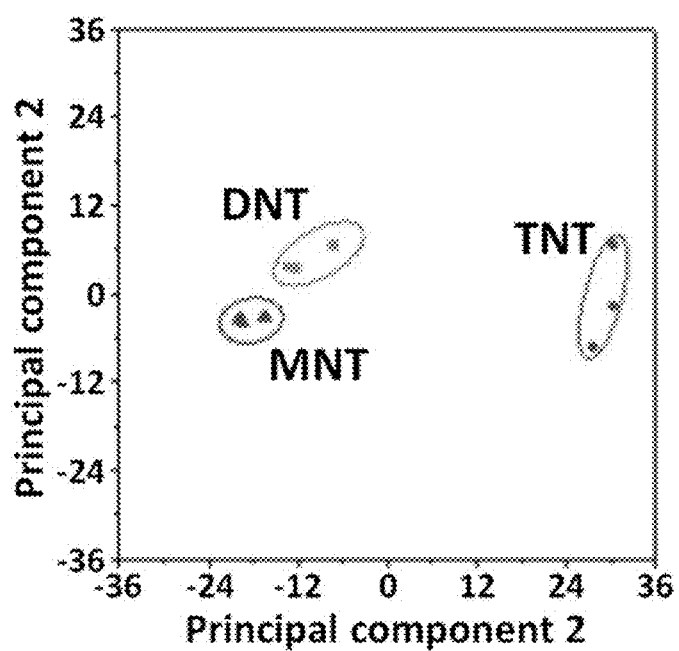
FIG. 4D) PCA plot of the color changes resulting from the exposure of the Phage litmus to TNT, DNT, and MNT.
Figure 5:
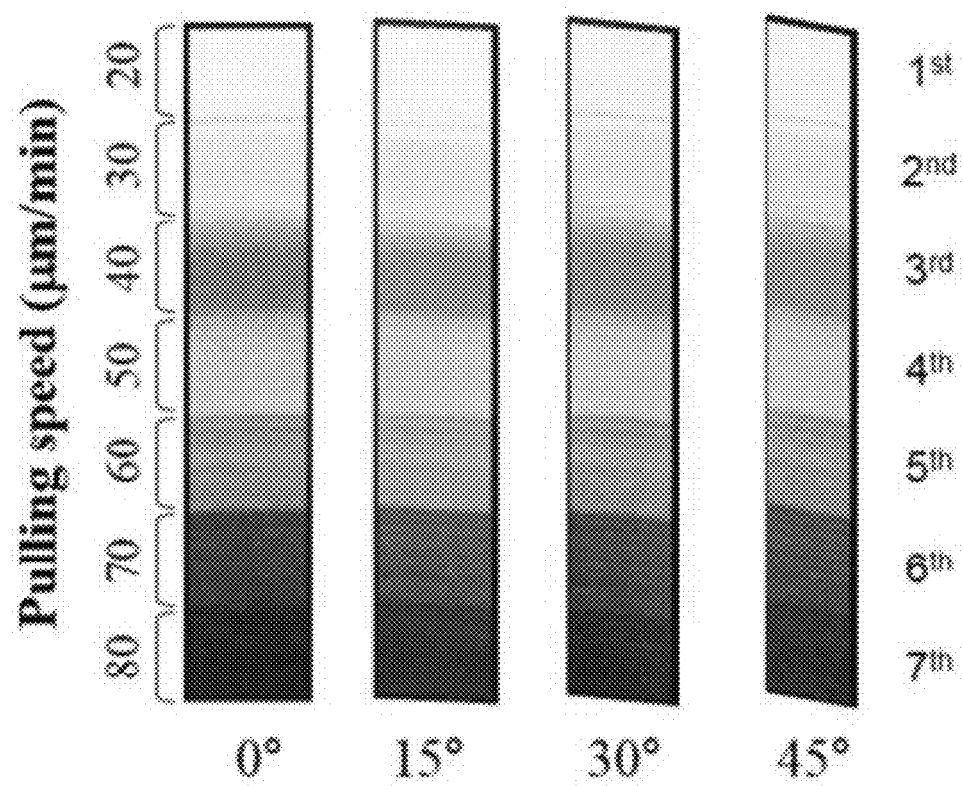
FIG. 5. Viewing angle independent color of Phage litmus composed of quasi-ordered phage bundle structures under omni-directional illumination. The Phage litmus matrix showed very little color change when viewed under omni-directional illumination regardless of viewing direction. This can be seen in photographs taken at viewing angles between 0° and 45°.
Figure 6A:
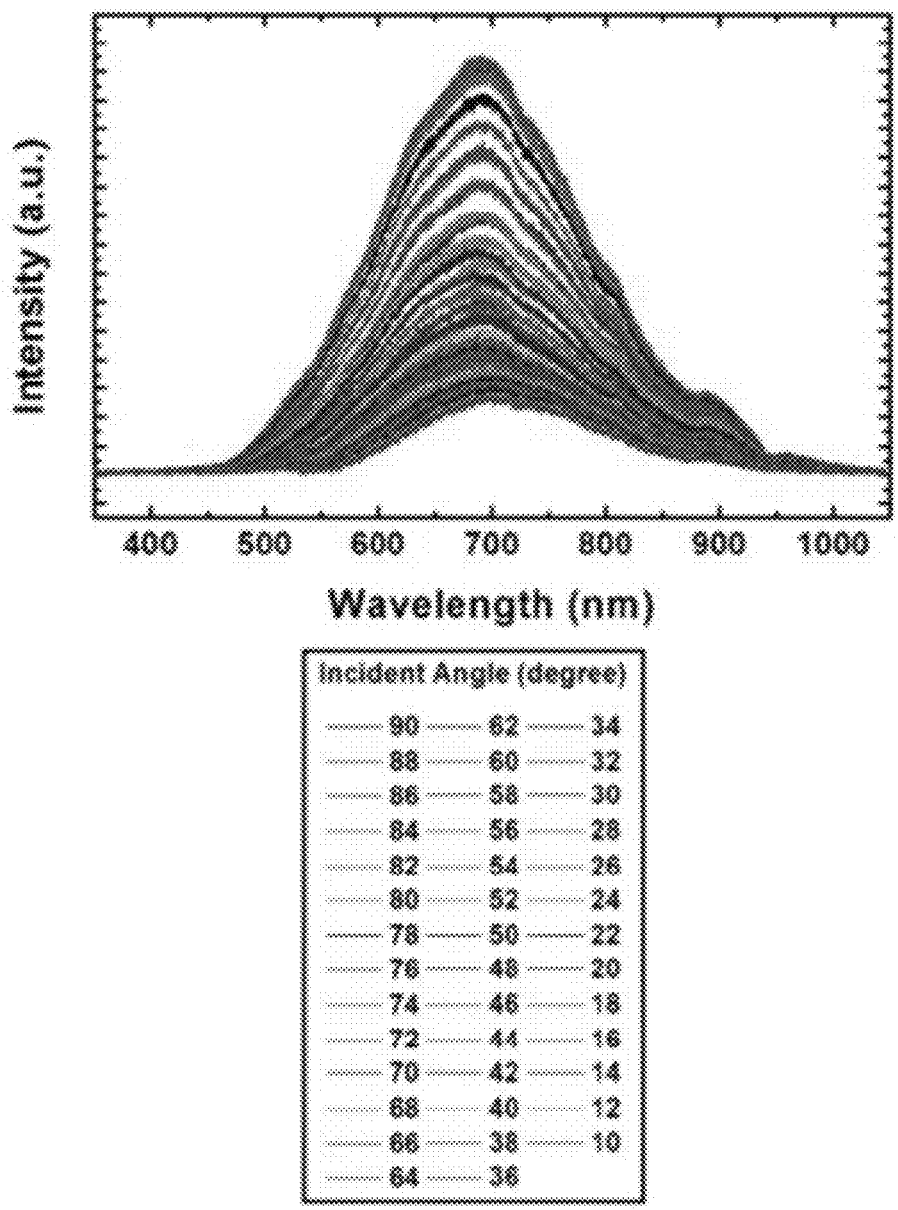
FIGS. 6A-6C show reflectance spectra of the Phage litmus under omni-directional illumination. The reflectance spectra of the Phage litmus matrix showed very little change in peak wavelength when measured under omni-directional illumination.
Figure 6B:
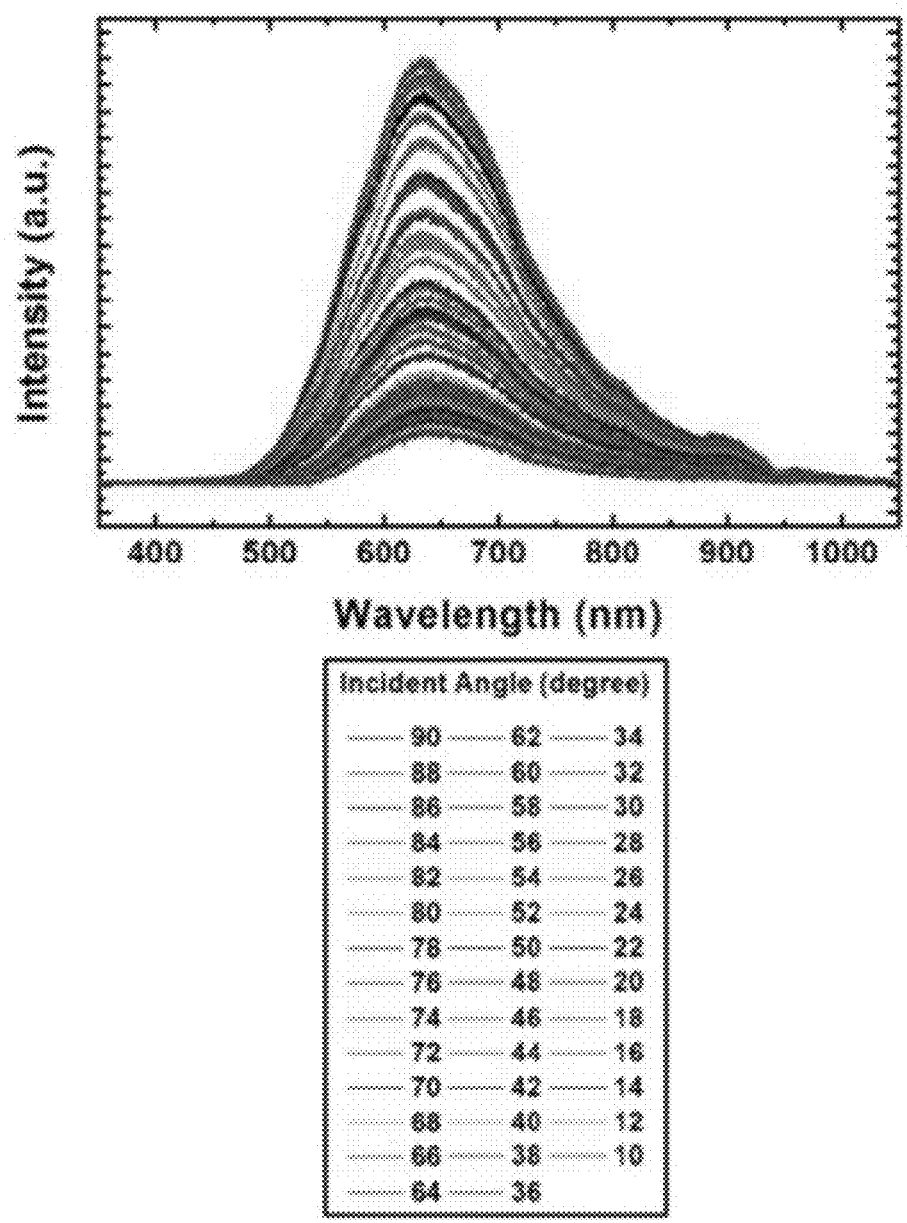
Figure 6C:
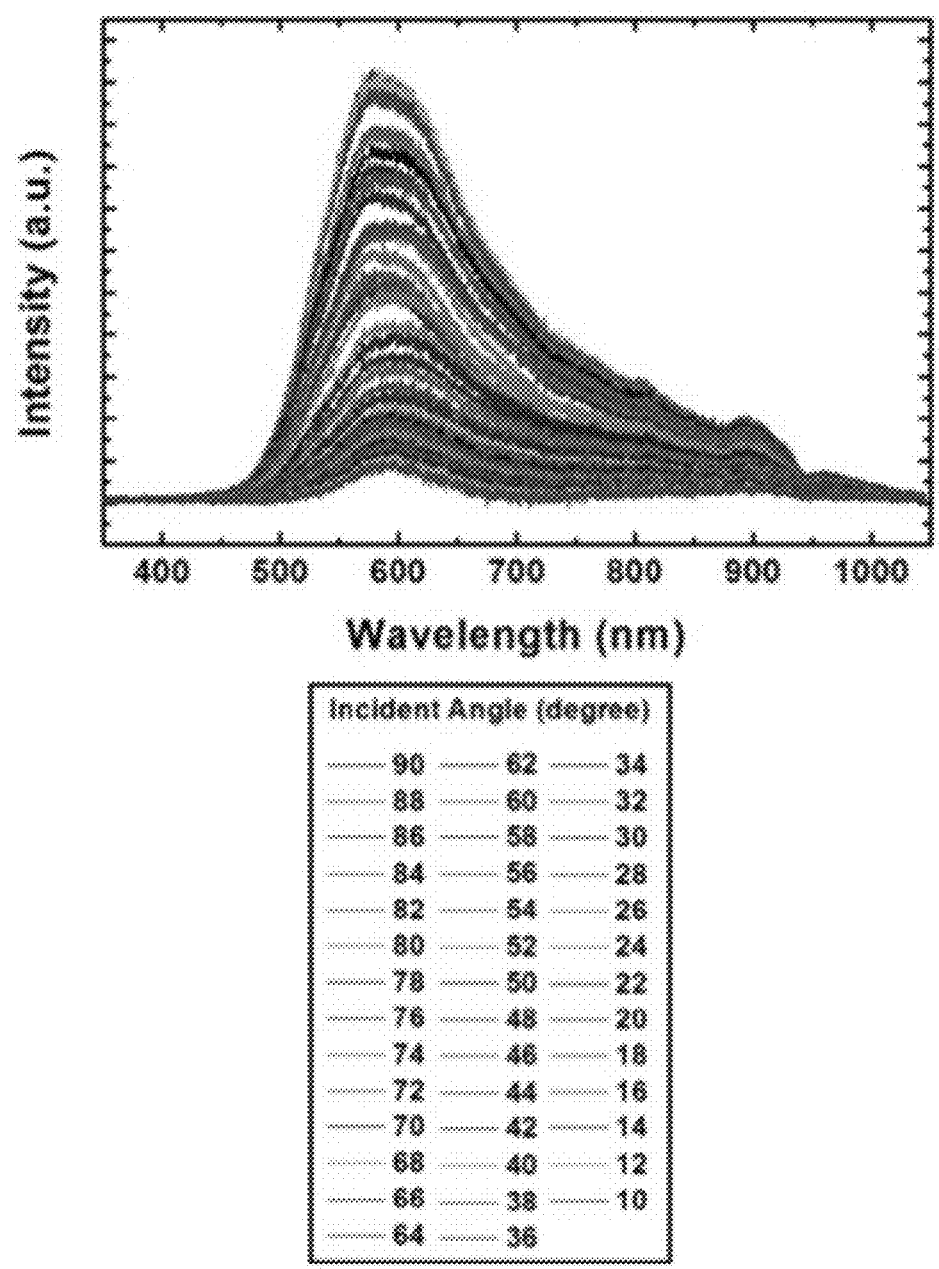
Figure 19A:
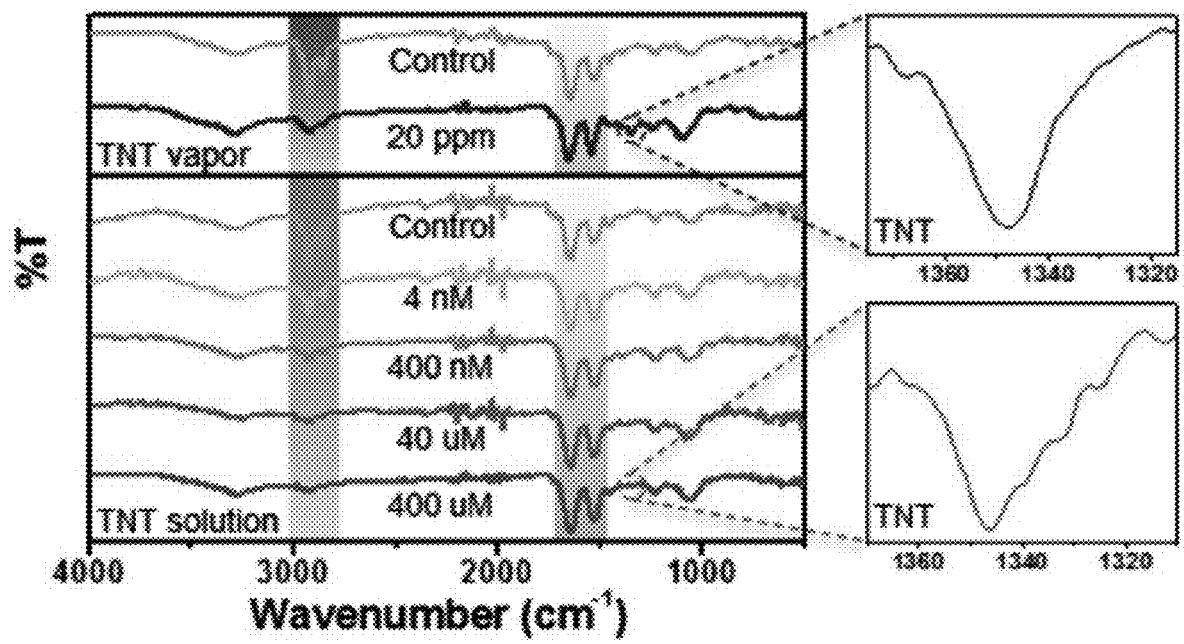
FIGS. 19A-19B illustrate specific binding between TNT-binding phage and TNT.
Figure 19B:
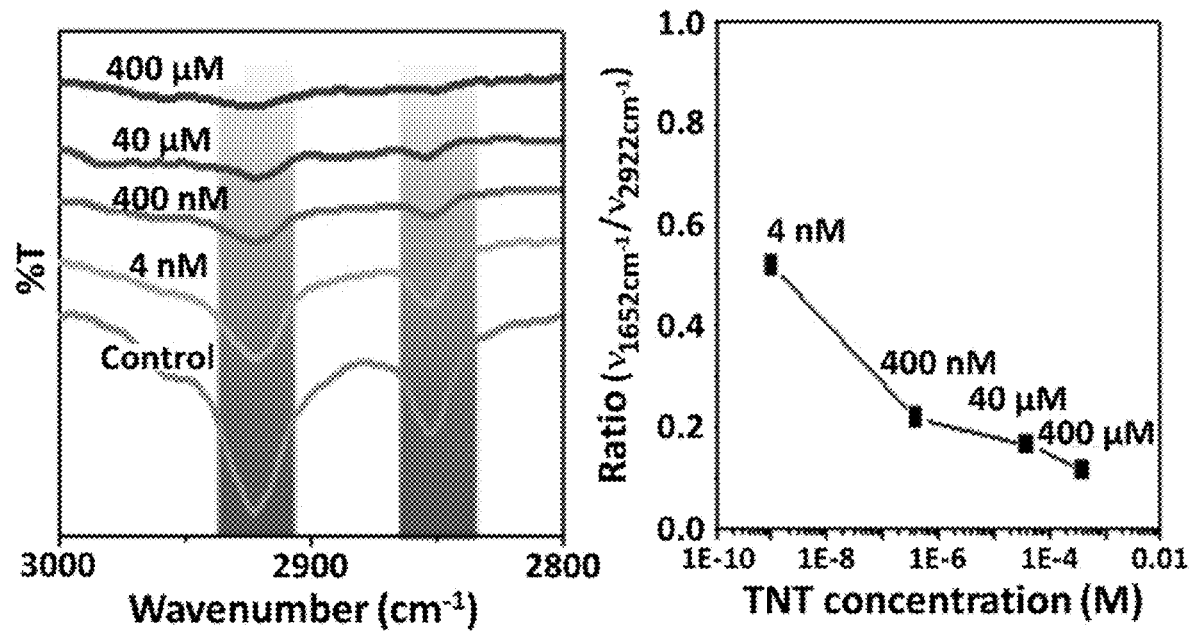
Figure 20A:
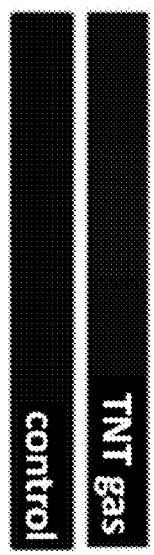
FIGS. 20A-20D show the results of a control experiment for TNT detection using the 4E-Phage litmus sensor in gas and liquid phases. There was negligible color change in (FIG. 20A) the TNT gas phase (20 ppm) and (FIG. 20B) the TNT liquid phase (400 μM) compared to that of the TNT-Phage litmus due to the lack of binding affinity. (c) RGB color patterns corresponding to the color fingerprints in FIG. 20A and FIG. 20B, respectively.
Figure 20B:
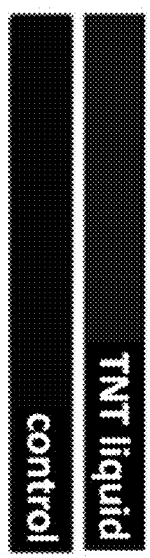
Figure 20C:
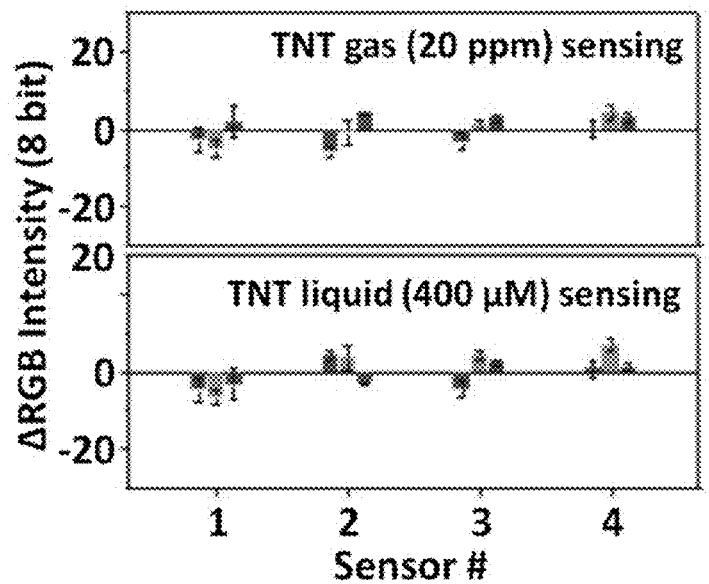
Figure 20D:
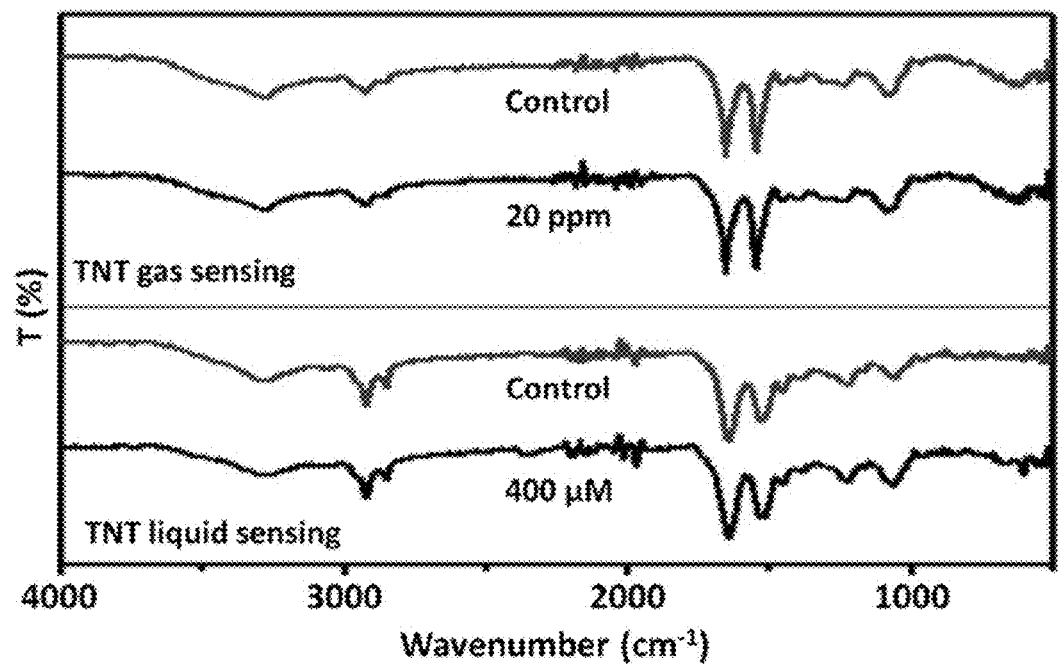
Figure 22:
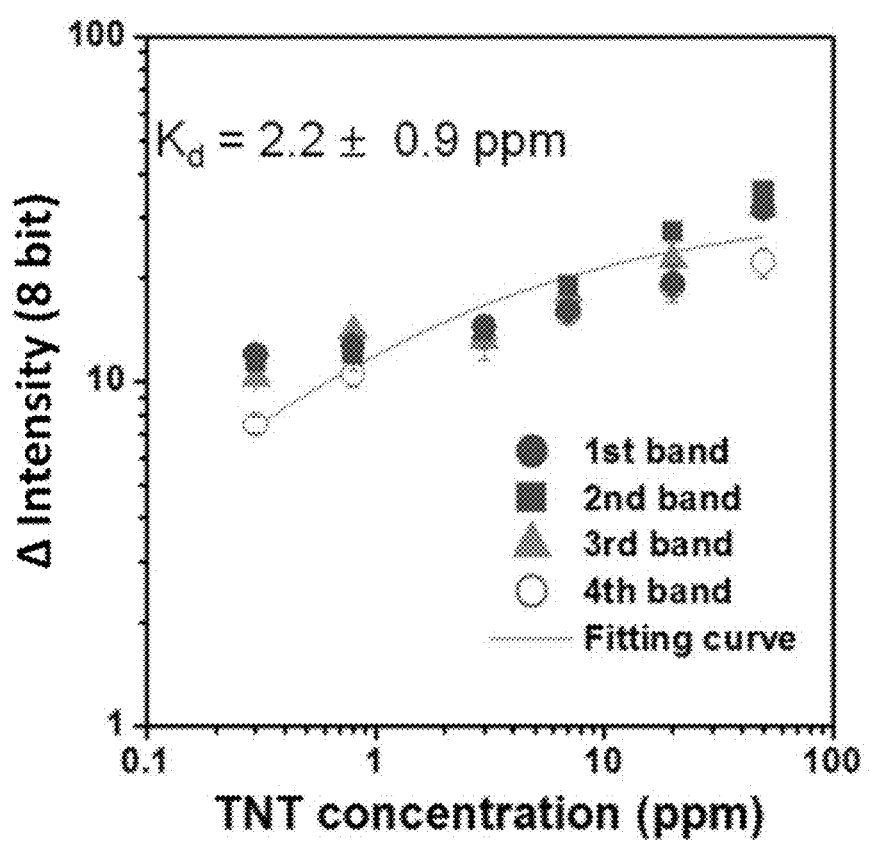
FIG. 22. Measurement of the dissociation constant ($K_d$) of the complex between TNT-Phage litmus and TNT. Data points (values for RGB intensity of main color at each matrix) are presented by blue closed circles ($1^{st}$), red closed circles ($2^{nd}$), green closed circles ($3^{rd}$), and green open circles ($4^{th}$), respectively. The solid red line is the calculated curve with the Hill's equation.
Figure 23:
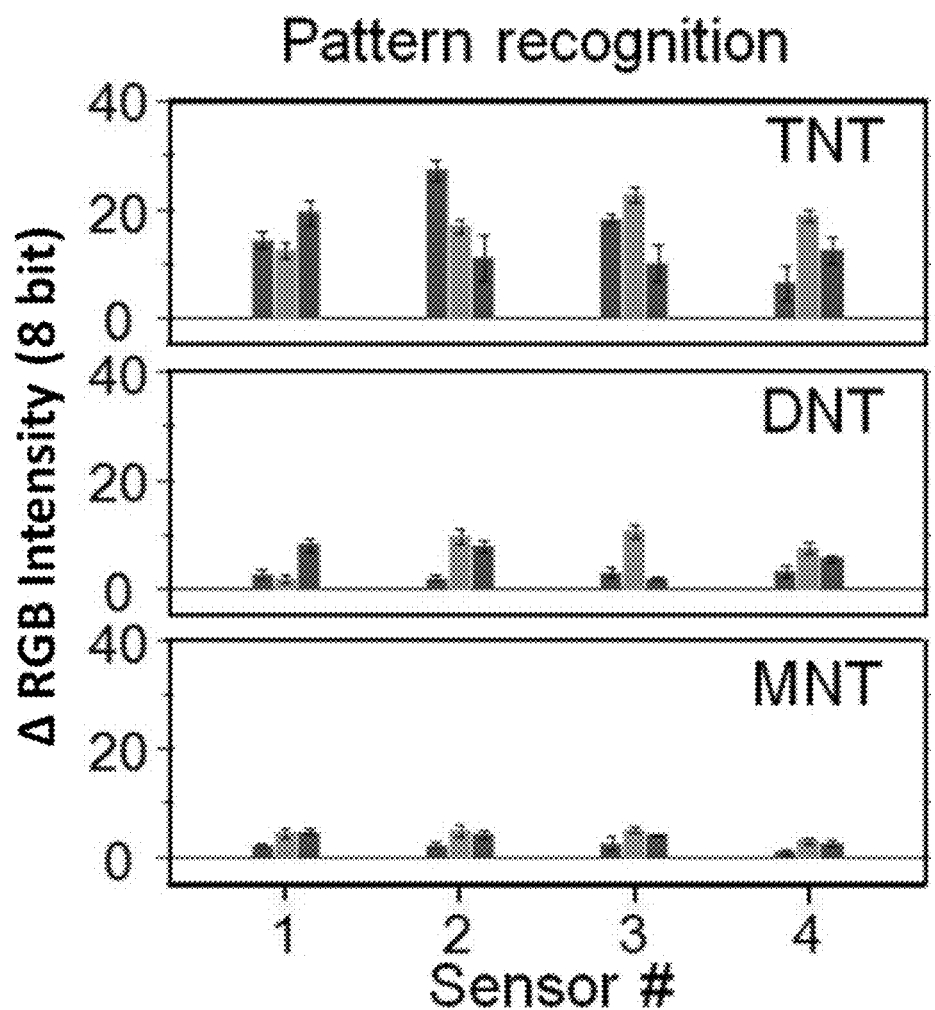
FIG. 23. RGB color patterns of the TNT-Phage litmus sensor response to TNT, DNT, and MNT. Upon exposure to TNT (20 ppm), DNT (20 ppm), or MNT (300 ppm) vapor, the TNT-Phage litmus responded selectively to the TNT molecules over similar chemical structures DNT and MNT.
Figure 24A:
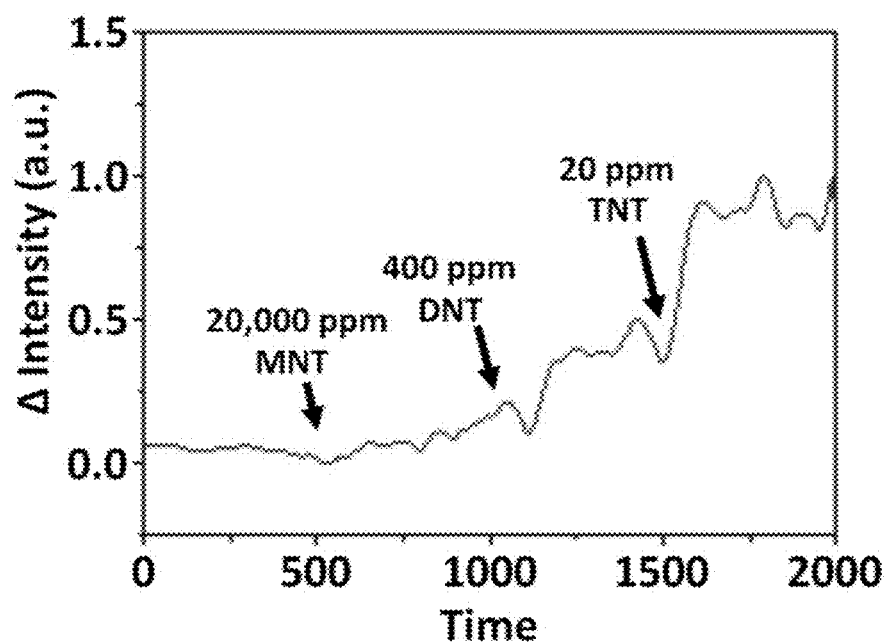
FIGS. 24A-24C illustrate selective response to TNT in mixtures of EtOH, MNT, and DNT.
Figure 24B:
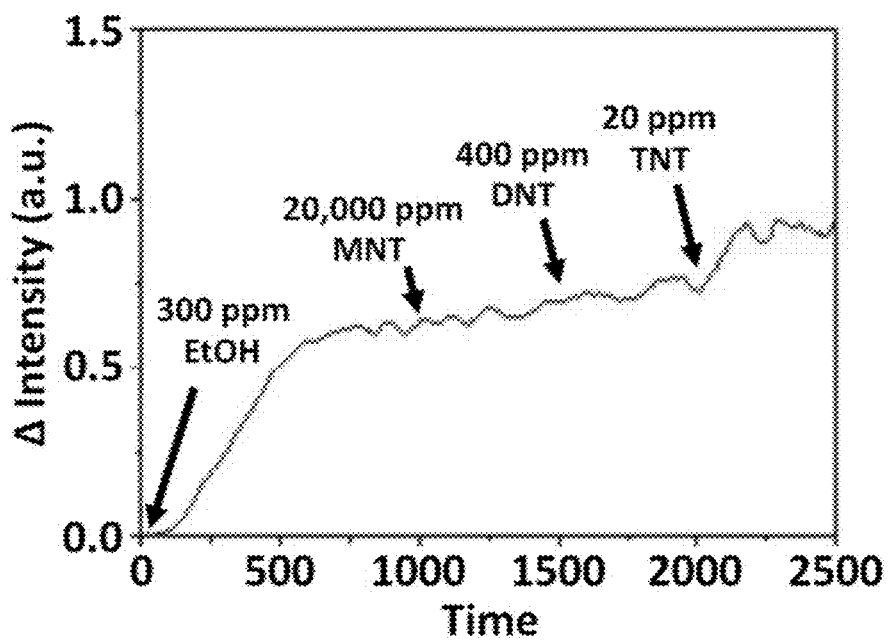
Figure 24C:
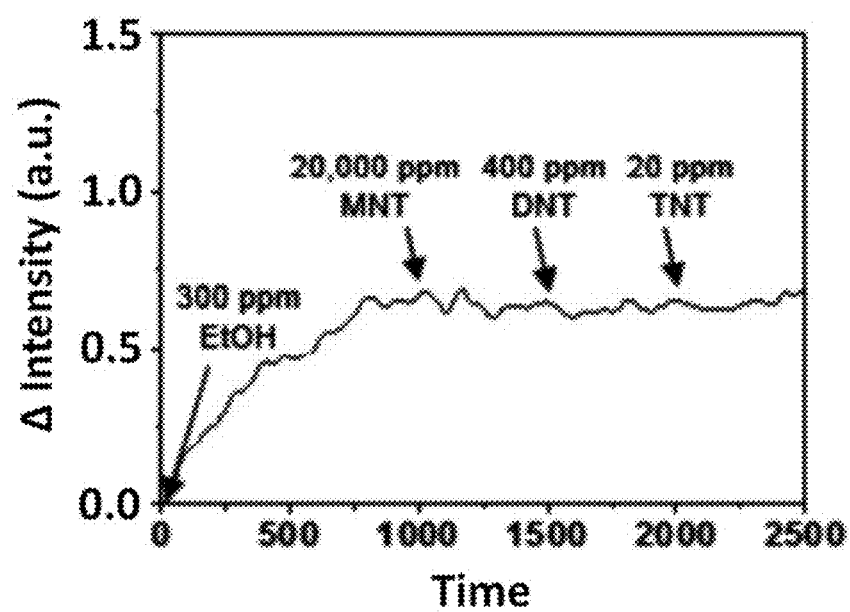

The M13 phage proved useful in detecting target materials with high selectivity and sensitivity, because target-specific phage can be identified through well-established phage display techniques[36-38]. We enhanced the selectivity of the Phage litmus by incorporating target specific binding motifs identified through directed evolutionary screening of a combinatorial, phage-displayed peptide library. Although the Phage litmus composed of wild-type M13 phage gives a characteristic response for the various VOCs which have high-vapor pressures, little color change was observed in response to low-vapor pressure organic compounds such as explosives or environmental toxicants. In order to demonstrate that such compounds could be specifically detected, we targeted TNT as a model explosive chemical. First, phages were engineered to display a TNT-binding peptide motif identified by phage display on their major coat proteins (DDWHWQEG, SEQ ID NO:3) (FIG. 4A)[39]. After confirming the specific binding capability of the TNT binding phage (TNT-phage) (FIGS. 17 & 17B), we constructed TNT phage-based colorimetric thin films (TNT-Phage litmus) and tested their TNT vapor sensing capabilities. Upon exposure to TNT vapor, the TNT-Phage litmus exhibited sensitive and selective color changes. As the concentration of applied TNT vapor increased, the TNT-Phage litmus showed pronounced color changes due to structural changes induced by TNT binding (FIGS. 18A & 18B) and, as observed in the previous organic vapor experiments, the color bands with wider diameter fiber bundles had more pronounced responses compared to those with narrower diameters. We believe that the color changes resulted from structural modifications to the phage matrices induced by binding with the nitro-aromatic analyte of interest. We confirmed TNT binding to TNT-Phage litmus through Fourier transform infrared spectroscopy (FT-IR) analyses (FIGS. 19A & 19B). When we exposed a Phage litmus composed of control-phage displaying four glutamates (4E) to TNT, there were neither significant color changes nor FT-IR spectrum changes (FIGS. 20A-20D). In order to enhance the accuracy and convenience of colorimetric analysis, we exploited the photographic and computational functions of common handheld devices (i.e., iPhones). We utilized the device's camera and a home-built analysis application, which we termed iColor Analyzer, to produce 8-bit red-green-blue (RGB) color components that can be used to easily quantify the color change in each band of our sensors). Using the iColor Analyzer, we could detect down to 300 ppb of TNT in the gas phase (FIG. 4B and FIG. 21). We obtained a dissociation constant ($K_d$) of 2.2 ppm for the TNT-phage interaction with TNT (FIG. 22). In order to test the specificity of the phage matrices, we applied chemicals with similar structures to TNT (i.e., DNT and MNT). Upon exposure to TNT (20 ppm), DNT (20 ppm), and MNT (300 ppm) vapor, the TNT-Phage litmus showed selective response to the TNT molecules, more than three and five times higher compared to DNT and MNT, respectively (FIG. 4C and FIG. 23). A two-dimensional PCA plot supported the discrimination capabilities and reproducibility of the TNT-Phage litmus sensor (FIG. 4D). The first two principal components account for 97.2% of the variance in the three measurements of each chemical. Through the pattern recognition process, we could distinguish the target TNT, DNT, and MNT down to 300 ppb using our iColor Analyzer system. We performed experiments in mixed vapors of ethanol, MNT, DNT, and TNT, to test the specificity of our TNT-Phage litmus sensor in the presence of interfering molecules. The TNT-Phage litmus showed negligible responses to relatively large amounts of MNT (20,000 ppm) and DNT (400 ppm), while addition of 20 ppm TNT vapor caused a significant color change (FIG. 24A). In a 300 ppm ethanol background, the TNT-Phage litmus also responded selectively to TNT molecules (FIG. 24B). This result demonstrates that our system selectively distinguishes TNT over other molecules with similar chemical structure in the presence of interferents. When our Phage litmus might exhibit a response to real-world interferents like humidity or common VOCs, we can exclude non-specific responses by comparison to the response of a non-sensitive Phage litmus. For example, the 4E-phage litmus was non-responsive to TNT in the presence of ethanol, MNT, and DNT (FIG. 24C).

Discussion

We developed a facile, biomimetic, colorimetric sensing system to detect explosive molecules in a selective manner by exploiting the advantageous features of phage: their abilities to replicate, self-assemble, and evolve. Our sensing matrices possess multiple advantages over conventional biosensors: First, we can easily fabricate multiple colorimetric matrices with tunable colors through a one-step self-assembly process. Importantly, these self-assembled matrices exhibit viewing-angle independent colors. Second, we can tailor the function of the phage matrices through directed evolution for specific analyte of interest and directly incorporate the target recognition motifs by genetic engineering. Furthermore, we can produce large-area multi-color matrices that are readable by a common handheld device. Our sensitive and selective colorimetric phage matrix sensors promise to establish rapid, portable, and simple sensing. Although the TNT sensing system was used as proof-of-concept in this study, this approach can be generalized to the detection of many harmful chemicals and biological toxicants.

Methods

Genetic Engineering of Phage.

Our group identified a TNT-binding peptide sequence (WHWQ) using phage display with a commercially available 12mer linear peptide library (Ph.D.™-12)[37, 39]. In order to incorporate the TNT binding peptide, we genetically engineered the M13 phage's major coat proteins (pVIII). The desired peptide sequences were inserted between the first and the sixth amino acids of the N-terminus of wild type pVIII, replacing residues 2-5 (Ala-Glu-Gly-Asp-Asp-Pro (SEQ ID NO:4) to Ala-(Insert)-Pro (SEQ ID NO:5)[32]. In order to incorporate the most stable phage to carry the consensus TNT binding peptide (WHWQ, SEQ ID NO:6) identified by phage display, we designed a partial library with sequence of the form AXX*WHWQ* XXDP (SEQ ID NO: 7) using the primer: 5'-ATATATCTGCAGNKNNK *TGGCATTGGCAG* NNKN NKGA TCCCGCAAAAGCG-GCCTTTAACTCCC-3' (SEQ ID NO:8) and the primer 5'-GCTGTCTTTCGCTGC AGAGGGTG-3' (SEQ ID NO:9) to linearize the vector (N=A/C/G/T and K=G/T). To incorporate the gene sequences, polymerase chain reaction (PCR) was performed using Phusion DNA Polymerase, two primers (insertion and linearization), and an M13KE vector with an engineered PstI site as the template. The obtained product was purified on an agarose gel, eluted by spin column purification, digested with PstI enzyme, and recircularized by an overnight ligation at 16° C. with T4 DNA Ligase. The ligated DNA vector was transformed into XL1-Blue electroporation competent bacteria, and the amplified plasmid sequence was verified at the University of California, Berkeley DNA sequencing facility. The pVIII library was screened against TNT and the resulting sequences were tested for stability after large-scale amplification. The library member, ADDWHWQEGDP (SEQ ID NO: 1) was finally chosen to create our TNT Phage litmus sensors. Alanine-substituted control phage (WAW, AHW, WHA) sequences were synthesized by site-directed mutagenesis of the WHW-phage. Using similar genetic engineering approaches, we constructed EEEE (4E)-phage as a control. The constructed phages were amplified using bacterial cultures and purified through standard polyethylene glycol precipitation. The phage solution was further purified by filtration through 0.45 m pore size membranes. To verify phage stability, DNA sequences were confirmed at each step of the amplification.

Fabrication of Phage Litmus.

We created the phage self-assembled color band patterns using a simple pulling method[25]. The colors of the assembled structures were varied by controlling the pulling speed between 20-80 μm/min. We constructed a home-built phage deposition apparatus by modifying a syringe pump. We programmed software using C++ to control the motor speed (between 0.1 μm/min-30 mm/min) through an RS232C cable. For preparing Phage litmus matrices, we used 6 mg/mL 4E-phage suspensions in tris buffered saline (TBS) (12.5 mM tris and 37.5 mM NaCl, pH 7.5) or 2.4 mg/mL WHW-phage suspensions in DI-water, respectively. A spectrum of colored bands (each band was obtained at a different pulling speed) was clearly perceptible when the matrices were deposited on gold-coated Si wafers.

Turkey Skin Sample Preparation.

Fresh turkey head samples were donated from a local turkey farm (Pitman Farms, Sanger, Calif.). The heads were obtained through overnight delivery immediately after they were slaughtered. The fresh turkey skin samples were immediately taken and processed for optical microscopy and transmission electron microscopy. For histology, ~0.5 cm×1 cm turkey skin samples were soaked in 20% sucrose in PBS for 2 hours, embedded in OCT Compound (Sakura, Torrance, Calif.), cryosectioned at 5 m thickness (Shandon cryostat, Asheville, N.C.), and stained with Masson's trichrome. Images were collected using an IX71 Microscope (Olympus, Tokyo, Japan). TEM samples were fixed with 2% glutaraldehyde in 0.1 M sodium cacodylate (pH 7.2) for 1 hour, post-fixed with 1% osmium tetroxide in 0.1 M sodium cacodylate (pH 7.2), and rinsed three times with sodium cacodylate (pH 7.2). Dehydration was done using a graded ethanol series (20%, 40%, 60%, 80%, 100%, and 100%) followed by step-wise infiltration with epon-araldite resin (2 parts acetone/1 part resin for 1 hour, 1 part acetone/1 part resin for 1 hour, 1 part acetone/2 parts resin for 1 hour, 100% resin for 1 hour, 100% resin overnight, 100% resin with BDMA for 1 hour) and heat polymerized in a 60° C. oven. Sample blocks were sectioned at 90 nm using a Leica EM UC6 microtome (Leica Microsystems Inc. Buffalo Grove, Ill.). Grids were stained with 2% uranyl acetate and Reynolds' lead citrate. Imaging was done using a FEI Tecnai 12 transmission electron microscope (FEI, Hillsboro, Oreg.).

Atomic Force Microscopy (AFM) Analysis of Phage Litmus.

AFM images were collected using an MFP3D AFM (Asylum Research, Santa Barbara, Calif.) and analyzed using Igor Pro 6.0 (WaveMetrics, Inc., Lake Oswego, Oreg.) and Asylum software package (Asylum Research, Santa Barbara, Calif.). All images were taken in tapping mode with a tip spring constant of 2 N/m. The probe tips (Ted Pella, Inc., Redding, Calif.) were made of silicon with a 10 nm radius. The humidity experiments were carried out in a closed liquid cell. We injected a fixed quantity of DI-water to control the humidity. Fast Fourier Transform (FFT) analysis of AFM cross-sectional height profiles was used to determine the periodicity of the self-assembled nanofilament structures within the Phage litmus matrices. Numerical computation of the Fourier transform was done with a 2D FFT algorithm in OriginPro 8 (Origin Lab Corp. Northampton, Mass.) and imageJ v1.44p (National Institutes of Health). We calculated the Fourier power spectra expressed in spatial frequency ($\mu m^{-1}$) from the AFM images.

Reflectance Measurements of Phage Litmus.

Figure 25:
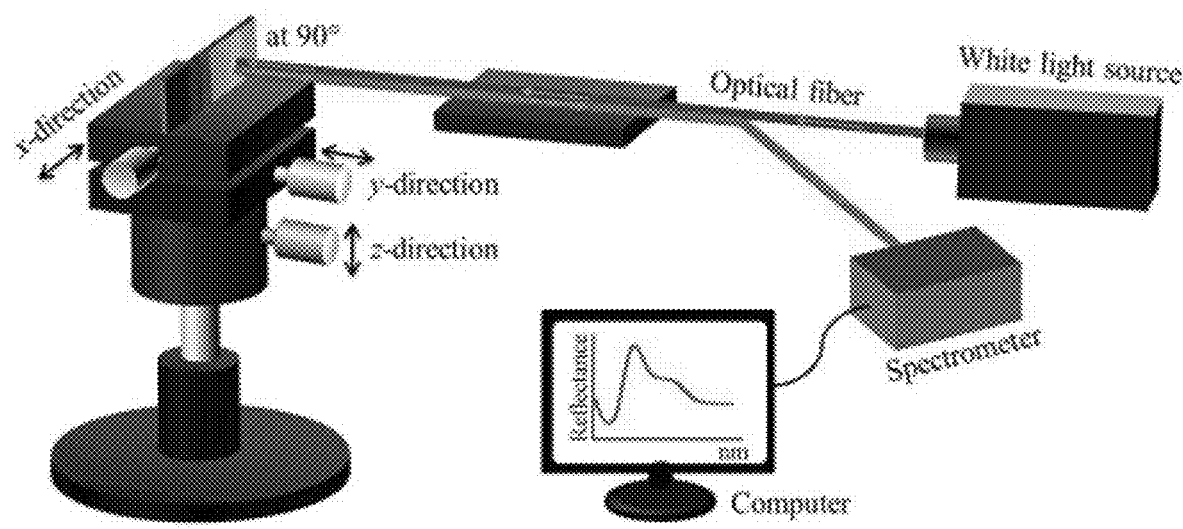
FIG. 25. An exemplary experimental setup used for reflectance measurements.

Phage litmus matrices were illuminated by a white light source of a Xenon lamp (X-Cite, Exfo, Mississauga, Canada) and the reflected spectra were obtained using a fiber optic spectrophotometer (USB4000, Ocean Optics, Dunedin, Fla.) through a Y-shaped bifurcated optical fiber (FIG. 25). An optical fiber fixed on an x-y-z stage was positioned normal to the Phage litmus surface and perpendicular to the scanning direction. Reflectance was measured using a gold coated Si wafer as a reference. The humidity experiments were performed in a closed glove box (Plas Labs, Inc., Lansing, Mich.). The humidity was controlled by DI-water and monitored using a hygrometer (VWR International Inc., West Chester, Pa.).

Reflectance Measurements of Phage Litmus with Different Incident Angle.

Figure 26:
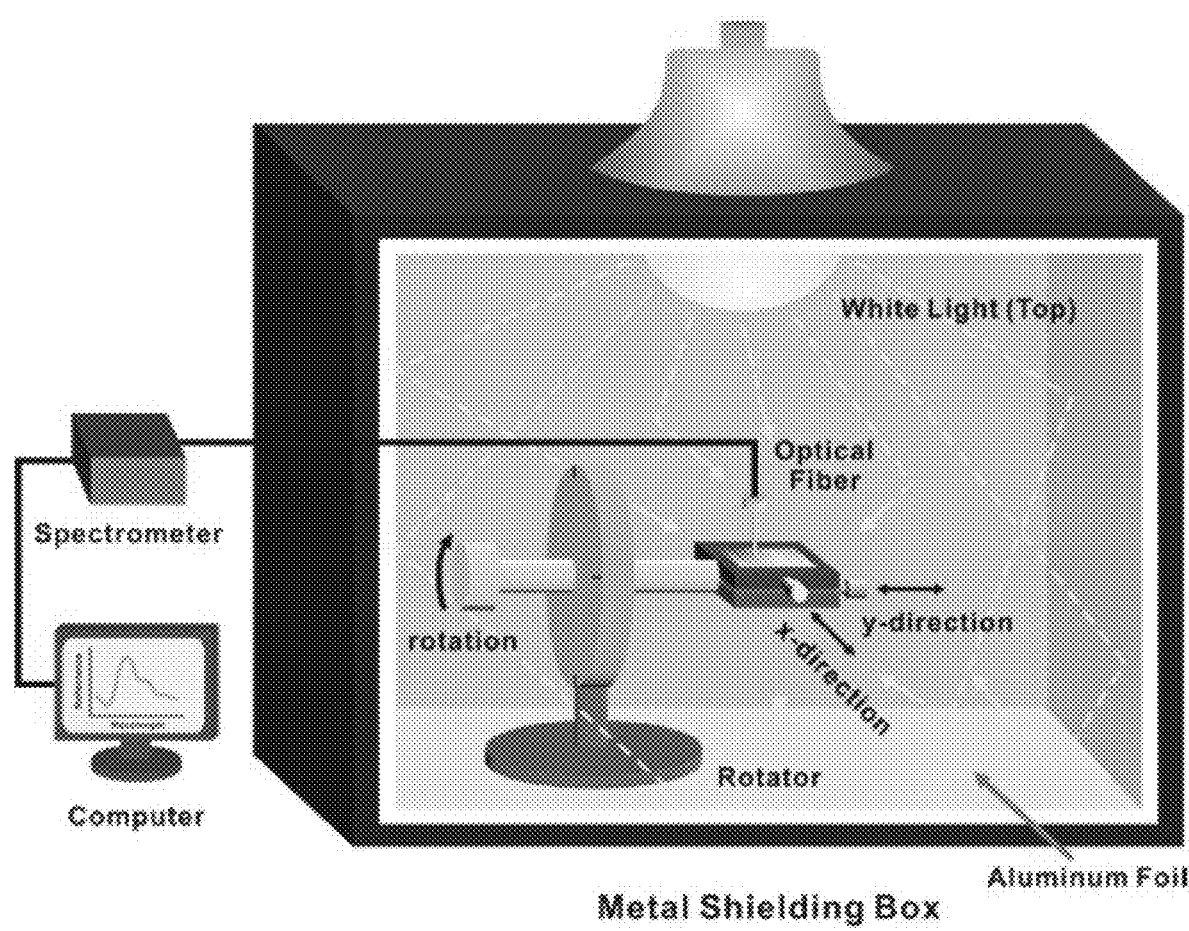
FIG. 26. An exemplary experimental setup used for angle-dependent reflectance measurements with omni-directional lighting.
Figure 27A:
FIGS. 27A-27C illustrate an exemplary iColor Analyzer Program.
Figure 27B:
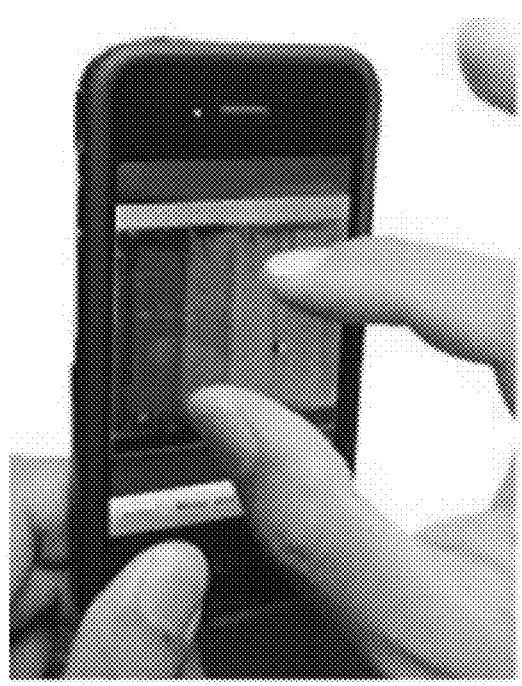
Figure 27C:
Figure 28A:
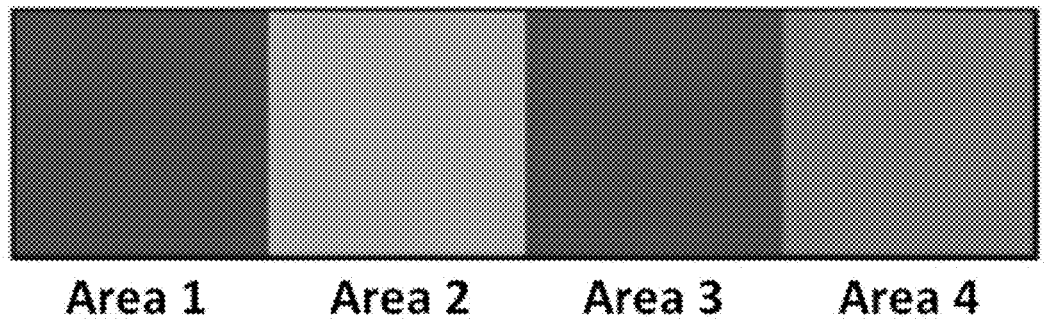
FIGS. 28A-28B illustrate an exemplary iColor Single Channel Mode.
Figure 28B:
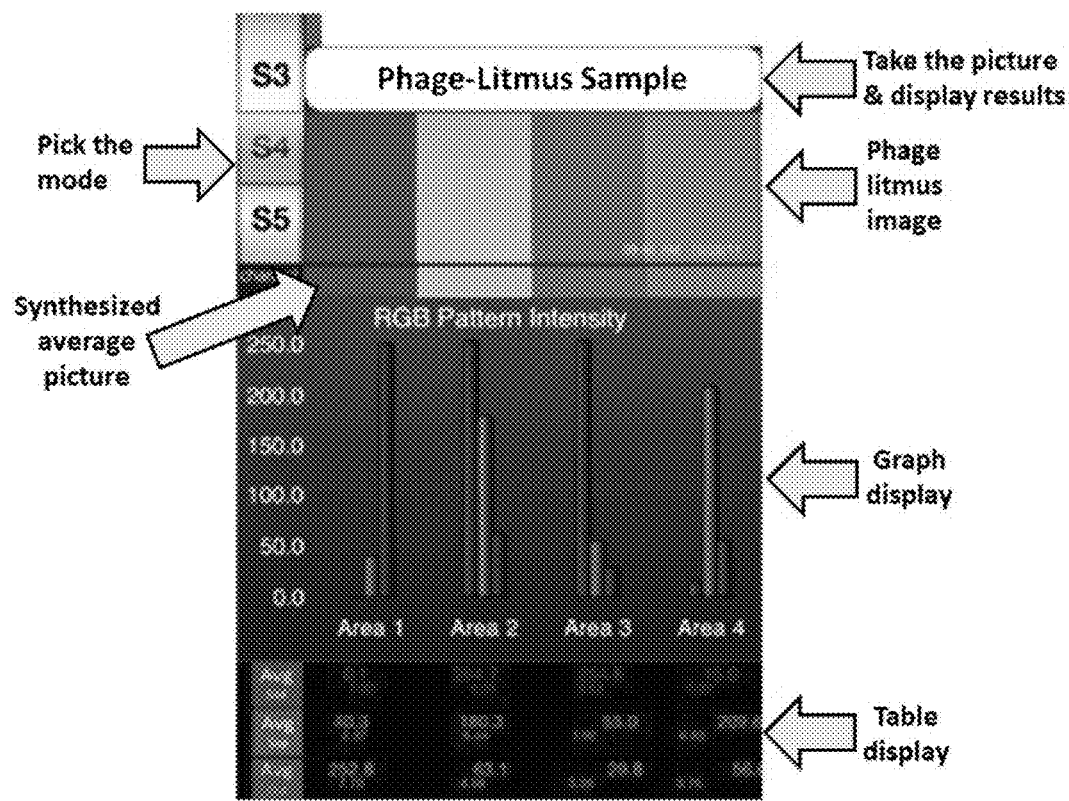
Figure 29A:
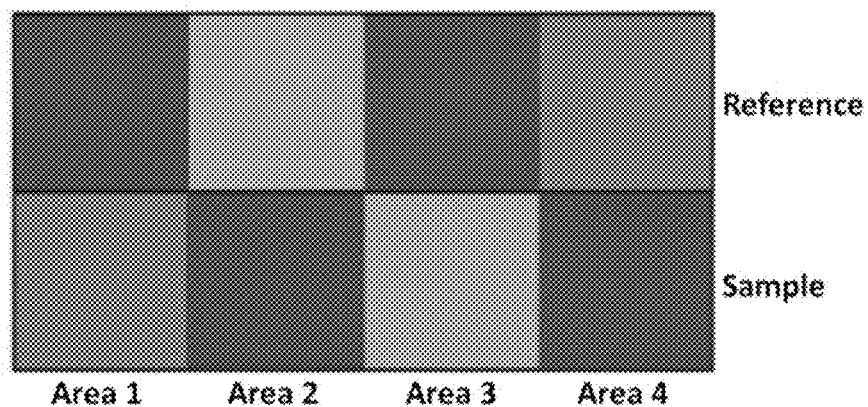
FIGS. 29A-29B illustrate an exemplary iColor Double Channel Comparison Mode.
Figure 29B:
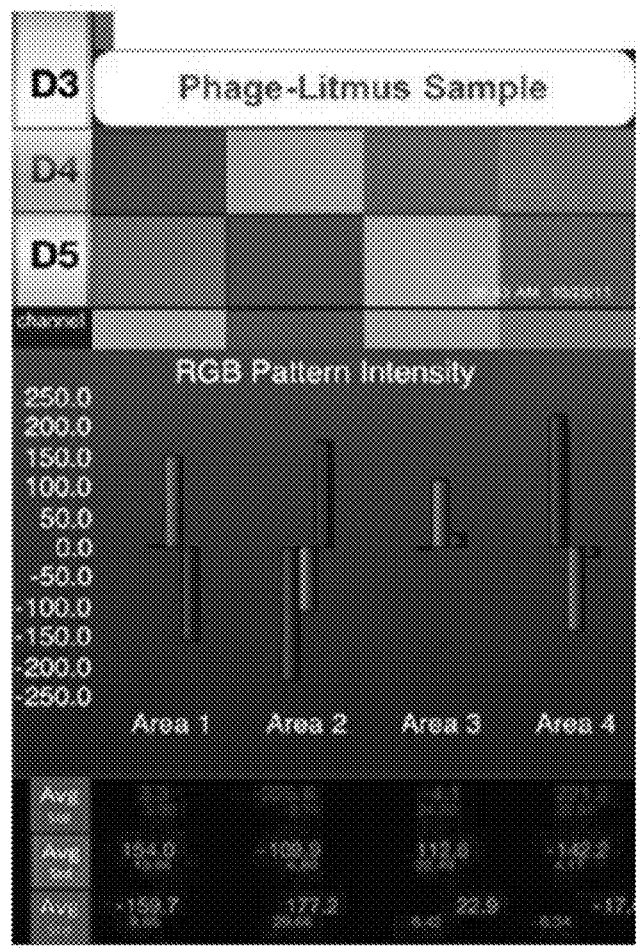
Figure 30:
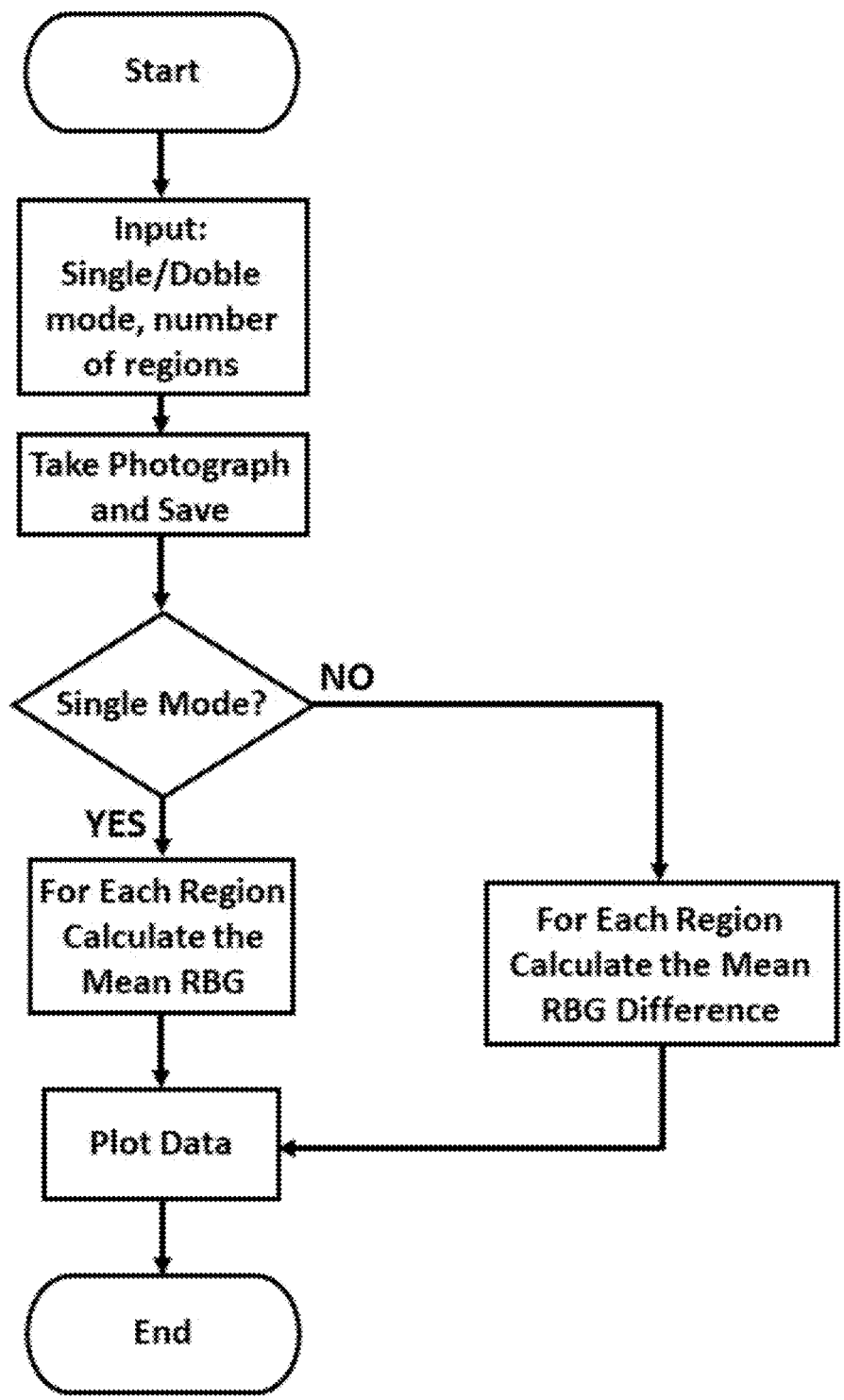
FIG. 30 shows an exemplary iColor workflow. 1. App starts 2. The user selects between input mode S1~S5, D1~D5 (S/DX denotes single/double sample mode, and the number X denotes the number of regions). At this stage, the regions on the image from which the RGB data will be calculated are defined. 3. The user takes the image of one (the sample) or two samples (the reference and the sample), according to which mode (S/D) the user selected. All the functions of the basic imaging software like light on/off are available. 4. The user expands or contracts and drags the image taken at so that the image fills the guiding window and the regions to be analyzed are aligned. 5. For each row (reference, sample) and for each region (X), the app calculates the mean value of the RGB values (and their standard deviation) if single mode, and the mean values of the difference of RGB between reference and sample if using double mode. 6. The report displays for each region the mean value of the RGB if single mode, and the mean values of the difference of RGB between reference and sample if double mode in table and bar graphs. 7. Saves the screenshot of the reporting image. 8. App ends.

In order to characterize the reflectance spectra of the Phage litmus under omni-directional illumination, we lit a box coated with aluminum foil with a lamp (Incandescent Light, 150 W, DWC Sylvania, U.S.A) (FIG. 26). We characterized the reflectance spectra while rotating the substrate between 10 and 90 degrees from horizontal. A gold coated Si wafer was used as a reference.

Grazing Incidence Small Angle X-Ray Scattering.

To characterize the swelling behavior of the Phage litmus, we performed in situ grazing incidence small-angle X-ray scattering (GISAXS) experiments before and during exposure to humidity (~3 mL of deionized water in a closed chamber). The GISAXS data were collected at the beam line 7.3.3 at the Advanced Light Source at Lawrence Berkeley National Laboratory. X-rays with a wavelength of 1.23984 Å (10 keV) were used, and the scattering spectra were collected on an ADSC Quantum 4u CCD detector with an active area of 188 mm×188 mm (2304×2304 pixels). The scattering profiles were obtained after a 60 s collection time by integrating the 2-D scattering pattern. The sample to detector distance was 1.84791 m, and the incidence angle was 0.14 degrees. Line-averaged intensities were reported as I versus q, where $q=(4\pi/\lambda)\times \sin(\theta/2)$, $\lambda$ was the wavelength of incident X-rays, and $\theta$ was the scattering angle.

MATLAB Based Analysis System for Real Time Analysis of Phage Litmus.

A home-built sensing and analysis system was developed for real time chemical sensing. The equipment setup consisted of a gas chamber with an optical opening where a digital microscope (Celestron LLC, Torrance, Calif.) was attached to monitor the color of the Phage litmus. The chamber with the Phage litmus inside was positioned on top of a heat block to control the temperature of the chamber. A MATLAB program (Mathworks Inc. Natick, Mass.) was run on a PC to control the camera settings; to perform real-time readout and processing of the captured images, and to display the real-time RGB data. First, the automatic gain of the digital microscope was turned to manual mode and a fixed gain was retained to prevent unwanted automatic compensation of brightness. The number of regions of interest, usually matching the number of different color bands on the Phage litmus, was input by keyboard. Then, the specific regions to compare were selected from the first image (reference image) by mouse input. The subsequent images were taken and saved according to a pre-set frame rate (usually every 5 sec). The change of the average RGB values with respect to the reference image for each region of interest was calculated and displayed on a graph in real-time. We provide typical code from which we performed our experiments in Table 2. The vapor phase experiments were performed by injection of a volume of solvent needed to achieve 300 ppm concentration into a small container inside the chamber through an inlet tube. For explosive exposure experiments, we put excess amounts of each explosive crystal (200 mg) in a sealed chamber (20 mL) and controlled the vapor pressures by temperature. We obtained the concentration of all compounds based on the vapor pressure at each temperature with the assumption of vapor ideality. The vapor pressure of TNT, DNT, and MNT was obtained from previously reported values (References 40-42). In order to collect the data at saturated conditions, we held the Phage litmus in the sealed chamber for 30 min and then obtained corresponding sensing results. In order to test the specificity of our TNT-Phage litmus sensor toward interfering molecules, experiments were performed in mixed vapors of MNT, DNT, and TNT. First we put the small sealed chambers (1 mL) containing excess amounts of each explosive crystal (200 mg) in a large chamber with the phage litmus. Then, we exposed the chambers to MNT, DNT, and TNT vapors sequentially using needles to open each small chamber (FIG. 24A). A similar setup was used to perform the same experiments in a background of ethanol vapor (FIG. 24B). We performed the control experiments using a 4E-Phage litmus sensor (FIG. 24C).

TABLE 2

MATLAB code

| Line | Code Description |
|---|---|
| 1-4 | Constructs 'vid' video input object to access the camera, sets the ReturnedColorspace property to RGB, and defines 'src' parameter to access 'vid' object |
| 5-7 | Sets the exposure mode to manual. In this way we can set manually the exposure and brightness of the camera. Note that the camera is set to auto exposure mode in default and will adjust the exposure and brightness automatically to medium exposure according to ambient light change and sample color/brightness change. The accessible camera parameters can be found by using get(src) command |
| 8 | Starts the timer for the 'vid' video input object |
| 10 | Waits a few seconds to stabilize the camera image |
| 12-15 | Receives from the user the parameters for image sampling interval, total image recording time, the output file name, and calculates the total frame number 'fnumber' |
| 17-19 | Takes and saves the image for the reference image from which the change of RGB will be calculated |
| 21-23 | Receives from the user the number of segments (regions), and informs the user to mouse click each segments from the referece image |
| 25-28 | Creates and visualizes the selected regions from the mouse input. Each selected region is in rectangle shape defined by to diagonally placed points (starting point, final point) |
| 31-34 | Calculates and saves into array the coordinates of the diagonal points of each segment from the reference image |
| 36-37 | Informs the user that the program can be stopped by pressing Stop |

TABLE 2-continued

MATLAB code

| Line | Code Description |
|---|---|
| 39-70 | For each frame, for each segment, and for each color (R, G, B) the difference in RGB for each segment is calculated, the mean value of RGB values is calculated the data is plotted and saved into file Note Line 47. Here, the difference between the current image and reference image is calculated. In this way, we can visualize both the increase and decrease of the RGB values. |
| 72 | Closes the figures |
| 74-76 | Stops the video input object, closes the camera preview, and clears 'vid' from memory |

In an experiment, Lines 1-4 were executed only once, while Lines 5-72 were executed as needed. Only when closing the program, were Lines 74-76 executed.

TABLE 3

Typical Matlab Code Example.

| Line | Code |
|---|---|
| 1 | vid = videoinput('winvideo', 1,'YUY2_320x240'); |
| 2 | set(vid, 'ReturnedColorspace', 'RGB'); |
| 3 | preview(vid) |
| 4 | src=getselectedsource(vid); |
| 5 | set(src,'ExposureMode','manual'); |
| 6 | set(src,'Exposure',-5) |
| 7 | set(src,'Brightness',30) |
| 8 | start(vid); |
| 9 |  |
| 10 | pause(3); % In seconds. To stabilize image |
| 11 |  |
| 12 | interval=input('Type the time interval (sec):') |
| 13 | total_time=input('Type the total recording time (min):') |
| 14 | filename=input('Type the file name (.xls):','s') |
| 15 | fnumber=round(60*total_time/interval); |
| 16 |  |
| 17 | im=getsnapshot(vid); |
| 18 | ref_image=im; |
| 19 | imwrite(im, 'Image0.tif', 'TIFF'); |
| 20 |  |
| 21 | number_segs=input('Type the nuber of segments:') |
| 22 | figure(1); imshow('Image0.tif'); hold on; |
| 23 | fprintf(2, '>>Click top left and then bottom right for each segment \n') |
| 24 |  |
| 25 | for i=1:number_segs |
| 26 | [Xs(i),Ys(i)]=ginput(1); |
| 27 | [Xf(i),Yf(i)]=ginput(1); |
| 28 | rectangle('Position', [Xs(i) Ys(i) abs(Xf(i)−Xs(i)) abs(Yf(i)−Ys(i))]) |
| 28 | end |
| 30 |  |
| 31 | ref_image_seg=cell(1,number_segs); |
| 32 | for i=1:number_segs |
| 33 |  |
| 34 | ref_image_seg{i}=ref_image(round(Ys(i)):round(Yf(i)), round(Xs(i)):round(Xf(i)),:); |
| 35 | end |
| 36 |  |
| 37 | fprintf('\n\n') |
| 38 | fprintf(2, 'Program is running. Press "Stop" to get out the program. \n') |
| 39 |  |
| 40 | for ctr=1:fnumber |
| 41 | imgg=getsnapshot(vid); |
| 42 | fname = ['Image' num2str(ctr)]; |
| 43 | imwrite(imgg, [fname '.tif'], 'TIFF'); |
| 44 |  |
| 45 | for j=1:number_segs |
| 46 | for k=1:3 |
| 47 |  |

TABLE 3-continued

Typical Matlab Code Example.

| Line | Code |
|---|---|
| 48 | cropped_image=imgg(round(Ys(j)):round(Yf(j)), round(Xs(j)):round(Xf(j)),:); |
| 49 | image_diff=int16(cropped_image)−int16 (ref_image_seg{j}); |
| 50 | meanRGB(ctr,j,k)=mean2(image_diff(:,:,k)); |
| 51 | end |
| 52 |  |
| 53 | data((ctr−1)*number_segs+j,1)=ctr; |
| 54 | data((ctr−1)*number_segs+j,2)=j; |
| 55 | data((ctr−1)*number_segs+j,3)=meanRGB(ctr,j,1); |
| 56 | data((ctr−1)*number_segs+j,4)=meanRGB(ctr,j,2); |
| 57 | data((ctr−1)*number_segs+j,5)=meanRGB(ctr,j,3); |
| 58 |  |
| 59 | x=[1:ctr]; |
| 60 | y=ones(3,ctr); |
| 61 | y(1,:)=data(((1:ctr)−1)*number_segs+j,3)'; |
| 62 | y(2,:)=data(((1:ctr)−1)*number_segs+j,4)'; |
| 63 | y(3,:)=data(((1:ctr)−1)*number_segs+j,5)'; |
| 64 | figure(2) |
| 65 | subplot(number_segs, 1, j); |
| 66 | plot(x,y(1,:),'r',x,y(2,:),'g',x,y(3,:),'b'); |
| 67 | end |
| 68 |  |
| 69 | xlswrite([filename '.xls'], data) |
| 70 | ctr=ctr+1; |
| 71 | pause(interval); |
| 72 | end |
| 73 |  |
| 74 | close(2) |
| 75 |  |
| 76 | stop(vid); |
| 77 | closepreview(vid); |
| 78 | clear vid; |

Surface Plasmon Resonance Analysis.

Surface plasmon resonance (SPR) analyses were performed using the Kretschmann optical configuration. A tungsten halogen lamp with a multi-wavelength light source was used, and a polarizer was positioned on the input path of the light for transverse magnetic fields. The prism coupler and the Phage litmus were mounted on an x-y-z stage. We made an enclosed cell of 100 μL using PDMS molds. Flow of solution to the cell was implemented using 1 mm internal diameter tube. We injected 1 mL of solution into the cell at a flow rate of 50 μL/min. The outflow from the cell was carried through to a reservoir. The reflected spectrum was measured by a fiber optic spectrometer (USB4000-UV-Vis, Ocean Optics, Dunedin, Fla.), and data acquisition was performed using a homemade LabVIEW program (Lab-VIEW 2009, National Instrument, Austin, Tex.). The SPR spectrum was calculated from linearly polarized light parallel/perpendicular to the incidence plane (TM/TE configuration).

iColor Analyser.

iColor analyzer is an iOS 5 application software built using the Xcode programming language (Xcode 4.2, Apple Inc., Cupertino, Calif.) and designed for the iPhone (compatible with the iPod and iPad; Apple Inc., Cupertino, Calif.). This software has been built in order to analyze colorimetric changes of the RGB components from a Phage litmus in a systematic manner using a handheld device. As demonstrated in this paper, the RGB color components and their changes from the Phage litmus can be linked to specific responses from analyte of interest. The iColor analyzer workflow is constituted of different parts (FIGS. 27-30), as follows:

Choice of Analysis Mode: A channel type (picker) is displayed in order to choose an analysis mode: single or double channel. Single channel mode samples from one to five color matrices of a Phage litmus labelled as S1-S5. The results display one to five different color matrix RGB components in a bar graph and their values on an 8-bit level. Double channel mode allows for color comparison analysis between a reference Phage litmus (before exposure to chemical) and the sample Phage litmus (after exposure to chemical) through comparison of between one to five matrices. The RGB values displayed will be the difference between the RGB values of the sample and the reference.

Phage Litmus Sample (The Picture Sampler): Once the user clicks on the single button of this application, the iPhone takes a picture of the Phage litmus. One can resize and crop the picture of the Phage litmus sample in order to precisely obtain the target area to analyze.

Data Analysis: Once the picture is taken, its central area is cropped and displayed. The picture is converted into a matrix containing the RGB and intensity values of each pixel. The vector data from the iPhone digital camera CCD (Omnivision OV5650, Santa Clara, Calif.) is processed to get the average of the RGB values from 2592×1944 pixels over the different areas selected by the user. An analysis table displays the RGB component intensity values and their standard deviations. An analysis graph will display the RGB values obtained from the sample. The "average" picture displays a synthesized picture made from either the average RGB values in the case of the single analysis mode, or the difference between the average RGB values of the Phage litmus and its reference in the case of the double comparison mode. After displaying the analysis data and the date and time, a screenshot of the interface is saved in the picture browser of the iPhone and can be transferred easily to any computer through e-mail. In this work, for display purposes, the color range of images are expanded from five to eight bits per color (red, green and blue color ranges of 0-31 expanded to 0-255).

Example 2

Figure 31:
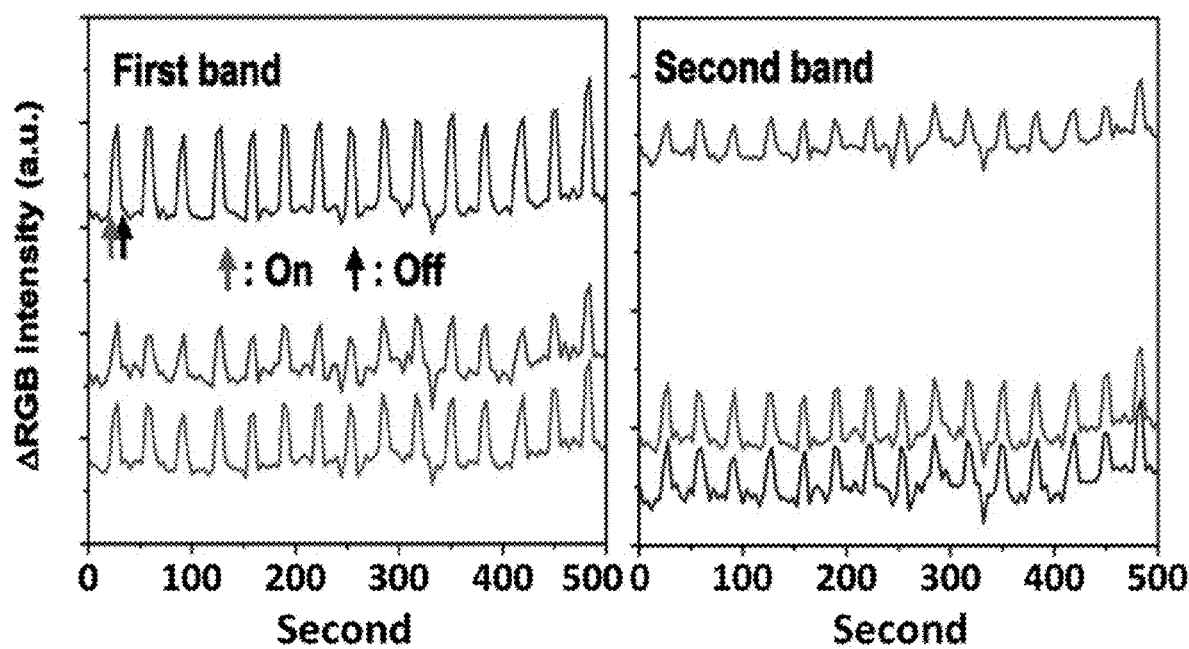
FIG. 31 illustrates preliminary methane gas sensing using the rationally designed phage colorsensor with Pt-DOPA receptors. Pt-DOPA phage colorsensor demonstration response plot to methane. The sensor was exposed to 50 mL/min natural gas (95% methane) for 8 sec followed by 25 seconds of exposure to ambient conditions. Orange and black arrows in plot represent the start and end of natural gas flow, respectively. Red, green, and blue lines represent RGB color component signals detected in USB camera.
Figure 32:
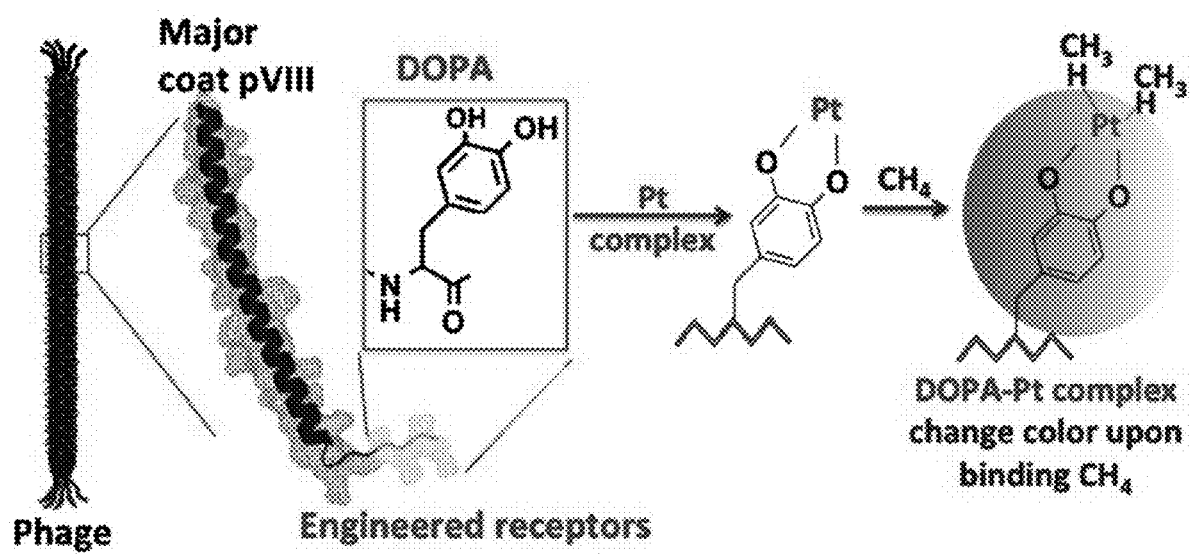
FIG. 32. Illustrates rational design of phage with transition metal-DOPA receptor. Genetically modified tyrosine expressed on p8 major coat protein M13 bacteriophage. (red box) Schematics of cathecol (DOPA transition) from tyrosine through tyrosinase enzymatic reaction. Chemical schematics of interaction of metal surface and DOPA moieties on the M13 phage. The resulting Pt-DOPA phage can change color upon exposure of methane gas due to Pt-methane coordination.

Methane Sensing Targeted Designed Phage:

We designed phage specifically for the detection of methane by engineering dioxyphenylalanine (DOPA) onto the phage major coat protein. First, we genetically expressed tyrosine (Y) on the major capsid p8 protein. Tyrosine was enzymatically converted to DOPA by tyrosinase (See FIG. 32 and task section for details). The resulting DOPA-phage strongly interacted with various organic and inorganic materials, allowing us to fabricate composite nanostructured films composed of DOPA-phage and transition metal or transition metal nanoparticles. A Pt-DOPA phage colorsensor (PC) was fabricated and we tested its colorimetric response to methane. Using methane gas, we alternated an 8 second exposure of 50 mL/min with a 25 second evacuation to ambient conditions. As shown in FIG. 31, repeated exposure to methane induced fast and reproducible colorimetric responses on the Pt-DOPA PC.

Engineered Phages with Rational Designed Receptors to Detect Methane:

To develop a phage that can detect the methane gas, a chemical receptor on the phage major coat protein is designed through chemical engineering approaches. Previously, Pt and Pd transition metal or their nanoparticles are known to interact with methane. Therefore, a novel engineered phage with 3,4-dihydroxyphenylalanine (DOPA) which complexes with Pt and Pd transition metals is designed. Tests showed that the resulting Pt-complexed phage generate rapid color changes upon the application of the methane, see results in FIG. 31).

Perform Methane Gas-Phage Binding Assays:

The amount of methane and other alkane gas adsorption is quantified using gas chromatography mass spectrometer (GC/MS).

Methane gas-phage binding assays: First the phage thin films with ~1 $cm^2$ chips are prepared. The phage films are then exposed to target gas in ambient air by placing the chips inside a scintillation tube containing a known amount of methane and other alkane gases in a temperature range (4-50° C.) for certain amount of time (10-120 min). The phage thin films are immediately analyzed for the amount of bound methane or other alkane gases by placement in a thermal desorption tube of a Unity thermal desorption system (Cincinnati, Ohio), which heats the chips to 200° C. The desorbed particles are directly sent to an Agilent GC/MS system (Santa Clara, Calif.). Partition coefficients are identified as the ratio of the concentration of analyte bound to the coating to the concentration of the analyte in the exposed gas headspace, normalized to the appropriate control conditions (i.e., blank substrates (silicon wafer)) in a temperature dependent manner and concentration dependent manners.

The processes set forth in this example are of use to develop phage-based colorimetric biosensor matrices that can respond to methane and other alkane gas molecules by controlling their nanostructures. The ability of the sensors to transduce the binding of methane and other alkane gases to colorimetric responses is readily assessed.

The most responsive phages discovered from phage display and other specifically designed phages to develop phage-based colorimetric sensor matrices are prepared using the well-established computer-controlled thin film growth process developed in our laboratory. Using these techniques, nanostructures to optimize the best responsive phage films for methane gas detection are developed.

Phage Color Sensor Fabrication:

Color sensor thin film are assembled using the fabrication process to create nano- and micro-structured phage films to fabricate sensitive PCs. A computer controlled phage deposition apparatus controls the rate and time over which a gold-coated silicon (or silicon) substrate is pulled from a phage suspension. The computer controlled thin films growth process can test up to 20 different concentration conditions with varying pulling speed. This high-throughput system can test hundreds of different thin film growth conditions overnight. This process utilizes chemically and genetically engineered phage (described previous sections) and controls various kinetic and thermodynamic parameters (i.e., phage concentration, ionic concentration, pulling speed, and surface chemistry), to create different liquid crystalline structures (i.e., nematic, cholesteric, smectic structures) with different size micro-patterns and different film thicknesses. The phage micropatterns is determined by reflective/transmission mode polarized optical microscopy, scanning electron microscopy, and/or AFM to determine the microstructure of the phage patterns.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The references cited are:
1 Bradbury, J. W. & Vehrencamp, S. L. *Principles of animal communication*. xiii, 882 p. (Sinauer Associates, Sunderland, Mass., 1998).
2 Vigneron, J. P. et al. Switchable reflector in the Panamanian tortoise beetle Charidotella egregia (Chrysomelidae: Cassidinae). *Physical Review E* 76, 031907 (2007).
3 Young, R. E. & Mencher, F. M. Bioluminescence in mesopelagic squid: diel color change during counterillumination. *Science* 208, 1286-1288, doi:10.1126/science.208.4449.1286 (1980).
4 Crookes, W. J. et al. Reflectins: The Unusual Proteins of Squid Reflective Tissues. *Science* 303, 235-238, doi: 10.1126/science. 1091288 (2004).
5. Tao, A. R. et al. The role of protein assembly in dynamically tunable bio-optical tissues. *Biomaterials* 31, 793-801, doi:10.1016/j.biomaterials.2009.10.038 (2010).
6 Kolle, M. et al. Mimicking the colorful wing scale structure of the Papilio blumei butterfly. *Nature Nanotechnology* 5, 511-515 (2010).
7 Vukusic, P. & Sambles, J. R. Photonic structures in biology. *Nature* 424, 852-855 (2003).
8 Sharma, V., Crne, M., Park, J. O. & Srinivasarao, M. Structural Origin of Circularly Polarized Iridescence in Jeweled Beetles. *Science* 325, 449-451, doi:10.1126/science.1172051 (2009).
9 Kramer, R. M., Crookes-Goodson, W. J. & Naik, R. R. The self-organizing properties of squid reflectin protein. *Nature Materials* 6, 533-538, (2007).
10 Prum, R. O. & Torres, R. H. Structural coloration of mammalian skin: convergent evolution of coherently scattering dermal collagen arrays. *Journal of Experimental Biology* 207, 2157-2172, doi:10.1242/jeb.00989 (2004).
11 Prum, R. O. & Torres, R. Structural coloration of avian skin: convergent evolution of coherently scattering dermal collagen arrays. *Journal of Experimental Biology* 206, 2409-2429, doi:10.1242/jeb.00431 (2003).
12 Kinoshita, S. & Yoshioka, S. Structural Colors in Nature: The Role of Regularity and Irregularity in the Structure. *Chem Phys Chem* 6, 1442-1459, doi:10.1002/cphc.200500007 (2005).
13 Noh, H. et al. How Noniridescent Colors Are Generated by Quasi-ordered Structures of Bird Feathers. *Advanced Materials* 22, 2871-2880, doi:10.1002/adma.200903699 (2010).
14 Forster, J. D. et al. Biomimetic Isotropic Nanostructures for Structural Coloration. *Advanced Materials* 22, 2939-2944, doi:10.1002/adma.200903693 (2010).
15 Potyrailo, R. A. et al. Morpho butterfly wing scales demonstrate highly selective vapor response. *Nature Photonics* 1, 123-128, (2007).
16 Burgess, I. B. et al. Encoding Complex Wettability Patterns in Chemically Functionalized 3D Photonic Crystals. *Journal of the American Chemical Society* 133, 12430-12432, doi:10.1021/ja2053013 (2011).
17 Ge, J. & Yin, Y. Responsive Photonic Crystals. *Angewandte Chemie International Edition* 50, 1492-1522, doi:10.1002/anie.200907091 (2011).
18 Kim, J. H., Moon, J. H., Lee, S.-Y. & Park, J. Biologically inspired humidity sensor based on three-dimensional photonic crystals. *Applied Physics Letters* 97, 103701-103703 (2010).
19 Bonifacio, L. D. et al. Towards the Photonic Nose: A Novel Platform for Molecule and Bacteria Identification. *Advanced Materials* 22, 1351-1354, doi:10.1002/adma.200902763 (2010).
20 Kelly, T. L., Garcia Sega, A. & Sailor, M. J. Identification and Quantification of Organic Vapors by Time-Resolved Diffusion in Stacked Mesoporous Photonic Crystals. *Nano Letters* 11, 3169-3173, doi:10.1021/nl201385p (2011).
21 Kang, Y., Walish, J. J., Gorishnyy, T. & Thomas, E. L. Broad-wavelength-range chemically tunable block-copolymer photonic gels. *Nature Materials* 6, 957-960, (2007).
22 Holtz, J. H. & Asher, S. A. Polymerized colloidal crystal hydrogel films as intelligent chemical sensing materials. *Nature* 389, 829-832 (1997).
23 Burgess, I. B. et al. Wetting in Color: Colorimetric Differentiation of Organic Liquids with High Selectivity. *ACS Nano* 6, 1427-1437, doi:10.1021/nn204220c (2012).
24 Lim, S. H., Feng, L., Kemling, J. W., Musto, C. J. & Suslick, K. S. An optoelectronic nose for the detection of toxic gases. *Nature Chemistry* 1, 562-567, (2009).
25 Chung, W.-J. et al. Biomimetic self-templating supramolecular structures. *Nature* 478, 364-368, (2011).
26 Lee, S.-W., Mao, C., Flynn, C. E. & Belcher, A. M. Ordering of Quantum Dots Using Genetically Engineered Viruses. *Science* 296, 892-895, doi:10.1126/science. 1068054 (2002).
27 Mao, C. et al. Virus-Based Toolkit for the Directed Synthesis of Magnetic and Semiconducting Nanowires. *Science* 303, 213-217, doi:10.1126/science. 1092740 (2004).
28 Sanghvi, A. B., Miller, K. P. H., Belcher, A. M. & Schmidt, C. E. Biomaterials functionalization using a novel peptide that selectively binds to a conducting polymer. *Nature Materials* 4, 496-502, (2005).
29 Nam, K. T. et al. Virus-Enabled Synthesis and Assembly of Nanowires for Lithium Ion Battery Electrodes. *Science* 312, 885-888, doi:10.1126/science. 1122716 (2006).
30 Lee, Y. J. et al. Fabricating Genetically Engineered High-Power Lithium-Ion Batteries Using Multiple Virus Genes. *Science* 324, 1051-1055, doi:10.1126/science.1171541 (2009).
31 Dang, X. et al. Virus-templated self-assembled single-walled carbon nanotubes for highly efficient electron collection in photovoltaic devices. *Nature Nanotechnology* 6, 377-384, (2011).
32 Merzlyak, A., Indrakanti, S. & Lee, S.-W. Genetically Engineered Nanofiber-Like Viruses For Tissue Regenerating Materials. *Nano Letters* 9, 846-852, doi:10.1021/nl8036728 (2009).
33 Zakhidov, A. A. et al. Carbon Structures with Three-Dimensional Periodicity at Optical Wavelengths. *Science* 282, 897-901, doi:10.1126/science.282.5390.897 (1998).
34 Fink, Y. et al. A Dielectric Omnidirectional Reflector. *Science* 282, 1679-1682, doi:10.1126/science.282.5394.1679 (1998).

35 Prum, R. O., Torres, R. H., Williamson, S. & Dyck, J. Coherent light scattering by blue feather barbs. *Nature* 396, 28-29 (1998).
36 Goldman, E. R., Pazirandeh, M. P., Charles, P. T., Balighian, E. D. & Anderson, G. P. Selection of phage displayed peptides for the detection of 2,4,6-trinitrotoluene in seawater. *Analytica Chimica Acta* 457, 13-19, doi:10.1016/s0003-2670(01)01246-6 (2002).
37 Kim, T. H. et al. Selective and Sensitive TNT Sensors Using Biomimetic Polydiacetylene-Coated CNT-FETs. *ACS Nano* 5, 2824-2830, doi:10.1021/nn103324p (2011).
38 Mao, C. B., Liu, A. H. & Cao, B. R. Virus-Based Chemical and Biological Sensing. *Angewandte Chemie-International Edition* 48, 6790-6810, doi:10.1002/anie.200900231 (2009).
39 Jaworski, J. W., Raorane, D., Huh, J. H., Majumdar, A. & Lee, S.-W. Evolutionary Screening of Biomimetic Coatings for Selective Detection of Explosives. *Langmuir* 24, 4938-4943, doi:10.1021/la7035289 (2008).
40. Rittfeldt L. Determination of vapor pressure of low-volatility compounds using a method to obtain saturated vapor with coated capillary columns. *Analytical Chemistry* 73, 2405-2411 (2001).
41. Berliner J F T, May O E. Studies in vapor pressure II The mononitrotoluenes. *Journal of the American Chemical Society* 48, 2630-2634 (1926).
42. Ostmark H, Wallin S, Ang H G. Vapor Pressure of Explosives: A Critical Review. *Propellants Explosives Pyrotechnics* 37, 12-23 (2012).

What is claimed is:

1. A method for detecting a first analyte of interest, said method comprising:
- providing a device comprising:
  - a colorimetric detection layer disposed on a substrate and configured to undergo a color change upon interaction with said analyte of interest, wherein said colorimetric detection layer comprises a first plurality of self-assembled substantially parallel fiber bundles comprising a filamentous member selected from the group consisting of filamentous viruses, filamentous fungi, filamentous bacteria, filamentous polysaccharides, and filamentous polypeptides, wherein said fiber bundles produce coherent scattering of visible light, and wherein at least a fraction of said fiber bundles undergo a structural change from a first conformation to a second conformation upon said interaction with said first said analyte of interest, thereby changing the color of light scattered from said fiber bundles;
  - a light source configured to illuminate said colorimetric detection layer and produce light scattered from said fiber bundles; and
  - a detector configured to detect the change in color of light scattered from the fiber bundles and to produce a signal indicating the presence or quantity of said analyte of interest when said analyte is introduced into said device;
- contacting said device with said first analyte, wherein said contacting causes at least a fraction of said fiber bundles to undergo said change from said first conformation to said second conformation upon said interaction with said first analyte of interest, thereby producing a change in color of the light scattered from said fiber bundles; and
- detecting a change in color of the light scattered from said fiber bundles where said change in color indicates the presence of said first analyte of interest.

2. The method of claim 1, wherein said first analyte of interest binds with a recognition moiety for said first analyte of interest.

3. The method of claim 1, wherein said fiber bundle in said second conformation is swollen with respect to said fiber bundle in said first conformation.

4. The method of claim 1, wherein said first plurality of self-assembled fiber bundles comprises a filamentous phage virus.

5. The method of claim 1, wherein said first plurality of self-assembled fiber bundles comprises a member selected from filamentous M13 phage, filamentous chitin, filamentous cellulose, filamentous collagen and a combination thereof.

6. The method of claim 1, wherein said first plurality of self-assembled fiber bundles are deposited on said substrate in a first matrix and in a second matrix.

7. The method of claim 1, wherein said first plurality of self-assembled fiber bundles is deposited on said substrate in a first matrix and a second plurality of self-assembled fiber bundles is deposited on said substrate in a second matrix, wherein said first matrix differs from said second matrix in a one or more of the following:
- (a) the spacing between fiber bundles comprising said first matrix and the spacing between fiber bundles comprising said second matrix; and/or
- (b) the identity of said filamentous member of said first matrix and said second matrix; and/or
- (c) the degree of elongation of said filamentous member of said first matrix and said second matrix.

8. The method of claim 7, wherein said first matrix changes to a first color upon interaction with said first analyte, and said second matrix changes to a second color upon interaction with a second analyte, and said first color and said second color are different colors.

9. The method of claim 1, wherein said substrate comprises a material selected from the group consisting of a metal, an inorganic material, and an organic polymer.

10. The method of claim 1, wherein said first analyte has a vapor pressure of less than or about 1 Atm.

11. The method of claim 1, wherein said first analyte has a vapor pressure of more than about 1 Atm.

12. The method of claim 1, wherein said detection layer further comprises a recognition moiety for said first analyte of interest bound to a member of said first plurality of self-assembled fiber bundles.

13. The method of claim 12, wherein said recognition moiety comprises an antibody or a carbohydrate.

14. The method of claim 1, wherein said detector comprises a charge coupled device (CCD).

15. The method of claim 14, wherein said detector is a component of a mobile device.

16. The method of claim 14, wherein said detector is a camera component of a mobile device.

* * * * *

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial
<220> FEATURE:
<223> OTHER INFORMATION: TNA binding peptide

<400> SEQUENCE: 1

Ala Asp Asp Trp His Trp Gln Glu Gly Asp Pro
1               5                   10

<210> SEQ ID NO 2
<211> LENGTH: 8
<212> TYPE: PRT
<213> ORGANISM: Artificial
<220> FEATURE:
<223> OTHER INFORMATION: TNA binding peptide

<400> SEQUENCE: 2

Asp Asp Trp His Trp Gln Glu Gln
1               5

<210> SEQ ID NO 3
<211> LENGTH: 8
<212> TYPE: PRT
<213> ORGANISM: Artificial
<220> FEATURE:
<223> OTHER INFORMATION: TNA binding peptide

<400> SEQUENCE: 3

Asp Asp Trp His Trp Gln Glu Gly
1               5

<210> SEQ ID NO 4
<211> LENGTH: 6
<212> TYPE: PRT
<213> ORGANISM: Artificial
<220> FEATURE:
<223> OTHER INFORMATION: TNA binding peptide

<400> SEQUENCE: 4

Ala Glu Gly Asp Asp Pro
1               5

<210> SEQ ID NO 5
<211> LENGTH: 6
<212> TYPE: PRT
<213> ORGANISM: Artificial
<220> FEATURE:
```

<223> OTHER INFORMATION: TNA binding peptide
<220> FEATURE:
<221> NAME/KEY: misc_feature
<222> LOCATION: (2)..(5)
<223> OTHER INFORMATION: Xaa can be any naturally occurring amino acid

<400> SEQUENCE: 5

Ala Xaa Xaa Xaa Xaa Pro
1               5

<210> SEQ ID NO 6
<211> LENGTH: 4
<212> TYPE: PRT
<213> ORGANISM: Artificial
<220> FEATURE:
<223> OTHER INFORMATION: TNA binding peptide

<400> SEQUENCE: 6

Trp His Trp Gln
1

<210> SEQ ID NO 7
<211> LENGTH: 11
<212> TYPE: PRT
<213> ORGANISM: Artificial
<220> FEATURE:
<223> OTHER INFORMATION: TNA binding peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 7

Ala Xaa Xaa Trp His Trp Gln Xaa Xaa Asp Pro
1               5                   10

<210> SEQ ID NO 8
<211> LENGTH: 63
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 8
atatatctgc agnknnktgg cattggcagn nknnkgatcc cgcaaaagcg gcctttaact      60
ccc                                                                  63

<210> SEQ ID NO 9
<211> LENGTH: 23
<212> TYPE: DNA

```
<213> ORGANISM: Artificial
<220> FEATURE:
<223> OTHER INFORMATION: PCR primer

<400> SEQUENCE: 9
gctgtctttc gctgcagagg gtg                                          23
```